US012791554B2

(12) United States Patent
Konry et al.

(10) Patent No.: US 12,791,554 B2
(45) Date of Patent: Nov. 10, 2026

(54) MICROFLUIDIC SYSTEM AND METHOD FOR REAL-TIME MEASUREMENT OF ANTIBODY-ANTIGEN BINDING AND ANALYTE DETECTION

(71) Applicants: Northeastern University, Boston, MA (US); The General Hospital Corporation, Boston, MA (US)

(72) Inventors: Tania Konry, Boston, MA (US); Martin L. Yarmush, Newton, MA (US)

(73) Assignees: Northeastern University, Boston, MA (US); The General Hospital Corporation, Boston, MA (US)

( * ) Notice: Subject to any disclaimer, the term of this patent is extended or adjusted under 35 U.S.C. 154(b) by 350 days.

(21) Appl. No.: 18/584,760

(22) Filed: Feb. 22, 2024

(65) Prior Publication Data

US 2024/0255498 A1 Aug. 1, 2024

Related U.S. Application Data

(62) Division of application No. 16/543,512, filed on Aug. 16, 2019, now Pat. No. 11,921,109, which is a (Continued)

(51) Int. Cl.
*G01N 33/543* (2006.01)
*B01F 25/433* (2022.01)
(Continued)

(52) U.S. Cl.
CPC ... *G01N 33/54313* (2013.01); *B01F 25/4331* (2022.01); *B01F 33/30* (2022.01); *B01L 3/5027* (2013.01); *B01L 3/502715* (2013.01); *B01L 3/502761* (2013.01); *B01L 3/502776* (2013.01); *G01N 21/6428* (2013.01); *G01N 33/5304* (2013.01); *G01N 33/54366* (2013.01); *B01L 2200/0605* (2013.01); *B01L 2200/0647* (2013.01); *B01L 2300/0654* (2013.01);
(Continued)

(58) Field of Classification Search
None
See application file for complete search history.

(56) References Cited

U.S. PATENT DOCUMENTS

| | | | | |
|---|---|---|---|---|
| 2004/0185551 A1* | 9/2004 | Niehaus | G01N 33/54373 | 436/514 |
| 2007/0172903 A1* | 7/2007 | Toner | B01L 3/502753 | 422/414 |
| 2007/0184456 A1* | 8/2007 | Chee | C12Q 1/6816 | 435/287.2 |

OTHER PUBLICATIONS

Li et al., A novel microfluidic mixer based on dual-hydrodynamic focusing for interrogating the kinetics of DNA-protein interaction, Analyst, 138, pp. 4475-4482, 2013. (Year: 2013).*

* cited by examiner

*Primary Examiner* — Rebecca M Giere
(74) *Attorney, Agent, or Firm* — Adams & Reese LLP

(57) ABSTRACT

Microfluidic devices for use with reagents bound to microspheres for determination of the concentration of an analyte in a liquid sample are provided. The devices include two sequential mixing channels that promote rapid binding of microsphere-bound reagents with reagents in solution and a means for detecting labeled microsphere-bound reaction products. Also provided are methods for using the devices with microsphere-bound reagents to determine the concentration of an analyte in a liquid sample and to measure the binding affinity of antibody for an antigen.

9 Claims, 23 Drawing Sheets

100

100

Related U.S. Application Data division of application No. 15/123,068, filed as application No. PCT/US2015/020704 on Mar. 16, 2015, now abandoned.

(60) Provisional application No. 61/953,347, filed on Mar. 14, 2014, provisional application No. 62/016,341, filed on Jun. 24, 2014, provisional application No. 62/050,538, filed on Sep. 15, 2014.

(51) Int. Cl.

| | |
|---|---|
| ***B01F 33/30*** | (2022.01) |
| ***B01L 3/00*** | (2006.01) |
| ***G01N 21/64*** | (2006.01) |
| ***G01N 33/53*** | (2006.01) |

(52) U.S. Cl.

CPC .................. *B01L 2300/0816* (2013.01); *B01L 2300/0867* (2013.01); *B01L 2300/087* (2013.01); *B01L 2300/0883* (2013.01); *B01L 2400/0487* (2013.01); *G01N 2021/6439* (2013.01); *G01N 2201/061* (2013.01)

Lab on a Chip (LOC) device

X = first analyte-binding agent (bound to microsphere)

Y* = labeled second analyte-binding agent

X = first analyte-binding agent (bound to microsphere)

Y* = labeled second analyte-binding agent

X* = labeled antibody-binding agent

Y = antibody

X = first enzyme (trapped within microsphere)

Y = second enzyme

Z = indicator precursor

Z* = indicator

A) Detection of anti-TNF α Ab

B) Detection of TNF α cytikine

Enzymatic reactions to detect glucose in microfluidic platform.

MICROFLUIDIC SYSTEM AND METHOD FOR REAL-TIME MEASUREMENT OF ANTIBODY-ANTIGEN BINDING AND ANALYTE DETECTION

CROSS REFERENCE TO RELATED APPLICATIONS

This application is a divisional application of U.S. application Ser. No. 16/543,512 filed 16 Aug. 2019, which is a divisional application of U.S. application Ser. No. 15/123,068 filed 1 Sep. 2016, now abandoned, which is the U.S. national phase of PCT Application No. PCT/US 2015/020704 filed 16 Mar. 2015, which claims the priority of U.S. Provisional Application Nos. 61/953,347 filed 14 Mar. 2014, 62/016,341 filed 24 Jun. 2014, and 62/050,538 filed 15 Sep. 2014. The entirety of each of the aforementioned applications is hereby incorporated by reference.

BACKGROUND

Rapid, sensitive and quantitative detection methods of disease markers are necessary for timely and effective diagnosis and therapy (Martinez et al., 2008). A major challenge in the detection of soluble molecules such as cytokines, protein antigens and antibodies is the ability to monitor time-varying or dynamic concentrations in real-time. Currently there are no available online monitoring approaches for continuous analyte immunoassays and pharmacokinetic characterization of biomolecules in real-time. At present, state-of-the-art analyte detection techniques for biomolecules include immunoassays such as enzyme-linked immunosorbent assays (ELISA), which are based on specific recognition of clinical antigens by the respective antibodies (Reichert, 2001). These diagnostic methods are performed on samples obtained at pre-defined times and are therefore laborious and time-intensive procedures. Additionally, these methods are impractical for real-time monitoring since they cannot be performed rapidly enough to assess dynamic fluctuation of analyte concentration in vivo. This limits their utility in clinical settings where it is of critical importance to generate real-time profile of analytes such as cytokines or administered drugs in vivo (Crowther, 2001; Mannerstedt et al., 2010; Mao et al., 2009; Wild, 2001).

In non-mixed solutions typically used in immunosorbent assays like ELISA, the binding reaction rates for reagents with low binding equilibrium constant, such as high affinity antibody-antigen interaction, depend on diffusion (Porstmann et al., 1992). Further increase of reaction surface or decrease of reaction volumes will not decrease the reaction time (Crowther, 2001). Therefore most, if not all, non-mixing immunoassay systems require incubation of 1-2 hours for analyte detection (Kusnezow et al., 2006; Ruslinga et al., 2010). Several developments in microfluidic based immunosorbent assay have been reported to address the problems associated with conventional immunoassays (Chen et al., 2011; Hou and Herr, 2010; Lee et al. 2009; Ng et al., 2010; Ng et al. 2012; Nie et al., 2014; Rissin et al, 2010; Thaitrong et al, 2013). In the microfluidic immunoassay format, increased surface area to volume ratios speeds up the antibody-antigen reactions while the smaller dimensions reduce the consumption of expensive reagents and precious samples (Kai et al., 2012; Thaitrong et al, 2013). Nevertheless, most of these methods still require incubation and are unable to measure the dynamic changes in the analyte concentration in real time (Hu and Gao, 2007; Singhal et al., 2010).

Most optical micro-devices for immunoassay proposed up to now are based on patterning lines of immobilized capture antibodies (Abs) in the micro-channels of the device and exposing these lines orthogonally to solutions of analytes (Hu and Gao, 2007; Singhal et al., 2010; Wolf et al., 2004). Then specifically captured analytes are detected with fluorescently labeled detection Abs creating a micromosaic of fluorescent zones, which reveals the binding events in a single imaging step. At this small scale, fluids exhibit laminar flow, i.e. fluidic streams that flow parallel to each other, and mixing occurs only by diffusion. Although diffusion distances in microchannels are significantly reduced in comparison to conventional microtiter well plate formats, analytes are still transport-limited in micro channels at low sample concentrations (Parsa et al., 2008). Thus both analyte capture and the fluorescently labeled antibody binding to the captured analyte still require an incubation step.

Consequently, there remains a need for devices and methods that allow for optical detection of analytes continuously in real time.

SUMMARY OF THE INVENTION

The present invention provides systems and methods for optical detection and quantification of an analyte in a sample. The systems and methods of utilize microfluidic devices to detect an analyte in a sample and to measure binding affinity of an antibody for an antigen.

One aspect of the invention is a microfluidic device for continuous flow optical detection and/or quantification of an analyte in a sample, the device including: first and second inlets; a first microscale laminar flow channel fluidically connected to the first and second inlets such that liquids entering from the first and second inlets flow in a laminar manner through said first laminar flow channel; a first microscale mixing channel fluidically connected to the first laminar flow channel such that liquid entering the first mixing channel from the first laminar flow channel is converted from laminar flow to non-laminar flow in said first mixing channel; a second microscale laminar flow channel fluidically connected to the first mixing channel; a third inlet fluidically connected to the second laminar flow channel such that liquids entering the second laminar flow channel from the third inlet and the first mixing channel flow in a laminar manner in said second laminar flow channel; a second microscale mixing channel fluidically connected to the second laminar flow channel such that liquid entering the second mixing channel from the second laminar flow channel is converted from laminar flow to non-laminar flow in said second mixing channel; an outlet fluidically connected to the second mixing channel; and a translucent detector region suitable for optical detection of the analyte, wherein the translucent detector region includes at least a portion of the second mixing channel or is disposed between the second mixing channel and the outlet or both.

In one embodiment, the translucent detector region is disposed between the second mixing channel and the outlet. In another embodiment the translucent detector region includes at least a portion of the second mixing channel. In some embodiments, the translucent detector region has a viewable area from about 250 $\mu m^2$ to about 2 $cm^2$.

In one embodiment, the device also includes a light source capable of transmitting light into the translucent detector region and a light sensor capable of sensing light emitted from the translucent detector region. In some embodiments, the device also includes a transmitter capable of transmitting information from the light sensor. In some embodiments, the device also includes a processor capable of receiving and processing the information transmitted from the transmitter. In some embodiments, the light sensor is a microscopic imaging system. In some embodiment, the light sensor is a photomultiplier or a photodiode.

In another embodiment, the device includes a fluid transport mechanism capable of transporting liquid though the first inlet at a first rate, through the second inlet at a second rate, and through the third inlet at a third rate. The fluid transport mechanism may be a pump, pressure port, or vacuum port.

In one embodiment, the dimensions of said first and second mixing channels permit diffusion-independent binding kinetics. In some embodiments, the first and second mixing channels each have cross-sectional areas from about 50 to about 250,000 $\mu m^2$. In some embodiments, the first laminar flow channel has a greater cross-sectional area than the cross-sectional area of the first mixing channel, and the second laminar flow channel has a cross-sectional area greater than the cross-sectional area of the second mixing channel. In some embodiments, the device has a fluidic path length encompassing the first and second laminar flow channels and the first and second mixing channels that is from about 0.1 to about 10 cm. In some embodiments, the first and second mixing channels each have fluidic path lengths from about 0.05 to about 5 cm.

In an embodiment, the first or second or both mixing channels include one or more curved regions. In some embodiments the first or second or both mixing channels include at least ten curved regions. In some embodiments, the curved regions include semi-circular arcs. In some embodiments, the first or second or both mixing channels have a serpentine structure. In some embodiments, the first or second or both mixing channels have a spiral configuration.

In some embodiments the device is made of polydimethylsiloxane (PDMS), glass, or a polymer material.

Another aspect of the invention is a system for optical detection of an analyte in sample, the system including a microfluidic device of the invention and a fluid suspension disposed within the second mixing channel, the suspension containing one or more microspheres. In some embodiments, one or more of the microspheres carries a fluorescent label.

In some embodiments, the system includes mechanism for delivering sample to the microfluidic device. In some embodiments, the mechanism is a microscale needle or a microdialysis membrane.

Another aspect of the invention is a method of determining a concentration of an analyte in a liquid sample, the method including: providing a microfluidic device for continuous flow optical detection of an analyte in a sample, a liquid suspension of microspheres that are conjugated to a first analyte-binding agent, a liquid comprising a labeled second analyte-binding agent, and a liquid sample suspected of comprising the analyte; flowing the liquid suspension of conjugated microspheres into the first inlet at a first flow rate; flowing the liquid sample into the second inlet at a second flow rate, whereby mixing of the conjugated microspheres and the liquid sample in the first mixing channel enables binding of analyte in the liquid sample to the first analyte-binding agent in a diffusion-independent manner, resulting in formation of analyte-coated microspheres; flowing the liquid comprising the labeled second analyte-binding agent into the third inlet at a third flow rate, whereby mixing of the analyte-coated microspheres and the labeled second analyte-binding agent in the second mixing channel enables binding of the labeled second analyte-binding agent to the analyte that coats the microspheres in a diffusion-independent manner, resulting in formation of labeled, analyte-coated microspheres; detecting an amount of microsphere-bound label; and determining a concentration of the analyte in the liquid sample based on a previously determined correlation between the amount of microsphere-bound label and concentration of the analyte.

In one embodiment, the analyte includes a molecule such as a protein, antibody, peptide, amino acid, hormone, growth factor, cytokine, cellular metabolite, nucleic acid, or oligosaccharide. In some embodiments, the molecule is a marker for a disease or medical condition. In some embodiments, the disease or medical condition is cancer or diabetes mellitus type 1. In some embodiments, the analyte is insulin, insulin aspart, insulin lispro, or glulisine.

In one embodiment, the microspheres have a diameter from about 1 μm to about 50 μm.

In one embodiment, the first, second, and third flow rates are each from about 1 to about 20 μl/min. In one embodiment, the ratio of first flow rate to second flow rate to third flow rate is about 1:1:2.

In one embodiment, the first or second or both analyte-binding agents include an antibody or an antigen-binding fragment thereof. In some embodiments, the first analyte-binding agent is HTB-124 or HTB-125. In some embodiments, the second analyte-binding agent is HTB-124 or HTB-125.

In one embodiment, the analyte is a first antibody, the first analyte-binding agent is an antigen that specifically binds to the first antibody, and the second analyte-binding agent is a second antibody that specifically binds to the first antibody.

In an embodiment, the amount of microsphere-bound label is detected by measuring fluorescence intensity. In one embodiment, measuring fluorescence intensity entails recording an image and analyzing the image for labeled microspheres.

In one embodiment, detection is performed over at least a portion of the second mixing channel. In one embodiment, detection is performed at a point in the second mixing channel. In one embodiment, detection is performed after the microspheres have exited the second mixing channel.

Another aspect of the invention is a method of determining concentrations of a first and second analytes in a liquid sample, the method including: providing (1) a microfluidic device for continuous flow optical detection of an analyte in a sample, (2) a liquid suspension of a first and second populations of microspheres, the microspheres in the first population being conjugated to a first binding agent that binds the first analyte, and the microspheres in the second population being conjugated to a first binding agent that binds the second analyte, (3) a liquid comprising a first labeled second binding agent that binds the first analyte and second labeled second binding agent that binds the second analyte, and (4) a liquid sample suspected of comprising said first and second analytes; flowing the liquid suspension of conjugated microspheres into the first inlet at a first flow rate; flowing the liquid sample into the second inlet at a second flow rate, whereby mixing of the conjugated microspheres and the liquid sample in the first mixing channel enables binding of the first analyte to the corresponding first binding agent on the first population of microspheres and binding of the second analyte to the corresponding first binding agent on the second population of microspheres in a diffusion-independent manner, resulting in formation of a first population of microspheres coated with first analyte and a second population of microspheres coated with second analyte; flowing the liquid comprising the labeled second binding agents into the third inlet at a third flow rate, whereby mixing of the analyte-coated microspheres and the labeled second binding agents in the second mixing channel enables binding of the labeled second binding agents to the corresponding microspheres in a diffusion-independent manner, resulting in formation of a first population of first labeled microspheres and a second population of second labeled microspheres; detecting amounts of microsphere-bound first label and microsphere-bound second label; and determining concentrations of the first and second analytes in the liquid sample based on a previously determined correlation between the amount of microsphere-bound label and concentration of analyte.

Another aspect of the invention is a method of determining a concentration of an analyte in a liquid sample, the method including: providing a microfluidic device for continuous flow optical detection of an analyte in a sample, a liquid suspension of microspheres that are conjugated to a first analyte-binding agent, a liquid comprising a labeled second analyte-binding agent, and a liquid sample suspected of comprising said analyte; flowing the liquid sample into the first inlet at a first flow rate; flowing the liquid comprising the labeled second analyte-binding agent into the second inlet at a second flow rate, whereby mixing of the liquid sample and the labeled second analyte-binding agent enables binding of the labeled second analyte-binding agent to the analyte, resulting in formation of labeled analyte complexes in a diffusion-independent manner; flowing the liquid suspension of conjugated microspheres into the third inlet at a third flow rate, whereby mixing of the conjugated microspheres and the labeled analyte complexes in the second mixing channel enables binding of the labeled analyte complexes to the conjugated microspheres in a diffusion-independent manner, resulting in formation of labeled, analyte-coated microspheres; detecting an amount of microsphere-bound label; and determining a concentration of the analyte in the liquid sample based on a previously determined correlation between the amount of microsphere-bound label and concentration of the analyte.

Another aspect of the invention is a method of determining a concentration of a first and second analytes in a liquid sample, the method including: providing (1) a microfluidic device for continuous flow optical detection of an analyte in a sample, (2) a liquid suspension of a first and second populations of microspheres, the microspheres in the first population being conjugated to a first binding agent that binds the first analyte and having an approximately uniform diameter, and the microspheres in the second population being conjugated to a first binding agent that binds the second analyte, (3) a liquid comprising a first labeled second binding agent that binds the first analyte and second labeled second binding agent that binds the second analyte, and (4) a liquid sample suspected of comprising said first and second analytes; flowing the liquid sample into the first inlet at a first flow rate; flowing the liquid comprising the labeled second binding agents into the second inlet at a second flow rate, whereby mixing of the liquid sample and the labeled second binding agents enables binding of the first labeled second binding agent to the first analyte and binding of the second labeled binding agent to the second analyte in a diffusion-independent manner, resulting in formation of first labeled first analyte complexes and second labeled second analyte complexes; flowing the liquid suspension of conjugated microspheres into the third inlet at a third flow rate, whereby mixing of the conjugated microspheres and the labeled analyte complexes in the second mixing channel enables binding of the labeled analyte complexes to the corresponding conjugated microspheres in a diffusion-independent manner, resulting in formation of a first population of first labeled microspheres and a second population of second labeled microspheres; detecting amounts of microsphere-bound first label and microsphere-bound second label; and determining concentrations of the first and second analytes in the liquid sample based on a previously determined correlation between the amount of microsphere-bound label and concentration of analyte.

Another aspect of the invention is a method of determining the binding affinity of an antibody for an antigen, the method including: providing a microfluidic device for continuous flow optical detection of an analyte in a sample, a liquid suspension of microspheres that are conjugated to an antigen binding agent, a liquid comprising the antigen, and a liquid comprising the antibody conjugated to a label; flowing the liquid suspension of conjugated microspheres into the first inlet at a first flow rate; flowing the liquid comprising the antigen into the second inlet at a second flow rate, whereby mixing of the conjugated microspheres and the antigen in the first mixing channel enables binding of the antigen to the antigen binding agent in a diffusion-independent manner, resulting in formation of antigen-coated microspheres; flowing the liquid comprising the labeled antibody into the third inlet at a third flow rate, whereby mixing of the antigen-coated microspheres and the labeled antibody in the second mixing channel enables binding of the labeled antibody to the antigen-coated microspheres in a diffusion-independent manner, resulting in formation of labeled antibody-coated microspheres; detecting an amount of microsphere-bound label at one or more different points in the second mixing channel; and determining the binding affinity of the antibody for the antigen by comparing the amount of microsphere-bound label at one or more different points in the second mixing channel.

In one embodiment, the antigen includes a molecule such as a protein, antibody, peptide, amino acid, hormone, growth factor, cytokine, cellular metabolite, nucleic acid, or oligosaccharide. In some embodiments, the molecule is a marker for a disease or medical condition, for example, cancer.

In one embodiment, the antibody is a first antibody that binds to a first epitope on the antigen and the antigen-binding agent is a second antibody that binds to a second epitope on the antigen.

Another aspect of the invention is a method of determining the binding affinity of an antibody for an antigen, the method including: providing a microfluidic device for continuous flow optical detection of an analyte in a sample, a liquid suspension of microspheres that are conjugated to the antigen, a liquid comprising the antibody, and a liquid comprising an antibody binding agent conjugated to a label; flowing the liquid comprising the antibody into the first inlet at a first flow rate; flowing the liquid comprising the labeled antibody binding agent into the second inlet at a second flow rate, whereby mixing of the antibody and the labeled antibody binding agent in the first mixing channel enables binding of the antibody to the labeled antibody binding agent in a diffusion-independent manner, resulting in formation labeled antibody complexes; flowing the liquid suspension of conjugated microspheres into the third inlet at a third flow rate, whereby mixing of the conjugated microspheres and the labeled antibody complexes in the second mixing channel enables binding of the antigen to the antibody in a diffusion-independent manner, resulting in formation of labeled antibody-coated microspheres; detecting an amount of microsphere-bound label at one or more different points in the second mixing channel; and determining the binding affinity of the antibody for the antigen by comparing the amount of microsphere-bound label at one or more different points in the second mixing channel.

In one embodiment, the antibody is a first antibody that binds to the antigen and the antigen-binding agent is a second antibody that binds to the first antibody.

Another aspect of the invention is a method of determining a concentration of an analyte in a liquid sample, the method including: providing (1) a microfluidic device for continuous flow optical detection of an analyte in a sample, (2) a liquid suspension containing microspheres containing a first enzyme trapped within the microspheres, the first enzyme capable of converting an indicator precursor into an indicator in the presence of a diffusible agent, and the indicator precursor, (3) a liquid containing a second enzyme, the second enzyme capable of producing the diffusible agent in the presence of the analyte, and (4) a liquid sample suspected of containing the analyte; flowing the liquid sample into the first inlet at a first flow rate; flowing the liquid containing the second enzyme into the second inlet at a second flow rate, whereby mixing of the liquid sample and liquid containing the second enzyme in the first mixing channel enables the second enzyme to produce the diffusible agent; flowing the liquid suspension of microspheres into the third inlet at a third flow rate, whereby mixing of the microspheres and the diffusible agent in the second mixing channel enables the first enzyme to convert the indicator precursor into the indicator; detecting an amount of indicator associated with the microspheres; and determining a concentration of the analyte in the liquid sample based on a previously determined correlation between the amount of indicator associated with the microspheres and concentration of the analyte.

In some embodiments, the microspheres contain the indicator precursor. In some embodiments, the microsphere is made of a hydrogel. In some embodiments, the hydrogel is poly(lactic-co-glycolic acid) (PLGA), polyethylene glycol [PEG] methacrylate and acrylates, poly(acrylic acid), poly (methacrylic acid), 2-diethylaminoethylmethacrylate, 2-aminoethyl methacrylate, poly(ethylene glycol) dimethacrylates and acrylates, acrylamide/bisacrylamide, poly(2-hydroxyethyl methacrylate), methacrylated dextrans, acrylated dextrans, poly(ethylene glycol)-polyester acrylated/methacrylated block copolymer, cellulose acetate phthalate, hydroxypropyl-methyl cellulose phthalate poly(butyl methacrylate), or methyl methacrylate.

In some embodiments, the first enzyme is horseradish peroxidase.

In some embodiments, the second enzyme is glucose oxidase.

In some embodiments, the indicator is 10-Acetyl-3,7-dihydroxyphenoxazine.

In some embodiments, the diffusible agent is $H_2O_2$.

Another aspect of the invention is a kit for determining the concentration of an analyte in a liquid, the kit including: a microfluidic device for continuous flow optical detection of an analyte in a sample, a plurality of microspheres conjugated to a first analyte-binding agent, and a labeled second analyte-binding agent.

Another aspect of the invention is a kit for determining the concentration of an analyte in a liquid, the kit including: a microfluidic device for continuous flow optical detection of an analyte in a sample and a plurality of microspheres containing an enzyme trapped within the microspheres, the enzyme capable of converting an indicator precursor into an indicator in the presence of a diffusible agent.

In some embodiments, the kit includes instructions for using of the kit according to a method of the invention.

In some embodiments, the kit includes an indicator precursor. In some embodiments, the kit includes an enzyme capable of producing the diffusible agent in the presence of the analyte.

Another aspect of the invention is a kit for measuring binding affinity of an antibody to an antigen, the kit including a microfluidic device for continuous flow optical detection of an analyte in a sample, a plurality of microspheres conjugated to an antigen binding agent, and the antigen.

Another aspect of the invention is a kit for measuring binding affinity of an antibody to an antigen, the kit including: a microfluidic device for continuous flow optical detection of an analyte in a sample, a plurality of microspheres conjugated to the antigen, and a labeled antibody binding agent.

Another aspect of the invention is a method of determining concentrations of a first and second analytes in a liquid sample, the method including: providing (1) a microfluidic device for continuous flow optical detection of an analyte in a sample, (2) a liquid sample suspected of containing the first and second analytes, (3) a first liquid suspension containing a first enzyme and a first population of microspheres, the first enzyme capable of producing a diffusible agent in the presence of the second analyte, and the microspheres of the first population being conjugated to a first binding agent that binds the first analyte, and (4) a second liquid suspension containing a labeled second binding agent that binds the first analyte, an indicator precursor, and a second population of microspheres, the microspheres of the second population containing a second enzyme trapped within the microspheres, the second enzyme capable of converting the indicator precursor into an indicator in the presence of the diffusible agent; flowing the liquid sample into the first inlet at a first flow rate; flowing the first liquid suspension into the second inlet at a second flow rate, whereby mixing of the first liquid suspension and the liquid sample in the first mixing channel enables (1) binding of the first analyte to the first binding agent conjugated to microspheres of the first population, resulting in formation of first analyte-coated microspheres by the time the microspheres of the first population exit the first mixing channel, and (2) the first enzyme to produce the diffusible agent; flowing the second liquid suspension into the third inlet at a third flow rate, whereby mixing of the efflux from the first mixing channel with the second liquid suspension in the second mixing channel enables (1) binding of the labeled second binding agent to the analyte that coats the conjugated microspheres of the first population, resulting in formation of microspheres coated with labeled second analyte-binding agent by the time the microspheres of the first population exit the second mixing channel, and (2) the second enzyme trapped in the microspheres of the second population to convert the indicator precursor into the indicator; detecting an amount of label bound to microspheres of the first population and an amount of indicator associated with microspheres of the second population; and determining a concentration of the first analyte in the liquid sample based on a previously determined correlation between the amount of microsphere-bound label and concentration of analyte, and determining a concentration of the second analyte in the liquid sample based on a previously determined correlation between the amount of indicator associated with the microspheres and concentration of the analyte.

Another aspect of the invention is a method of determining concentrations of a first and second analytes in a liquid sample, the method including: providing (1) a microfluidic device for continuous flow optical detection of an analyte in a sample, (2) a liquid sample suspected of containing said first and second analytes; (3) a liquid solution containing a first enzyme and a labeled first binding agent that binds the first analyte, the first enzyme capable of producing a diffusible agent in the presence of the second analyte; and (4) a liquid suspension containing a first population of microspheres, a second population of microspheres, and an indicator precursor, the microspheres of the first population being conjugated to a second binding agent that binds the first analyte, and the microspheres of the second population containing a second enzyme trapped within the microspheres, the second enzyme capable of converting the indicator precursor into an indicator in the presence of the diffusible agent; flowing the liquid sample into the first inlet at a first flow rate; flowing the liquid solution into the second inlet at a second flow rate, whereby mixing of the liquid solution and the liquid sample in the first mixing channel enables (1) binding of the labeled first binding agent to the first analyte, resulting in formation of labeled first analyte complexes by the time the microspheres exit the first mixing channel, and (2) the first enzyme to produce the diffusible agent; flowing the liquid suspension into the third inlet at a third flow rate, whereby mixing of the efflux from the first mixing channel with the liquid suspension in the second mixing channel enables (1) binding of the labeled first analyte complexes to the conjugated microspheres of the first population, resulting in formation of microspheres coated with complexes of analyte and labeled first binding agent by the time the microspheres of the first population exit the second mixing channel; and (2) the second enzyme trapped in the microspheres of the second population to convert the indicator precursor into the indicator; detecting an amount of label bound to microspheres of the first population and an amount of indicator associated with microspheres of the second population; and determining a concentration of the first analyte in the liquid sample based on a previously determined correlation between the amount of microsphere-bound label and concentration of analyte, and determining a concentration of the second analyte in the liquid sample based on a previously determined correlation between the amount of indicator associated with the microspheres and concentration of the analyte.

BRIEF DESCRIPTION OF THE DRAWINGS

FIGS. 15B-1 and 15B-2 show microscopic images of microspheres from the assay. Left panel (FIG. 15B-1) is a phase contrast image, and right panel (FIG. 15B-2) is a fluorescence image of the same field (excitation 494 nm, emission 519 nm).

DETAILED DESCRIPTION OF THE INVENTION

Figure 1A:
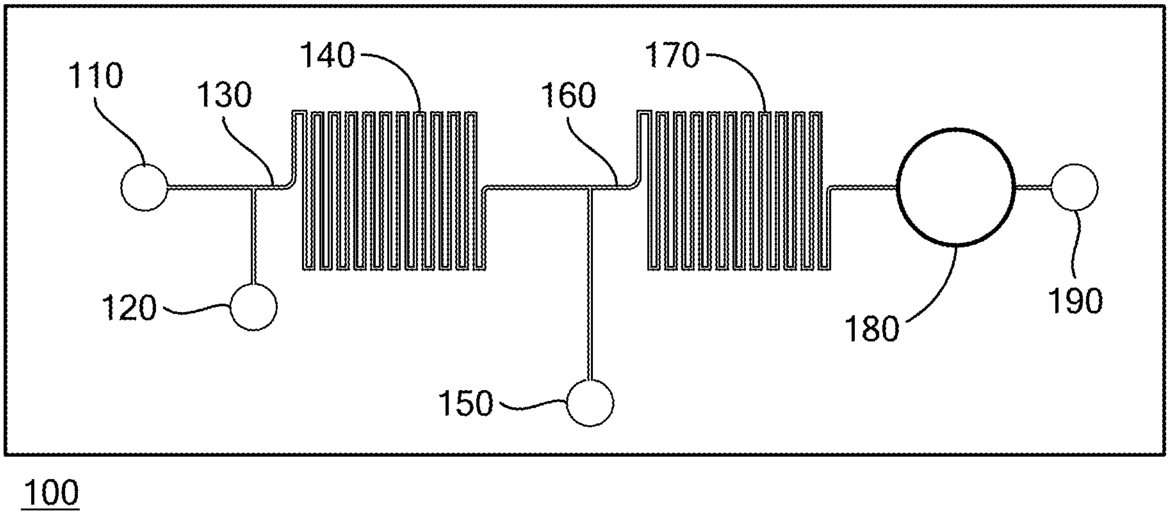
FIG. 1A is a schematic of an embodiment of a device of the invention.

The present invention provides devices and methods for real-time detection and quantification of analyte in a liquid sample and for measuring binding affinity of an antibody for its antigen. The devices of the invention include microfluidic channels that allow transport and mixing of small volumes of liquid in the microliter or nanoliter range. The design of the channel allows mixing of liquids in two sequential mixing channels. The methods of the invention include transporting liquids through the devices described herein in a way that promotes rapid mixing, allowing binding reactions to occur in a diffusion-independent manner, and eliminates the need for washing steps.

Conventional immunosorbent assays like ELISA are diffusion dependent, which can necessitate significant incubation periods when employing high affinity antibody-antigen interactions. The devices and methods described herein overcome the limitation of diffusion-dependent adsorption kinetics by utilizing a microsphere-based assay in a microfluidic device format that introduces non-laminar flow profiles in the reaction region. In the microfluidic devices described herein, the sample and microsphere-based assay reagents are continuously replenished in the device to perform continuous detection of the analyte in real time and using a minimal amount of biological specimen.

Integrating microsphere-based immunoassays with the developed herein microfluidics has major advantages over flat-surface assays such as ELISA. Microspheres have larger surface area, so the interaction between microspheres and target molecules in the well-mixed flow based format is practically comparable with solution-phase kinetics. Furthermore, due to the fast reaction kinetics, this lab-on-a-chip (LOC) approach is capable of performing near real-time detection of clinically relevant analytes such as cytokines, proteins, antibodies and drugs.

The sensitivity and specificity of the developed LOC method were tested and compared to the standard immunoassays available commercially. The developed LOC method allows one to reduce reagent volumes by nearly three orders of magnitude, eliminate the washing steps required by standard immunoassays, and enhance detection reaction rates to accomplish near real-time monitoring of clinically relevant targets. In particular, the time to obtain a specific conjugation/coverage on the microsphere surface in well-mixed microfluidic LOC is achieved in seconds in the flow through incubation channel compared to 1-2 hours in the non-well mixed solutions, thus allowing near real-time detection in the developed LOC. Furthermore the developed simple LOC platform can be applied for real time point of care diagnostics of inflammation, infectious diseases and other diseases where the detection is based on antibody-antigen interactions for specific detection of the disease clinical markers.

As used herein, the term "microscale" refers to an object or feature whose size is in the range from about 1 μm to about 999 μm, or to less than 1 mm. "Microfluidic" refers to fluid flow through microscale objects or features, including channels and other fluid handling structures in a device such as a "lab-on-a-chip" device.

Figure 1B:
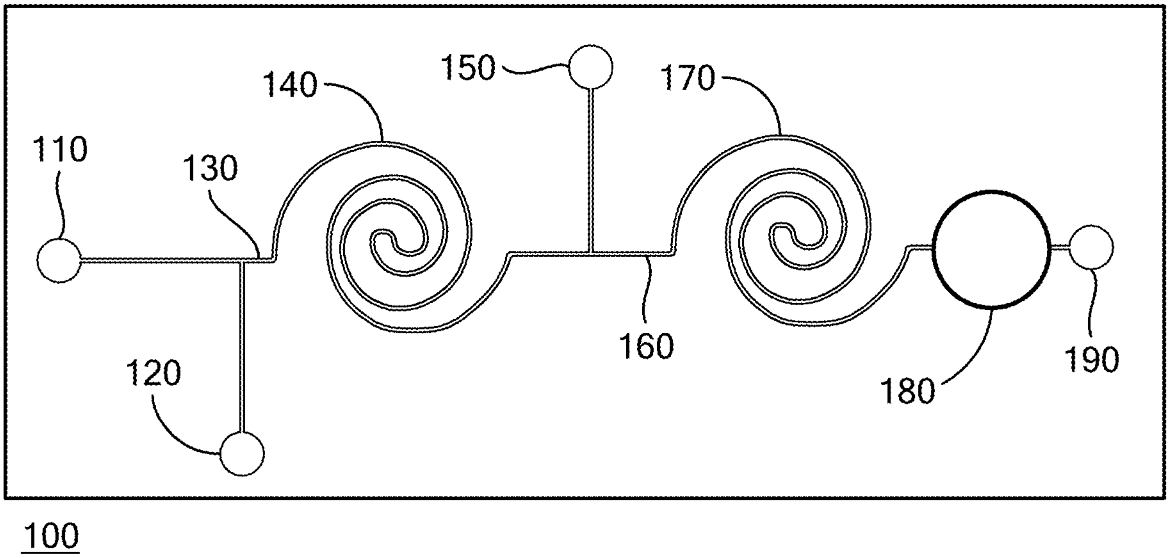
FIG. 1B is a schematic of another embodiment of the invention.
Figure 1C:
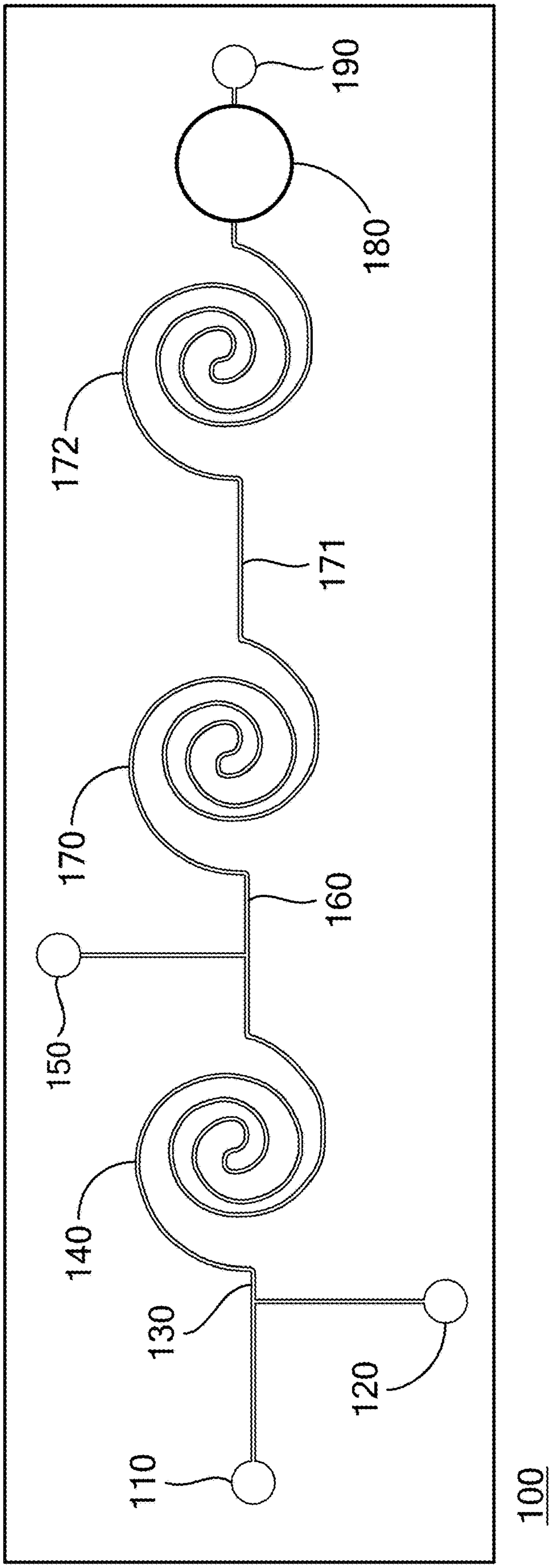
FIG. 1C is a schematic of another embodiment of the invention.

The invention includes a microfluidic device (100) for continuous flow optical detection of an analyte in a sample. As shown in FIGS. 1A-1C, the device includes a first inlet (110) and second inlet (120) that are fluidically connected to a first laminar flow channel (130). A first mixing channel (140) is fluidically connected at one to the first laminar flow channel and at the other end to a second laminar flow channel (160). A third inlet (150) is fluidically connected to the second laminar flow channel. A second mixing channel (170) is fluidically connected at one end to the second laminar flow channel and at the other end to an outlet (190). The second mixing channel may be separated from the outlet by a non-mixing channel, as shown in FIGS. 1A-IC. As shown in FIG. 1C, the microfluidic device may also contain a connecting channel (171) and third mixing channel (172) downstream of the second mixing channel.

The microfluidic device also includes a translucent detector region (180). The translucent detector region may be positioned between the second mixing channel and the outlet, as shown in FIGS. 1A-1C. Alternatively, the translucent detector region may be positioned over a portion of the second mixing channel, or over a portion of another downstream mixing channel, e.g., a third, fourth, fifth, etc. mixing channel. In another embodiment, the translucent detector region is positioned both between the second mixing channel and the outlet and over a portion of the second mixing channel. The translucent detector region may have a cross-sectional area from about 250 $\mu m^2$ to about 200,000,000 $\mu m^2$ (=2 $cm^2$) or any sub-range within that range, such as, but without limitation, from about 250 to about 2500 $\mu m^2$, from about 2500 to about 25,000 $\mu m^2$, from about 25,000 to about 250,000 $\mu m^2$, from about 250,000 to about 2,500,000 $\mu m^2$, from about 2,500,000 to about 25,000,000 $\mu m^2$, or from about 25,000,000 to about 200,000,000 $\mu m^2$.

The device is configured to allow rapid mixing of liquids in the mixing channels. When a first liquid enters the first laminar flow channel from the first inlet and a second liquid enters the first laminar flow channel from the second inlet, the liquids flow in a laminar flow pattern. As these liquids enter the first mixing channel, however, they flow in a non-laminar manner due to the shape and dimensions of the first mixing channel, and the two liquids are thoroughly mixed. The efflux from the first mixing channel enters the second laminar flow channel, where it encounters a third liquid from the third inlet channel, and the two fluid streams flow in a laminar pattern. As the liquids flow into the second mixing channel, they again flow in a non-laminar patterns due to the shape and dimensions of the first mixing channel, and the these liquids are thoroughly mixed. Thus, by the time fluid exits the second mixing channel, it is a homogeneous mixture of three input liquids that have been mixed in two separate steps.

The shape of the mixing channels is an important feature that enables the microfluidic device to achieve rapid mixing of liquids. Each mixing channel has one or more curved regions that promotes non-laminar flow. In some embodiments, the mixing channel has ten or more curved regions. The curved region may be an arc or part of a circle, for example, a semi-circular arc. A mixing channel may have a series of alternating semi-circular arcs and straight regions arrayed in parallel to form a serpentine structure. A mixing channel may have a spiral configuration. As used herein, “spiral” refers to any type of spiral, including but not limited to, an Archimedean spiral, Cornu spiral, Fermat’s spiral, hyperbolic spiral, lituus spiral. logarithmic spiral, and spiral of Theodorus. The first and second mixing channels may have the same shape, or they may have different shapes. The mixing channels may promote mixing by hydrodynamic focusing, geometry effect, electrokinetics, droplet mixing, particle stirring, or a combination of these or other means.

The dimensions of the microfluidic device can affect its function. The use of narrow channels throughout the microfluidic device decreases the volume of the fluid path in the device. This is advantageous because it allows the device to be used with small amounts of precious reagents or liquid samples. The mixing channels may have a cross-sectional area from about 50 to about 250,000 $\mu m^2$ or any sub-range within that range, such as, but without limitation, from about 50 to about 500 $\mu m^2$, from about 500 to about 5000 $\mu m^2$, from about 5000 to about 50,000 $\mu m^2$, or from about 50,000 to about 250,000 $\mu m^2$. The first and second mixing channels may have the same cross-sectional area, or they may have different cross-sectional areas.

In addition, the use of mixing channels that are narrower than the upstream-adjacent laminar flow channels promotes non-laminar flow within the mixing channels. Thus, the first laminar flow channel may have a cross-sectional area greater than the cross-sectional area of the first mixing channel, and the second laminar flow channel may have a cross-sectional area greater than the cross-sectional area of the second mixing channel.

The fluidic path length can affect the function of the device. The length of the fluidic path through the first laminar flow channel, the first mixing channel, the second laminar flow channel, and the second mixing channel may be from about 0.1 to about 10 cm or any sub-range within that range, such as, but without limitation, from about 0.1 to about 1 cm, or from about 1 cm to about 10 cm. The fluidic path of an individual mixing channel may be from about 0.05 to about 5 cm or any sub-range within that range, for example, but without limitation, from about 0.05 to about 0.5 cm or from about 0.5 to about 5 cm.

The total fluidic volume capacity of the device depends on the dimensions described above. The total fluidic volume capacity of the first laminar flow channel, the first mixing channel, the second laminar flow channel, and the second mixing channel may be from about 0.1 to about 100 µl or any sub-range within that range, such as, but without limitation, from about 0.1 to about 1 µl, from about 1 to about 10 µl, or from about 10 to about 100 µl.

The microfluidic device may include a fluid transport mechanism capable of transporting liquid through the first inlet at a first rate, through the second inlet at a second rate, and through the third inlet at a third rate. The fluid transport mechanism may be a pump, pressure port, vacuum port, or any other mechanism suitable for transporting fluid through the microfluidic device.

The device may be made of polydimethylsiloxane (PDMS), glass, a polymer material, or any other suitable material. The device may be reusable or disposable. The device may be made for implantation in a subject.

The device may include a reservoir in fluidic connection with the first or second laminar flow channels. The reservoir may be used for storage of a reagent or liquid sample for use in the microfluidic device. The reservoir may be in contact with a source of a liquid sample. The device may include a sample collection and/or processing mechanism, such as a microneedle, a dialysis membrane, an ultrafiltration membrane, or a binding agent to restrict entry of cells or certain biomolecules into reservoir and the laminar and mixing channels of the device. The device may include more than one such reservoir.

The invention also encompasses systems for optical detection of analyte that include a device of the invention. For example, the system may include any of the microfluidic device embodiments contemplated herein, having a fluid suspension of microspheres within one or more of the microfluidic channels.

The system may also include a light source capable of transmitting light into the translucent detector region. The system may include a light sensor capable of sensing light emitted from the translucent detector region. The light sensor may be a photodiode, photomultiplier, microscopic imaging system, or any other means of sensing light. The system may include a transmitter capable of transmitting information from the light sensor. The system may include a processor capable of receiving and processing information transmitted from the transmitter.

The system may include a mechanism for acquiring and delivering a sample to the device. For example, the system may include a microscale needle in fluidic connection with the first, second, or third inlet. The microscale need may be in contact with a source of liquid sample, a reagent source, or other liquid sources.

The system may also include a mechanism for processing the sample prior to sample delivery. For example, the system may include a mechanism for removing particulates, cells, and other insoluble objects from the sample. For example, the system may include a microscale dialysis device or a deterministic lateral displacement device (see, e.g., Huang et al., 2004).

Figure 2:
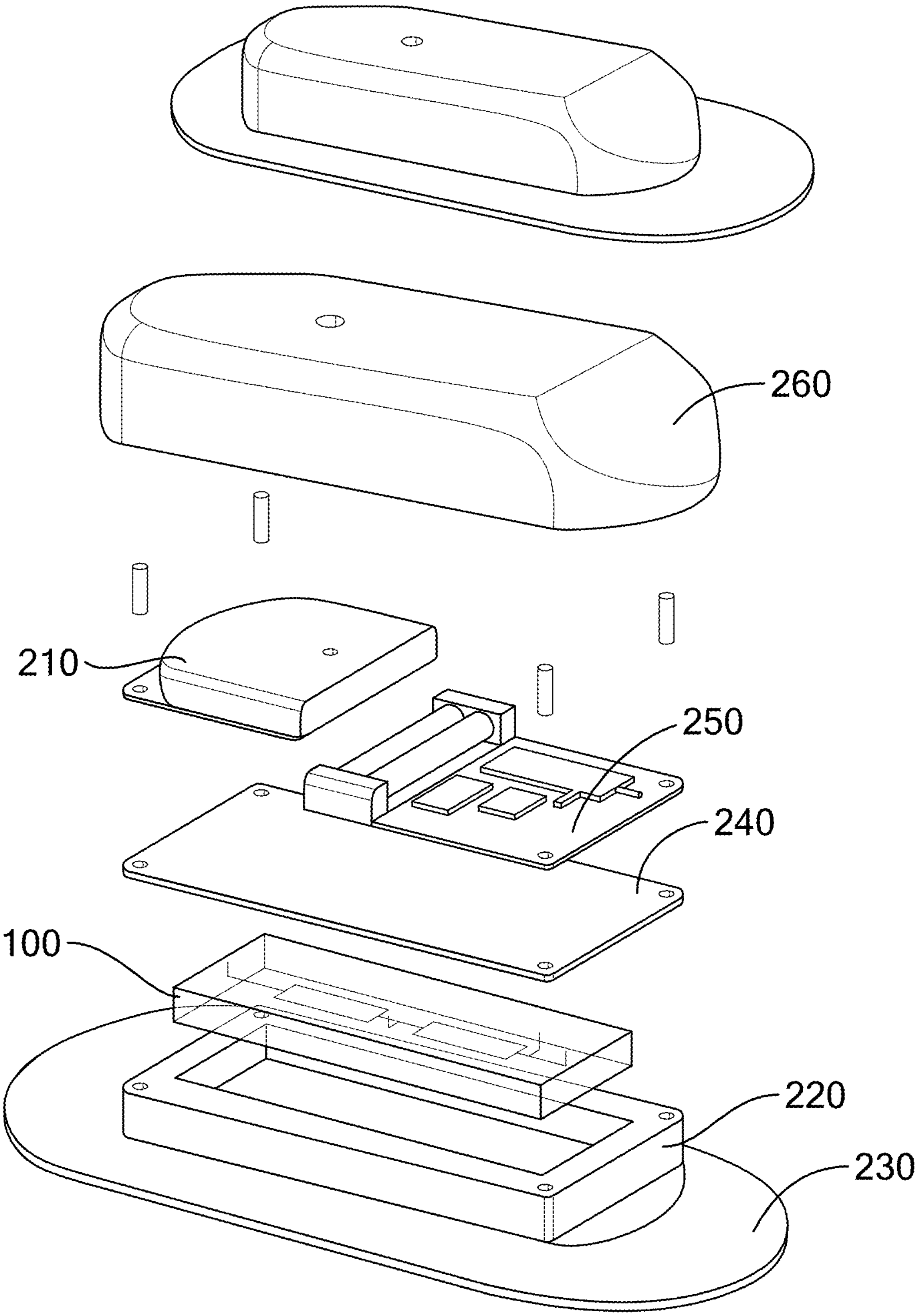
FIG. 2 is a schematic of an embodiment of a wearable system for monitoring insulin.

The system may be incorporated into a wearable apparatus to allow for real-time measurement of an analyte in a liquid sample from a subject. One such embodiment is shown in FIG. 2. Attached to the lower side of the microfluidic device (100) is a housing and reservoir (220) that is secured via an adhesive patch (230) to the patient's skin. A sample collection device (not shown) such as a microneedle or a dialysis membrane is attached to the lower side of the reservoir. On the upper side of the microfluidic device is a fluid compartment lid (240), an electronics package (e.g., including power source, microprocessor, memory, and transmitter) (250), and reagent reservoir (210). The microfluidic device and optical parts are contained within an enclosure (260).

The invention includes a binding-based method of determining the concentration of an analyte in a liquid sample. The method includes providing a microfluidic device of the invention, a liquid suspension of microspheres that are conjugated to a first analyte-binding agent, a liquid containing a labeled second analyte-binding agent, and a liquid sample suspected of containing the analyte.

The liquids may be any aqueous liquid, for example, water, an aqueous solution containing salts, buffers, stabilizers, or any other solute.

The analyte may be a chemical compound or type of molecule. For example, the molecule may be a protein, antigen, antibody, peptide, amino acid, hormone, growth factor, cytokine, cellular metabolite, nucleic acid, or oligosaccharide. The analyte may also be a cell or a component of a cell, or a microorganism or a component thereof. The molecule may be a marker for a disease or medical condition. For example, the analyte may be glucose, insulin, glucagon, TNF-α, anti-TNF-α, IL-1, or IL-21. The disease or medical condition may be cancer, diabetes, diabetic heart failure, or any other disease that produces an analyte that can be detected in a bodily fluid.

The liquid sample may be a bodily fluid from a subject. For example, the bodily fluid may be blood, plasma, serum, semen, tears, bronchial lavage, sputum, urine, saliva, spinal fluid, bile, lymph, synovial fluid, serous fluid, pleural fluid, amniotic fluid, and interstitial fluid.

The microspheres must be able to traverse readily through the channels of the microfluidic device. Therefore, the size of the microspheres for use in the method depends on the dimensions of the channels in the microfluidic device. The microspheres may have a diameter from about 1 to about 50 μm or a sub-range within that range, for example, but without limitation, from about 1 to about 5 μm, from about 5 to about 20 μm, from about 20 to about 50 μm. In some embodiments, the microspheres have an approximately uniform diameter. The microspheres may be made of a polymer, for example, polystyrene, or any other material known in the art. An analyte-binding agent, antigen-binding agent, or antigen may be conjugated to the microspheres by any method known in the art. For example, an analyte-binding agent, antigen-binding agent, or antigen may be conjugated to the microspheres by streptavidin-biotin binding or by covalent linkage. The microspheres may be made of a hydrogel that immobilizes a component of a chemical or biochemical reaction, e.g., an enzyme, but allows diffusion of other smaller molecules, e.g., diffusible agents, substrates, products, etc. For example, the microspheres may contain poly(lactic-co-glycolic acid) (PLGA), polyethylene glycol [PEG] methacrylate and acrylates, poly(acrylic acid), poly (methacrylic acid), 2-diethylaminoethylmethacrylate, 2-aminoethyl methacrylate, poly(ethylene glycol) dimethacrylates and acrylates, acrylamide/bisacrylamide, poly(2-hydroxyethyl methacrylate), methacrylated dextrans, acrylated dextrans, poly(ethylene glycol)-polyester acrylated/methacrylated block copolymer, cellulose acetate phthalate, hydroxypropyl-methyl cellulose phthalate poly(butyl methacrylate), or methyl methacrylate.

An analyte-binding agent may be a molecule or molecular complex. For example, an analyte-binding agent may be a protein, antibody, or antigen-binding fragment of an antibody.

The label may be any optically detectable label. For example, the label may be fluorescent, luminescent, colorimetric, or phosphorescent. Any fluorescent label can be used. A list of exemplary fluorescent labels is available at flowcyt.salk.cdu/fluo.html.

Figure 3:
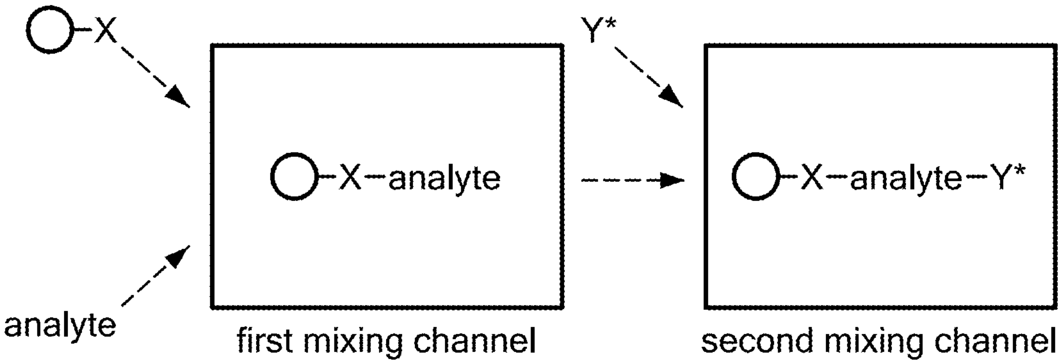
FIG. 3 is a schematic of a binding-based method of measuring an analyte in a sample using a microfluidic device. Circle represents a microsphere to which the first analyte-binding agent (X) is conjugated.

An embodiment of the method is shown in FIG. 3. The three liquid starting components are mixed in two sequential mixing steps as follows. First, the liquid suspension of conjugated microspheres is flowed into the first inlet at a first flow rate, and the liquid sample is flowed into the second inlet at a second flow rate. For the purpose of the method, the first and second inlets are interchangeable, so the inlets for the liquid suspension and the liquid sample can be reversed. The first and second flow rates allow the sample and suspension to flow in a laminar pattern in the first laminar flow channel but promote mixing of the sample and suspension in the first mixing channel. In some embodiments, the first and second flow rates are about equal. In some embodiments, the first and second flow rates are from about 1 to about 20 μl/min or any sub-range within that range. The non-laminar flow promotes mixing of the liquids and rapid binding of the analyte to the analyte-binding agent on the surface of the microspheres, resulting in formation of analyte-coated microspheres by the time the microspheres exit the first mixing channel. An analyte-coated microsphere is a microsphere on which at least a certain percentage of analyte-binding sites on the microsphere are occupied by analyte. For example, an analyte-coated microsphere may have >50%, >60%, >70%, >80%, 90%, >95%, >98%, or >99% of its analyte-binding sites occupied by analyte.

Next, the liquid containing the labeled second analyte-binding agent is flowed into the third inlet at a third flow rate. The third flow rate allows the liquid containing the labeled second analyte-binding agent and the efflux from the first mixing channel to flow in a laminar pattern in the second laminar flow channel but promotes mixing of the sample and suspension in the second mixing channel. In some embodiments, the third flow rate is about equal to the sum of the first and second flow rates. In some embodiments, the ratio of first flow rate to second flow rate to third flow rate is about 1:1:2. In some embodiments, the third flow rate is from about 1 to about 40 μl/min or any sub-range within that range. The non-laminar flow promotes mixing of the liquids and rapid binding of the labeled second analyte-binding agent to the analyte bound to the surface of the microspheres, resulting in formation of microspheres coated with labeled second analyte-binding agent by the time the microspheres exit the second mixing channel. A microsphere coated with labeled second analyte-binding agent is a microsphere on which at least a certain percentage of binding sites for labeled second analyte-binding agent on the microsphere are occupied by labeled second analyte-binding agent. For example, a microsphere coated with labeled second analyte-binding agent may have >50%, >60%, >70%, >80%, 90%, >95%, >98%, or >99% of its binding sites for second analyte-binding agent occupied by labeled second analyte-binding agent.

In both the first and second mixing channels, mixing may occur by any type of fluid flow that facilitates mixing beyond that which occurs by diffusion. For example, mixing may occur by chaotic advection, turbulent flow, or other types of non-laminar flow. An advantage of this method is that mixing in the mixing channels is driven by the flow of the liquids. Consequently, the method can be performed using continuous flow, and separate incubation and washing steps are not required. The non-laminar flow or chaotic mixing that occurs in a mixing channel of the present invention can be either passively induced, such as by the confluence of fluid streams or the channel geometry, or can be actively induced, such as by the action of microspheres, magnetic microparticles, stirrers, motors, valves, nozzles, and the like. Preferred are passive microfluidic mixers such as curved channels, serpentine channels, spiral channels, or channels incorporating any combination of curved sections and straight sections.

The method further entails detecting the amount or concentration of microsphere-bound label in the translucent detector region of the device. Microsphere-bound label refers to label that is conjugated to a molecule that is bound either directly or indirectly to a microsphere. For example only, and without limitation, a microsphere-bound label may refer to: a label conjugated to an analyte-binding agent, which is bound to an analyte, which is bound to another analyte-binding agent, which is conjugated to a microsphere; a label conjugated to an antibody, which is bound to an antigen, which is bound to an antigen-binding agent, which is conjugated to a miscrosphere; or a label conjugated to an antibody binding agent, which is bound to an antibody, which is bound to an antigen, which is conjugated to a microsphere. Other examples of microsphere bound label are possible and within the scope of the invention.

The microsphere-bound label is detected as the microspheres pass through a portion of the microfluidic device over which the translucent detector is positioned. For example, the microsphere-bound label may be detected in the second mixing channel, i.e., as the microspheres pass through the second mixing channel, or at a point between the second mixing channel and the outlet, i.e., after the microspheres have exited the second mixing channel. Microsphere-bound label may be detected at a single point or at a series of points in the microfluidic path. For example, microsphere-bound label may be detected at different points in the mixing channel to detect label on microspheres that have traveled different distances through the mixing channel. Detection may occur by capture of microscopic images of microspheres as they pass through the translucent detector region. To facilitate the capture of microscopic images, flow of liquid into the inlets may be paused or briefly stopped to slow transit of microspheres through the translucent detector region.

The label may be a fluorescent label that is detected by exposing the translucent detector region of the device to light at the excitation wavelength and sensing light emitted at the emission wavelength. The emitted light may be sensed by a photodiode, photomultiplier tube, or microscopic imaging system. When a one-dimensional light sensor, e.g., a photodiode or photomultiplier tube is used, microsphere bound label is detected by subtracting background levels of emitted from light from peak emissions due to labeled microspheres. When a microscopic imaging system is used, images are captured, scanned for fluorescent microspheres, and background levels of emitted light are subtracted from the levels emitted by fluorescent microspheres.

In the final step of the method, the concentration of the analyte is in the liquid sample is determined. In a separate assay, the method is performed using liquids containing known concentrations of analyte in place of the liquid sample. From this assay, the relationship between microsphere-bound label and analyte concentration is determined, and this relationship is used to calculate the concentration of analyte in the liquid sample by interpolation.

Figure 4:
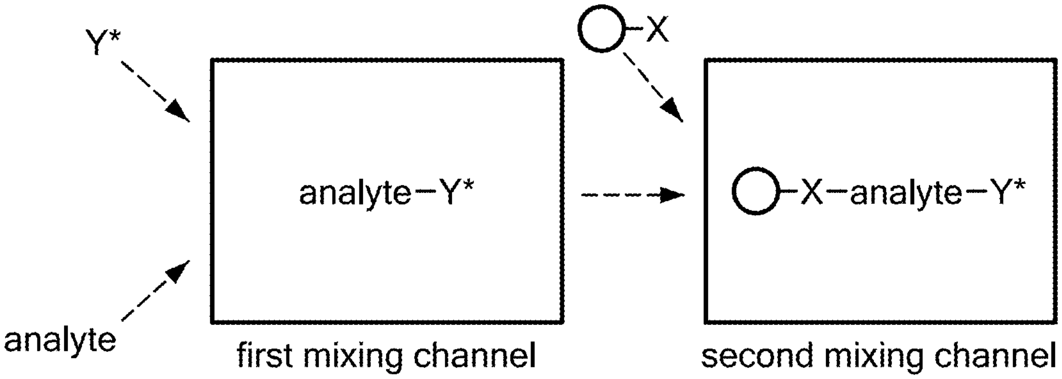
FIG. 4 is a schematic of a binding-based method of measuring an analyte in a sample using a microfluidic device. Circle represents a microsphere to which the first analyte-binding agent (X) is conjugated.

An alternative embodiment is shown in FIG. 4. In this method, the three liquid starting components are mixed in two different sequential steps as follows. First, the liquid sample is flowed into the first inlet of the device at a first flow rate, and the liquid containing the labeled second analyte-binding agent is flowed into the second inlet of the device at a second flow rate. For the purpose of the method, the first and second inlets are interchangeable, so the inlets for the liquid sample and the liquid containing the labeled second analyte-binding agent can be reversed. The first and second flow rates allow these two liquids to flow in a laminar pattern in the first laminar flow channel but promote mixing of the two liquids in the first mixing channel. In some embodiments, the first and second flow rates are about equal. In some embodiments, the first and second flow rates are from about 1 to about 20 μl/min or any sub-range within that range. The non-laminar flow promotes mixing of the liquids and rapid binding of the analyte to the labeled second analyte-binding agent, resulting in formation of complexes of analyte and labeled second analyte-binding agent by the time the analyte exits the first mixing channel.

Next, the liquid suspension of conjugated microspheres is flowed into the third inlet at a third flow rate. The third flow rate allows the liquid suspension and the efflux from the first mixing channel to flow in a laminar pattern in the second laminar flow channel but promotes mixing of the sample and suspension in the second mixing channel. In some embodiments, the third flow rate is about equal to the sum of the first and second flow rates. In some embodiments, the ratio of first flow rate to second flow rate to third flow rate is about 1:1:2. In some embodiments, the third flow rate is from about 1 to about 40 μl/min or any sub-range within that range. The non-laminar flow promotes mixing of the liquids and rapid binding of the labeled analyte complexes to the first analyte-binding agent on the surface of the microspheres, resulting in formation of microspheres coated with complexes of analyte and labeled second analyte-binding agent by the time the microspheres exit the second mixing channel. A microsphere coated with complexes of analyte and labeled second analyte-binding agent is a microsphere on which at least a certain percentage of binding sites for analyte on the microsphere are occupied by complexes of analyte and labeled second analyte-binding agent. For example, a microsphere coated with complexes of analyte and labeled second analyte-binding agent may have >50%, >60%, >70%, >80%, 90%, >95%, >98%, or >99% of binding sites for analyte occupied by complexes of analyte and labeled second analyte-binding agent.

In both the first and second mixing channels, mixing may occur by any type of fluid flow that facilitates mixing beyond that which occurs by diffusion. For example, mixing may occur by chaotic advection, turbulent flow, or other types of non-laminar flow. An advantage of this method is that mixing in the mixing channels is driven by the flow of the liquids. Consequently, the method can be performed using continuous flow, and separate incubation and washing steps are not required.

Figure 5:
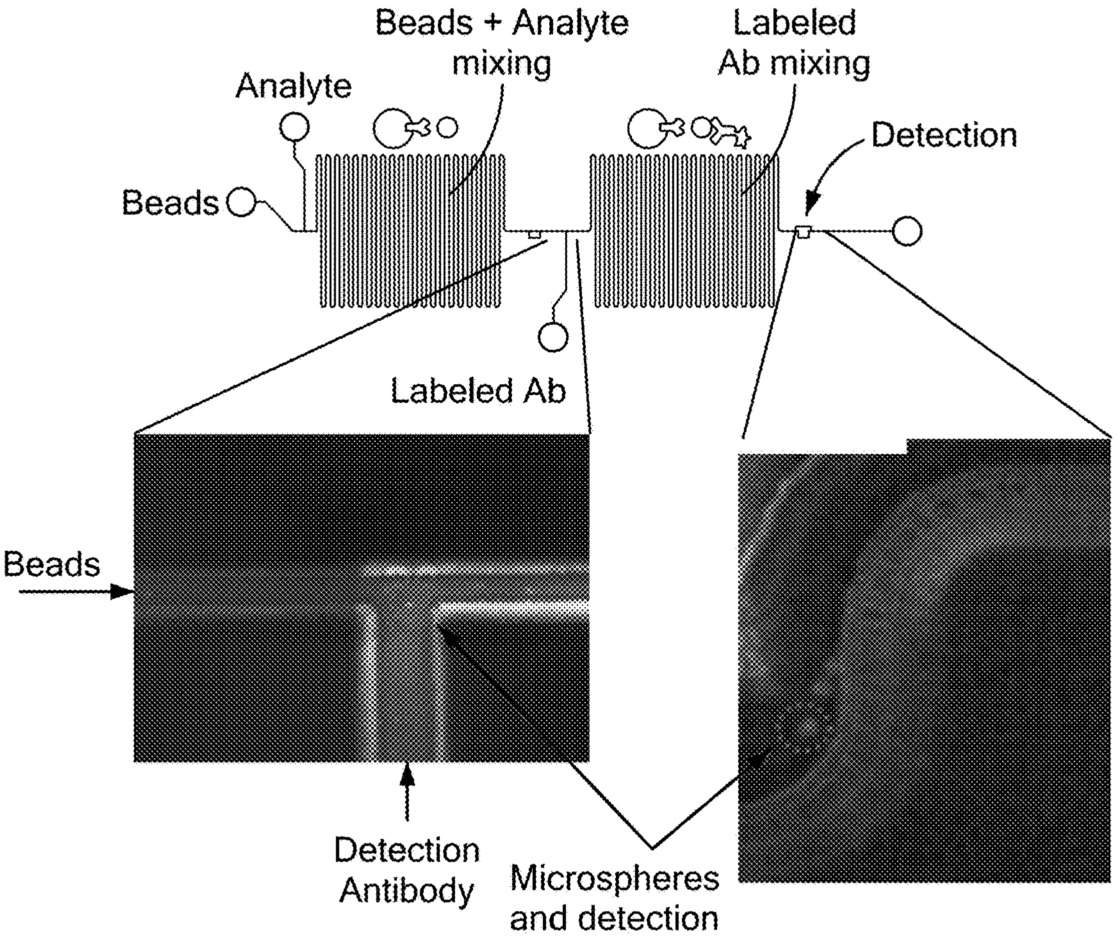
FIG. 5 shows a schematic of a microfluidic system of the invention in the upper portion of the figure. Lower panels show images of the first laminar flow channel (bottom left) and detector region (bottom right) during use of the device to detect an insulin analog secreted by primary rat hepatocytes.

An embodiment of the binding-based method of determining the concentration of an analyte in a liquid sample is illustrated in FIG. 5. A liquid sample containing the analyte is flowed into one of the first two inlets, and a suspension of microspheres ("beads") capable of binding the analyte are flowed into the other of the first two inlets. As these two liquids become mixed in the first mixing channel, the analyte is captured by the beads. A solution containing fluorescently-labeled antibody ("detection antibody") to the analyte is flowed into the third inlet. The detection antibody solution encounters the efflux from the first mixing channel in the second laminar flow channel, as shown in the lower left panel. The detection antibody solution mixes with the suspension of bead-bound analyte in the second mixing channel, and the analyte-covered beads become coated with detection antibody. The fluorescence signal from the labeled beads is measured as the microspheres pass through the detector region, as shown in the lower left panel.

The methods described above can be used to determine the concentration of two or more analytes in a liquid sample simultaneously, i.e., multiplexing. To detect two analytes, two sets of reagents are needed. For example, two populations of microspheres are needed: one population of microspheres conjugated to a first agent that binds to the first analyte, and another population of microspheres conjugated to a first agent that binds to the second analyte. These two populations are provided together in a single liquid suspension. In addition, two types of labeled second analyte-binding agents are required: a second agent that binds the first analyte and is labeled with a first label, and a second agent that binds the second analyte and is labeled with a second label. For optical detection, the first and second labels must emit light at different wavelengths, the difference in wavelengths being sufficient that the two labels can be differentiated. The first labeled second agent that binds the first analyte and the second labeled second agent that binds the second analyte are provided together in a single liquid.

For detection of multiple analytes simultaneously, the light sensor must be capable of distinguishing among different labels. For example, this could be done with a microscopic imaging system with filters that allow transmission of light of different wavelengths. For detection of two analytes as described above, a system with a rotating or alternating filter system allows the light sensor to detect microsphere-bound first label and microsphere-bound second label in alternating periods.

In a bead-based assay using a population of microspheres conjugated to an analyte-binding agent and a soluble fluorescently labeled analyte-binding agent, the microsphere-based fluorescence in the emission spectrum of the label is used to indicate the level of analyte present. In a multiplex assay for detection of multiple analytes, different populations of microspheres are conjugated to different types of analyte-binding agents, and each analyte has a unique soluble analyte-binding agent with a distinct fluorescent label. Success of multiplex assays is predicated on being able to measure the label corresponding to a given analyte on the specific population of microspheres intended to capture that analyte. One means for accomplishing this is to use particles of distinct sizes or shapes, for example, microspheres and rod-like structures. Alternatively, multiple populations of microspheres with identical physical properties can be used if the soluble analyte-binding agents show low levels of non-specific binding to microspheres. If non-specific binding is sufficiently low, it can be ascertained that the microsphere-associated fluorescence in a given emission spectrum is due solely to sandwich complexes of the targeted analyte on the population of microspheres intended to capture that analyte. To test the feasibility of this approach, a mixture of two populations of microspheres was analyzed. Microspheres in one population were conjugated to an antibody for a specific analyte, and microspheres in the other population were not conjugated to an antibody. In the presence of the analyte and another soluble fluorescently-labeled antibody to the analyte, only the first population was detected in the emission spectrum of the label.

The invention also includes a method of determining the binding affinity of an antibody for an antigen. The method includes providing a microfluidic device of the invention, a liquid suspension of microspheres that are conjugated to an antigen-binding agent, a liquid containing the antigen, and a label.

The antigen may be a molecule. For example, the molecule may be a protein, antibody, peptide, amino acid, hormone, growth factor, cytokine, cellular metabolite, nucleic acid, or oligosaccharide. The molecule may be a marker for a disease or medical condition, for example, cancer. In some embodiments of the method, the antigen can bind to the antigen-binding agent without interfering with its binding to the antibody. Thus, the epitope for the antibody is distinct from the portion of the antigen that binds the antigen binding agent. In some embodiments of the method, the antigen can be conjugated to microspheres without interfering with its binding to the antibody. Thus, the epitope for the antibody is distinct from the portion of the antigen that enables conjugation to a microsphere.

The antigen binding agent may be a molecule. For example, the molecule may be a protein, antibody, peptide, amino acid, hormone, growth factor, cytokine, cellular metabolite, nucleic acid, or oligosaccharide.

The method involves conjugating the label is to the antibody. The label may be conjugated to the antibody by any method that preserves that antigen-binding capacity of the antibody. For example, the antibody may be fused to fluorescent polypeptide by molecular cloning methods. Alternately, the antibody may be covalently cross-linked to a synthetic fluorochrome in vitro by chemical methods. Depending on the labeling method, the resulting form of the labeled antibody may be a liquid solution or a dehydrated powder. If the latter, the labeled antibody must be dissolved in a liquid.

Figure 6:
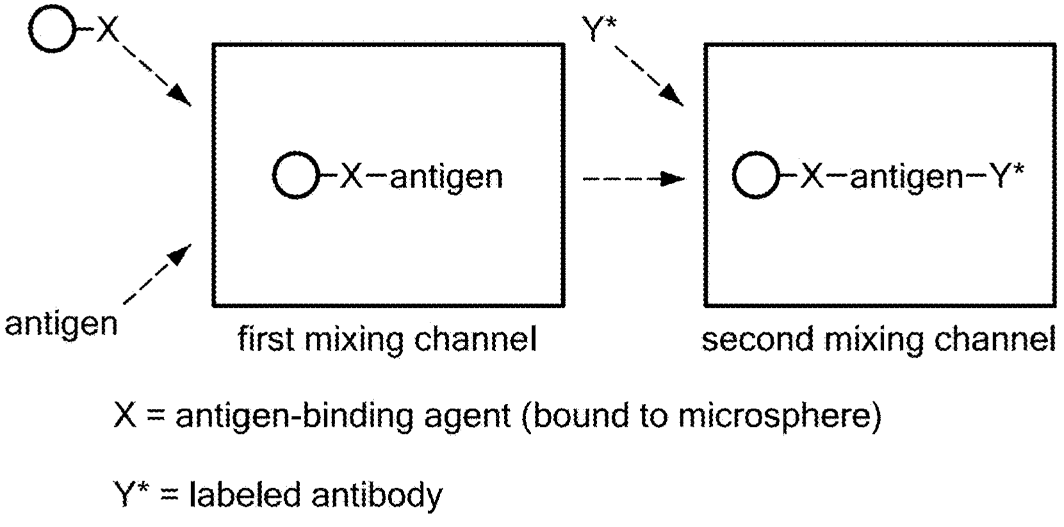
FIG. 6 is a schematic of a method of measuring the binding affinity between an antigen and antibody (Y) using a microfluidic device. Circle represents a microsphere to which an antigen-binding agent (X) is conjugated.

An embodiment of the method is shown in FIG. 6. The two liquid starting components are mixed in the first of two sequential mixing steps as follows. First, the liquid suspension of conjugated microspheres is flowed into the first inlet at a first flow rate, and the liquid containing the antigen is flowed into the second inlet at a second flow rate. For the purpose of the method, the first and second inlets are interchangeable, so the inlets for the liquid suspension and the liquid containing the antigen can be reversed. The first and second flow rates allow the liquid suspension and liquid containing the antigen to flow in a laminar pattern in the first laminar flow channel but promote mixing of the liquids in the first mixing channel. In some embodiments, the first and second flow rates are about equal. In some embodiments, the first and second flow rates are from about 1 to about 20 μl/min or any sub-range within that range. The non-laminar flow promotes mixing of the liquids and rapid binding of the antigen to the analyte on the surface of the microspheres, resulting in formation of antigen-coated microspheres by the time the microspheres exit the first mixing channel. An antigen-coated microsphere is a microsphere on which at least a certain percentage of antigen-binding sites on the microsphere are occupied by analyte. For example, an antigen-coated microsphere may have >50%, >60%, >70%, >80%, 90%, >95%, >98%, or >99% of its analyte-binding sites occupied by antigen.

Next, the liquid containing the labeled antibody is flowed into the third inlet at a third flow rate. The third flow rate allows the liquid containing the labeled antibody and the efflux from the first mixing channel to flow in a laminar pattern in the second laminar flow channel but promotes mixing of the sample and suspension in the second mixing channel. In some embodiments, the third flow rate is about equal to the sum of the first and second flow rates. In some embodiments, the ratio of first flow rate to second flow rate to third flow rate is about 1:1:2. In some embodiments, the third flow rate is from about 1 to about 40 μl/min or any sub-range within that range. The non-laminar flow promotes mixing of the liquids and rapid binding of the labeled antibody to the antigen bound to the surface of the microspheres, resulting in formation of labeled-antibody-coated microspheres by the time the microspheres exit the second mixing channel. A labeled-antibody-coated microsphere is a microsphere on which at least a certain percentage of antibody-binding sites on the microsphere are occupied by labeled antibody. For example, a labeled-antibody-coated microsphere may have >50%, >60%, >70%, >80%, 90%, >95%, >98%, or >99% of its antibody-binding sites occupied by labeled antibody.

In both the first and second mixing channels, mixing may occur by any type of fluid flow that facilitates mixing beyond that which occurs by diffusion. For example, mixing may occur by chaotic advection, turbulent flow, or other types of non-laminar flow. An advantage of this method is that mixing in the mixing channels is driven by the flow of the liquids. Consequently, the method can be performed using continuous flow, and separate incubation and washing steps are not required.

The method further entails detecting the amount of microsphere-bound label in the translucent detector region of the device. The microsphere-bound label is detected as the microspheres pass through the second mixing channel, over which the translucent detector is positioned. Microsphere-bound label is detected at different points in the mixing channel to detect label on microspheres that have traveled different distances through the mixing channel.

In the final step of the method, the binding affinity of the antibody for the antigen is determined. Based on the increase in microsphere-bound label as individual microspheres pass through the mixing channel, a person skilled in the art would be able to calculate the dissociation constant ($K_D$) from known parameters of the assay, such as antibody concentration, antigen concentration, flow rate, length of distance traveled by a given microsphere through the second mixing channel, and time interval that a given microsphere spent in contact with the labeled antibody, etc.

Figure 7:
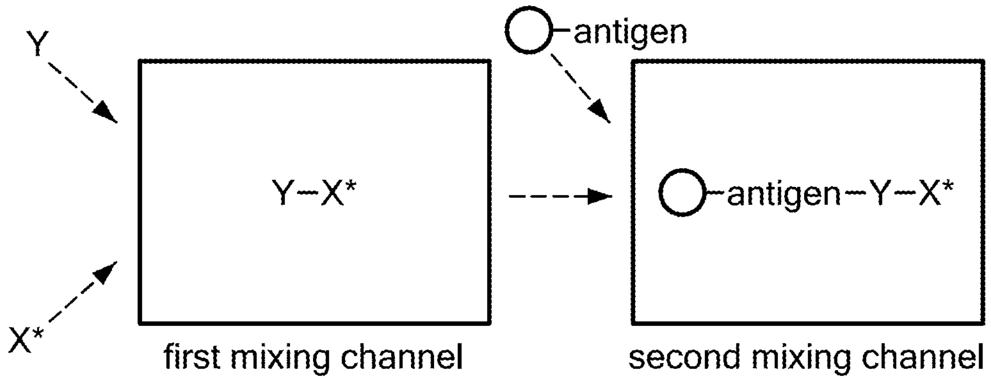
FIG. 7 is a schematic of a method of measuring the binding affinity between an antigen and antibody (Y) using a microfluidic device. Circle represents a microsphere to which the antigen is conjugated.

An alternative embodiment of determining the binding affinity of an antibody for an antigen is shown in FIG. 7. This method includes providing a microfluidic device of the invention, a liquid suspension of microspheres that are conjugated to the antigen, a liquid containing the antibody, and a liquid containing a labeled antibody-binding agent.

The antibody binding agent may be a molecule. For example, the molecule may be a protein, antibody, peptide, amino acid, hormone, growth factor, cytokine, cellular metabolite, nucleic acid, or oligosaccharide.

The three liquid starting components are mixed in two sequential mixing steps as follows. First, the liquid containing the antibody is flowed into the first inlet at a first flow rate, and the liquid containing the labeled antibody-binding agent is flowed into the second inlet at a second flow rate. For the purpose of the method, the first and second inlets are interchangeable, so the inlets for the liquid containing the antibody and the liquid containing the labeled antibody-binding agent can be reversed. The first and second flow rates allow the liquid containing the antibody and the liquid containing the labeled antibody-binding agent to flow in a laminar pattern in the first laminar flow channel but promote mixing of the liquids in the first mixing channel. In some embodiments, the first and second flow rates are about equal. In some embodiments, the first and second flow rates are from about 1 to about 20 μl/min or any sub-range within that range. The non-laminar flow promotes mixing of the liquids and rapid binding of the antibody to the labeled antibody-binding agent resulting in formation of complexes of antibody and labeled antibody-binding agent by the time the microspheres exit the first mixing channel.

Next, the liquid suspension of microspheres is flowed into the third inlet at a third flow rate. The third flow rate allows the liquid suspension and the efflux from the first mixing channel to flow in a laminar pattern in the second laminar flow channel but promotes mixing of the liquids in the second mixing channel. In some embodiments, the third flow rate is about equal to the sum of the first and second flow rates. In some embodiments, the ratio of first flow rate to second flow rate to third flow rate is about 1:1:2. In some embodiments, the third flow rate is from about 1 to about 40 μl/min or any sub-range within that range. The non-laminar flow promotes mixing of the liquids and rapid binding of the complexes of antibody and labeled antibody-binding agent to the antigen on surface of the microspheres, resulting in formation of microspheres coated with complexes of antibody and labeled antibody-binding agent by the time the microspheres exit the first mixing channel. A microsphere coated with complexes of antibody and labeled antibody-binding agent is a microsphere on which at least a certain percentage of antibody-binding sites on the microsphere are occupied by complexes of antibody and labeled antibody-binding agent. For example, a microsphere coated with complexes of antibody and labeled antibody-binding agent may have >50%, >60%, >70%, >80%, 90%, >95%, >98%, or >99% of its antibody-binding sites occupied by complexes of antibody and labeled antibody-binding agent.

In both the first and second mixing channels, mixing may occur by any type of fluid flow that facilitates mixing beyond that which occurs by diffusion. For example, mixing may occur by chaotic advection, turbulent flow, or other types of non-laminar flow. An advantage of this method is that mixing in the mixing channels is driven by the flow of the liquids. Consequently, the method can be performed using continuous flow, and separate incubation and washing steps are not required.

The method further entails detecting the microsphere-bound label in the translucent detector region of the device. The microsphere-bound label is detected as the microspheres pass through the second mixing channel, over which the translucent detector is positioned. Microsphere-bound label is detected at different points in the mixing channel to detect label on microspheres that have traveled different distances through the mixing channel.

In the final step of the method, the binding affinity of the antibody for the antigen is determined. Based on the increase in microsphere-bound label as individual microspheres pass through the mixing channel, a person skilled in the art would be able to calculate the dissociation constant ($K_D$) from known parameters of the assay, such as antibody concentration, antigen concentration, flow rate, length of distance traveled by a given microsphere through the second mixing channel, and time interval that a given microsphere spent in contact with complexes of antibody and labeled antibody-binding agent, etc.

The invention also includes an enzyme-based method of determining the concentration of an analyte in a liquid sample that does not require analyte-binding agents. The method entails providing a microfluidic device of the invention, a liquid suspension of microspheres that contain a first enzyme capable of converting an indicator precursor into an indicator in the presence of a diffusible agent, a liquid containing a second enzyme capable of producing the diffusible agent in the presence of the analyte, and a liquid sample suspected of containing the analyte.

Figure 8:
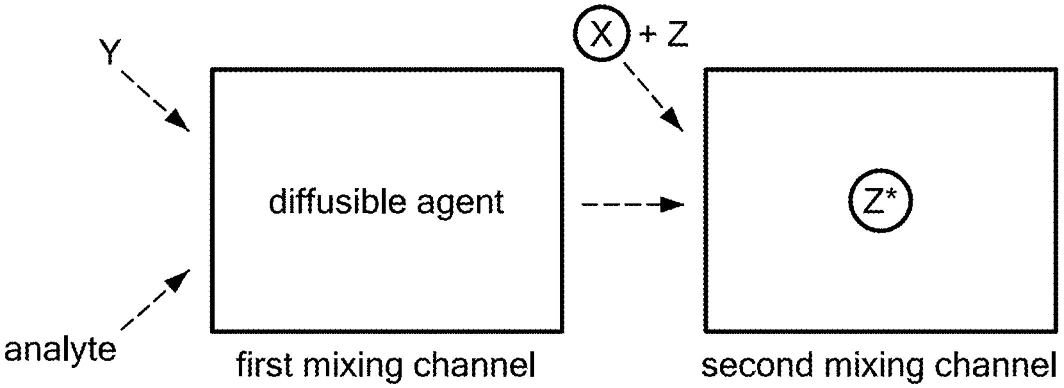
FIG. 8 is a schematic of a method of enzyme-based measuring an analyte in a sample using a microfluidic device of the invention. Circle represents a microsphere in which the first enzyme (X) is trapped.
Figure 9:
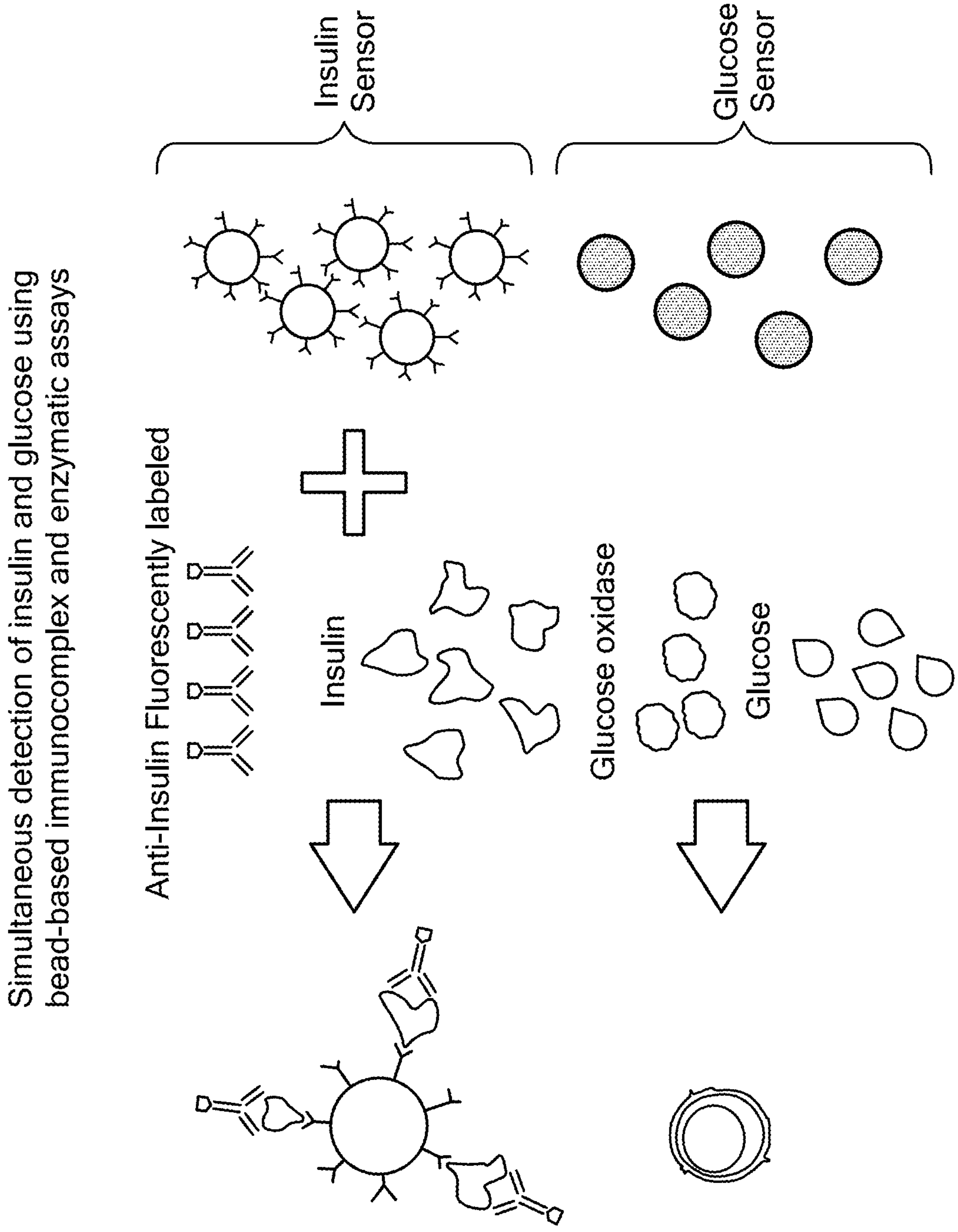
FIG. 9 is a schematic illustrating the simultaneous detection of insulin and glucose using microsphere-based immunocomplex and enzymatic assays, respectively. In the upper portion of the figure, a first population of microspheres conjugated to a first anti-insulin antibody binds to insulin, which is then bound by a second, fluorescently-labeled anti-insulin antibody. In the lower portion of the figure, a second population of microspheres containing a trapped horseradish peroxidase is exposed to a solution containing glucose, glucose oxidase, and Amplex Red (not shown). The $H_2O_2$ generated by glucose oxidase is used by horseradish peroxidase to convert Amplex Red into its fluorescent form. The two populations of labeled microspheres can be identified by the distinct fluorescence emissions.

An embodiment of the method is shown in FIG. 8. In this method, the three liquid starting components are mixed in two sequential mixing steps as follows. First, the liquid sample is flowed into the first inlet at a first flow rate, and the liquid containing the second enzyme is flowed into the second inlet at a second flow rate. For the purpose of the method, the first and second inlets are interchangeable, so the inlets for the liquid sample and liquid containing the second enzyme can be reversed. The first and second flow rates allow the sample and enzyme to flow in a laminar pattern in the first laminar flow channel but promote mixing of the sample and enzyme in the first mixing channel. In some embodiments, the first and second flow rates are about equal. In some embodiments, the first and second flow rates are from about 1 to about 20 μl/min or any sub-range within that range. The non-laminar flow promotes mixing of the liquids and production of the diffusible agent by the second enzyme by the time the microspheres liquids exit the first mixing channel.

Next, the liquid suspension of microspheres is flowed into the third inlet at a third flow rate. The third flow rate allows the liquid suspension of microspheres and the efflux from the first mixing channel to flow in a laminar pattern in the second laminar flow channel but promotes mixing of the sample and suspension of microspheres in the second mixing channel. In some embodiments, the third flow rate is about equal to the sum of the first and second flow rates. In some embodiments, the ratio of first flow rate to second flow rate to third flow rate is about 1:1:2. In some embodiments, the third flow rate is from about 1 to about 40 μl/min or any sub-range within that range. The non-laminar flow promotes mixing of the liquids and conversion of the indicator precursor into the indicator by the time the microspheres exit the second mixing channel.

In both the first and second mixing channels, mixing may occur by any type of fluid flow that facilitates mixing beyond that which occurs by diffusion. For example, mixing may occur by chaotic advection, turbulent flow, or other types of non-laminar flow. An advantage of this method is that mixing in the mixing channels is driven by the flow of the liquids. Consequently, the method can be performed using continuous flow, and separate incubation and washing steps are not required.

The method further entails detecting the amount of indicator associated with the microspheres, Microsphere-associated indicator refers to indicator that is coincident with a microsphere in optical detection methods.

The microsphere-associated indicator is detected as the microspheres pass through a portion of the microfluidic device over which the translucent detector is positioned. For example, the microsphere-associated indicator may be detected in the second mixing channel, i.e., as the microspheres pass through the second mixing channel, or at a point between the second mixing channel and the outlet, i.e., after the microspheres have exited the second mixing channel. Microsphere-associated indicator may be detected at a single point or at a series of points in the microfluidic path. For example, microsphere-associated indicator may be detected at different points in the mixing channel to detect indicator on microspheres that have traveled different distances through the mixing channel.

The indicator may be a fluorescent molecule that is detected by exposing the translucent detector region of the device to light at the excitation wavelength and sensing light emitted at the emission wavelength. The emitted light may be sensed by a photodiode, photomultiplier tube, or microscopic imaging system. When a one-dimensional light sensor, e.g., a photodiode or photomultiplier tube is used, microsphere-associated indicator is detected by subtracting background levels of emitted from light from peak emissions due to labeled microspheres. When a microscopic imaging system is used, images are captured, scanned for fluorescent microspheres, and background levels of emitted light are subtracted from the levels emitted by fluorescent microspheres.

In the final step of the method, the concentration of the analyte is in the liquid sample is determined. In a separate assay, the method is performed using liquids containing known concentrations of analyte in place of the liquid sample. From this assay, the relationship between microsphere-associated indicator and analyte concentration is determined, and this relationship is used to calculate the concentration of analyte in the liquid sample by interpolation.

An indicator may be any molecule that can be detected by optical methods. For example, the indicator may be fluorescent, luminescent, colorimetric, or phosphorescent. For example, the indicator may be 10-Acetyl-3,7-dihydroxyphenoxazine. An indicator precursor is any molecule that may be converted to an indicator by a reaction or series of reactions catalyzed by an enzyme. Consequently, each indicator precursor corresponds to an indicator.

The diffusible agent may be any diffusible, water-soluble molecule that can be a reagent in the reaction catalyzed by the first enzyme and a product in the reaction catalyzed by the second enzyme. For example, the diffusible agent may be $H_2O_2$ or another chemical agent that can serve as substrate for the first enzyme.

The first enzyme may be any enzyme that catalyzes a reaction in which a diffusible agent and an indicator precursor are substrates and an indicator is the product. For example, the enzyme may be horseradish peroxidase.

The second enzyme may be any enzyme that catalyzes a reaction in which an analyte is a substrate and a diffusible agent is the product. For example, the second enzyme may be glucose oxidase.

The invention includes a kit for determining the concentration of an analyte in a liquid, the kits containing a microfluidic device of the invention, microspheres conjugated to a first analyte-binding agent, and a labeled second antibody binding agent. The kit may also include instruction for performing one or more methods of the invention.

The invention includes a kit for measuring binding of an antibody to an antigen. The kit may contain a microfluidic device of the invention, microspheres of conjugated to an antigen binding agent, and the antigen. Alternatively, the kit may contain a microfluidic device of the invention, microspheres conjugated to the antigen, and a labeled antibody binding agent. The kit may also include instructions for performing one or more methods of the invention.

The invention also encompasses multiplexing methods in which at least one analyte is detecting by analyte-binding agents as described above and at least one analyte is detected by an enzymatic method as described above. An embodiment of such a method is illustrated in FIG. X. In this embodiment, glucose is detected enzymatically, and insulin is detected by binding agents, e.g., antibodies. In one embodiment, a sample suspected of containing insulin and glucose is flowed into the first inlet of a microfluidic device of the invention, and a liquid suspension containing glucose oxidase and microspheres conjugated to anti-insulin antibodies is flowed into the second inlet. In the first mixing channel, insulin is captured by the microspheres, and glucose oxidase catalyzes the formation of $H_2O_2$. A suspension containing a fluorescently-labeled second anti-insulin antibody, Amplex Red, and microspheres containing trapped horseradish peroxidease is flowed into the third inlet. In the second mixing channel, the fluorescently labeled anti-insulin antibody binds to the population of microspheres that have captured insulin, and horseradish peroxidase uses $H_2O_2$ to convert Amplex Red into its fluorescent form. Fluorescence from the insulin-binding microspheres is detected at one wavelength, and fluorescence from the enzyme-containing microspheres is detected at another wavelength.

In an alternate embodiment, a sample suspected of containing insulin and glucose is flowed into the first inlet of a microfluidic device of the invention, and a solution containing glucose oxidase and a soluble, fluorescently-labeled anti-insulin antibody is flowed into the second inlet. In the first mixing channel, insulin is bound by the fluorescently-labeled antibody, and glucose oxidase catalyzes the formation of $H_2O_2$. A suspension containing Amplex red, a population of microspheres conjugated to a different anti-insulin antibody, and another population of microspheres containing trapped horseradish peroxidease is flowed into the third inlet. In the second mixing channel, the microspheres conjugated to the anti-insulin antibody capture the complexes of insulin and fluorescently-labeled anti-insulin antibody, and horseradish peroxidase uses $H_2O_2$ to convert Amplex Red into its fluorescent form. Fluorescence from the insulin-binding microspheres is detected at one wavelength, and fluorescence from the enzyme-containing microspheres is detected at another wavelength.

EXAMPLES

Example 1: Materials and Methods

Microfluidic device fabrication. The polydimethylsiloxane (PDMS) microfluidic device was fabricated using well-established soft lithography method. Negative photo resist SU-8 2100 (MicroChem, Newton, MA) was spin-coated on Silicon wafers to a thickness of 150 μm, and patterned by exposure to UV light through a transparency photomask (CAD/Art Services, USA). PDMS (Sylgard 184, Dow Corning, MI) was mixed with the crosslinker (Sylgard 184 curing agent) in a ratio of 10:1, poured onto the photoresist patterns, degassed thoroughly and cured for 12 hours at 65° C. Next, the PDMS was peeled off the wafer and placed in oxygen-plasma chamber in order to bond with the glass slide. The device consisted of three inlets and two mixing channels. Tygon Micro Bore PVC Tubing 0.010" ID, 0.030" OD, 0.010" Wall (Small Parts Inc., FL, USA) was connected to the channels and to 1 mL syringes. Syringe pumps (Harvard Apparatus, USA) were used to maintain a flow rate of 5 μL/min through the device.

Microfluidic flow chambers were fabricated using soft lithography. Negative photo resist SU-8 2100 (MicroChem, Newton, MA) was deposited onto clean silicon wafers to a thickness of 150 μm, and patterned by exposure to UV light through a transparency photomask (CAD/Art Services, Bandon, OR). The Sylgard 184 poly(dimethylsiloxane) (PDMS) (Dow Corning, Midland, MI) was mixed with crosslinker (ratio 10:1), poured onto the photoresist patterns, degassed thoroughly and cured for 12 hours at 65° C. Next, the PDMS devices were peeled off the wafer and bonded to glass slides after oxygen-plasma activation of both surfaces. The device consisted of 3 inlets and 2 serpentine mixing regions. Prior to the experiments the microfluidic channels were treated with 0.25% pluronic acid F-127 (by filling the channels with the solution and then flushing them with PBS and air). Tygon Micro Bore PVC Tubing 100f, 0.010" ID, 0.030" OD, 0.010" Wall (Small Parts Inc, FL, USA) were connected to the channels and to the syringes. Syringe pumps (Harvard Apparatus, USA) were used to control the flow of solutions through the device.

Monoclonal antibodies. Hybridomas producing monoclonal antibodies HTB-124 and HTB-125 against human insulin were obtained from the ATCC hybridoma bank. Immunoglobulin production was performed by Precision Antibody (Columbia, MD). Both antibodies are from the IgG sub-class. They were purified from hybridoma supernatants using protein G columns (Precision Antibody, Inc., Columbia, MD) and stored at 4° C. in PBS. Both antibodies have high affinity for regular human insulin with $K_d$ of $2\times10^{-8}$ and $3\times10^{-9}$ for HTB-124 and HTB-125, respectively Assay procedure. The microsphere assay was performed at room temperature. Conjugated microsphere (30 μl, 0.5 μg/μl) and 30 μl of target insulin analyte were mixed and shaken for 30 min. Thereafter, the secondary labeled immunoglobulin was added to a final concentration of 1 μg/ml. The microcentrifuge tube, protected from light, was shaken for an additional 30 minutes and then the beads were washed twice with 60 μl PBS.

Heat-treated human serum. Human serum was heated in a thermostat water bath at 60° C. for 1 hour to destroy endogenous insulin. All insulin calibrators were prepared and diluted in the heat treated serum.

MSD SULFO-TAG ag, HTB124 conjugation. HTB-124 clone ~1 mg/mL was used for SULFO-TAG NHS-Ester conjugation per vendor's protocol (Meso discovery). HTB-124 antibody solution was buffer-exchanged using ZEBA spin desalting columns 40KMWCO (-Thermo Scientific) into sodium azide-free PBS. SULFO-TAG Ester was combined with the protein solution according to the desired molar coupling ratio (MCR) of 20:1. The solution was incubated for two hours at room temperature protected from light, with gentle shaking to ensure complete mixing. The SULFO-TAG HTB-124 was buffer exchanged into PBS. The final conjugated protein concentration was determined by Nano Drop Thermo Scientific.

Detection of Insulin in Meso scale technology (MSD). MSD technology employs electrochemiluminescence detection in immunoassay. The MSD plates contained built-in electrodes at the bottom of each well. Upon electrochemical stimulation initiated at the electrode surface of the plates, the detection antibody labeled with SULFO-TAG (Ruthenium-sulfotris-bipyridine NHS ester) emitted light which was measured through a CCD camera in MSD SECTOR Imager 2400. 96-well MSD plates were coated with 30 μl of mAb HTB-125 (4 μg/ml) of capture antibody. After an overnight incubation at 2-8° C., plates were blocked with blocking buffer, 150 μl were added to each well for 1 h at room temperature with agitation. Plates were washed three times with PBS-T (pH 7). 25 μl of samples containing insulin were added for 2 hours at room temperature in triplicates final concentration ranging from 390 pg/ml-100 ng/ml to allow specific binding to HTB-125 antibody clone. Control wells lacked insulin. After 2 h of incubation at room temperature with agitation the plates were washed three times PBS-T (pH 7). Then detection antibody (HTB-124, 1 μg/ml SULFO-TAG conjugated) diluted in PBS was added, followed by the addition of 25 μl per well. After 1 h of incubation at room temperature with agitation. The plates were washed and aspirated three times. 150 μl of MSD Read Buffer were added to each well. The plates were read by the MSD SECTOR Imager 2400. Unless stated elsewhere, triplicate data points were collected for samples and standards to ensure data accuracy.

Reference measurements. Reference insulin measurements were performed with the Architect insulin assay (Abbott Laboratories, Green Oaks, IL), which uses chemiluminescent microparticle immunoassay (CMIA) technology.

Source of human plasma samples containing regular human insulin and insulin aspart. To evaluate the immunoassays' clinical performance, stored plasma samples were tested. Samples containing regular human insulin measurements were collected at intervals after a non-diabetic volunteer consumed a meal containing 69 g of carbohydrates at 12:00 PM. Samples containing insulin aspart were collected at intervals after a fasting volunteer with type 1 received a 5 unit bolus of insulin aspart along with a small breakfast meal. The clinicaltrials.gov number for the study is NCT00811317.

Preparation of insulin standards. Purified regular human insulin (zinc human insulin crystals, a gift from Eli Lilly and Company, Indianapolis, IN), insulin lispro powder (a gift from Eli Lilly), or insulin aspart powder (a gift from Novo Nordisk, Bagsværd, Denmark) were diluted in 0.1 M HCl to a concentration of 1 mg/ml. This stock was then diluted in a heat inactivated human pool of serum to a concentration of 0.1 mg/ml. Serial dilutions of these stock solutions were then performed in 1% (w/v) blocking buffer to produce sets of standards.

Microsphere sensor preparation. For anti-TNF-α antibody detection Biotinylated human TNF-α protein (ACRO Biosystem, Cat. No. TNA-H8\211) was conjugated to streptavidin-coated polystyrene microsphere of diameter 6.8 μm (0.5% w/v, Spherotech Inc.). A 50 μL aliquot of the microsphere solution was washed with 1× Phosphate Buffered Saline (PBS) (Sigma, USA) and diluted to a final concentration of 0.25 mg/ml in PBS with 0.005% (v/v) Tween 20 (Sigma, USA). 40 μg of human TNF-α Protein was added per mg of microspheres, and the mixture was shaken at room temperature (RT) for 120 min. Unbound active sites were blocked with BlockAid (B-10710, Invitrogen) for 1 hour. Finally, the microspheres were washed with PBS and stored at 4° C. in 0.5% (w/v) Bovine Serum Albumin (BSA) (Sigma, USA) in PBS. The analyte for dose response experiments, mouse monoclonal antibody to human TNF-α (Sino Biological Inc., USA, Cat. No. 10602-MM01), was diluted to the following concentrations in 1×PBS: 100, 250, 500, 750, 1000 ng/ml. The detection antibody, goat anti-mouse IgG-FITC (Sigma, USA, Cat. No. F 0257) was mixed with Pierce Immunostain Enhancer (Thermo Scientific, USA) to obtain a final concentration of 13.8 μg/ml.

For TNF-α detection, a 200 μL (1 mg) aliquot of Protein G polystyrene microspheres (0.5% w/v, Spherotech Inc.) was washed with 800 μL of PBS and centrifuged. 200 μL of rabbit anti-human TNF-α (Thermo Scientific, USA, Cat. No. P300A) was diluted with 100 μL of 0.5% BSA/PBS (0.22 mg) and was added to the microspheres. The mixture was shaken at RT for 120 min. Unbound active sites were blocked with 1 mL of BlockAid for 1 hour. Finally, the microspheres were washed with PBS and stored at 4° C. in 0.5% (w/v) BSA/PBS. For dose response experiments *E. coli*-derived recombinant rat TNF-α (R&D Systems, USA, Cat. No. AGM0213082) and was diluted to the following concentrations in 1×PBS: 0.02, 1, 50, 100, 1000 ng/mL. The hamster anti-TNF-α FITC (eBioscience, USA, Cat. No. 11-7423) was diluted in Pierce Immunostain Enhancer to a final concentration of 13.8 μg/ml.

Antibody HTB-125 was biotinylated with EZ-Link NHS-PEG4-Biotin (Thermo Scientific, USA) according to the manufacturer's protocol and diluted to a final concentration of 0.5 mg/ml in PBS with 0.005% (w/v) Tween-20 (Sigma, USA). The purified antibody was applied to streptavidin conjugated polystyrene microsphere (Bangs Laboratories, Inc. Fishers, IN), at a ratio of 20 μg of IgG per mg particles, and the mixture was shaken at RT for 90 min. Unbound active sites were blocked with BlockAid (B-10710, Invitrogen, USA) for one hour. Finally, the microspheres were washed in PBS (Sigma, USA) with 0.5% (w/v) BSA (Sigma, USA), diluted to a final concentration of 0.5 mg/ml, and stored at 4° C. Antibody HTB-124 was labeled with Alexa Fluor 488 (Invitrogen, USA) according to the manufacturer's protocol and stored at 4° C.

Data and image analysis. The fluorescent microspheres for detection of the analytes were assessed and recorded using Zeiss Axio Observer.ZI Microscope (Zeiss, Germany). Images were taken with Hamamatsu digital camera C10600 Orca-R2 using the ZEN pro 2012 software (blue edition). ImageJ software was used for image analysis and processing. The microsphere of interest was selected and outlined, and the area, integrated density, and mean gray value were measured. The background fluorescence was selected as a random circular region in the microfluidic channels, near the fluorescent microsphere. At least thirty fluorescent microspheres were analyzed for each sample. Microsoft Office Excel 2010 and Origin were applied for statistical analyses.

Fluorescence images were captured on a Zeiss 200 Axiovert microscope using an AxioCAM MRm digital camera and AxioVision 4.8 software from samples based on AlexaFluor488 fluorescence (excitation 494 nm/emission 519 nm). In microfluidic experiments the flow through of the microfluidic device was temporarily halted during image acquisition. However, is the digital camera is sufficiently fast, it is not necessary to stop flow in order to record an image.

ImageJ and Matlab software were used for the image processing and quantification of fluorescence associated with microspheres. Each image was divided into 4 sub-images and the fluorescence associated with the microsphere was measured using an algorithm using the following steps:

1. Divide each image into 4 sub-images.
2. Subtract from each pixel in the image the median signal for the whole image (background).
3. Calculate the standard deviation of the remaining signal.
4. Consider each pixel with intensity larger than 1.3 times the STD as signal above background.
5. Find connectivity components of pixels ('clusters').
6. Define beads as clusters with the area between 60 and 350 pixels.
7. Sum the intensity of all beads in each image and divide by the number of beads to calculate the mean intensity per bead.

For some images, the edges of the images were cropped to remove areas of poor image quality before processing.

A calibration curve was derived using a range of insulin or insulin analogs concentrations ranging from 500 pg/ml-100 ng/ml (86 pM-17200 pM) and generated using a regression model with Origin Pro 8 (OriginLab Corporation, Northampton, MA). The detection limit of the assay was defined as the concentration of the analyte that gives a response that is higher than three standard deviations above the signal from PBS spiked into heat inactivated human serum. The regression model was applied using the log-log transformed data using an equation of the form y=B+A(x), where x is the dilution of the insulin calibrator and y is the corresponding response signal obtained.

Binding kinetics model. The following section describes the supporting equations for non-well mixed solutions that were amended in the developed theoretical model on reaction kinetics in the well-mixed LOC describe in the results section. The general conservation equation that describes the reaction in the fluid bulk appears in (Gervais et al., 2006):

$$\partial C/\partial t+\nabla(-D\nabla C+vC)=R_v \tag{1}$$

where C is the bulk concentration of an analyte, D is the bulk analyte diffusivity, and v is the analyte fully developed velocity profile of in the bulk. Rv is the analyte creation volumetric rate. The initial condition for the analyte concentration in the bulk is:

$$C(t=0)=C_0 \tag{2}$$

The conservation equation for the detecting surface that includes the surface diffusion and the reaction rate for the formation of the absorbed analyte appears in Eq. 3:

$$\partial C_s/\partial t+\nabla(-D_s\nabla C_s)=k_{on}C_{(n=0)}(C_{s0}-C_s)-k_{off}C_s \tag{3}$$

where $C_s$ is the surface concentration of an analyte, Ds is the analyte surface diffusivity $C_{(n=0)}$ is the concentration of bulk analyte near the reactive bead wall, $C_{s0}$ is the total number of the binding sites, $k_{on}$ is the association rate constant and $k_{off}$ is the dissociation rate constant of the binding reaction.

The initial condition for Eq. 3 is the concentration of the absorbed species on the detecting surface at the beginning of the process is:

$$C_s(t=0)=0 \tag{4}$$

Eqs. 1 and 3 are coupled through the flux balance boundary condition on the reacting surface as follows:

$$n(-D\nabla C+vC)=-k_{on}C_{(n=0)}(C_{s0}-C_s)+k_{off}C_s \tag{5}$$

where n is the surface vector. The additional boundary condition on non-reactant surfaces is insulation:

$$n(-D_s\nabla C_s)=0 \tag{6}$$

Previously, Kankare and Vinokurov (1999) developed the mathematical model that describes reaction kinetics in standard, non-mixed immunosorbent reactions, where absorption occurs on spherical surfaces. To solve the general conservation equation for the reaction in the fluid bulk (Eqs. 2-8), the authors used the following assumptions: 1) reaction takes place in the not agitating solution; therefore, v=0; 2) no reagents are formed in the bulk; therefore, $R_v$=0; 3) no surface diffusivity of the absorbed analyte; thus, $D_s$=0; and 4) constant diffusivity of the analyte in the liquid (D=const.) (Kankare and Vinokurov, 1999). This model was followed to calculate the reaction time (th) on microsphere in the not-agitating solution.

According to Kankare and Vinokurov (1999) Eqs. 7-13 describe the analyte absorption on the spherical microsphere in the non-mixed immunosorbent reaction.

$$\partial C/\partial t-D\left(d^2/dn^2\right)-2D/(n+R)\cdot\partial c/\partial n=0 \tag{7}$$

where R is the detection microsphere radius.

The initial condition for the analyte concentration in the bulk is:

$$C(t=0)=C_0 \tag{8}$$

The surface reaction equation is:

$$\partial C_s/\partial t=k_{on}C_{(n=R)}(C_{s0}-C_s)-k_{off}C_s \tag{9}$$

with initial condition:

$$C_s(t=0)=0 \tag{10}$$

The coupling boundary condition is:

$$n(-D\nabla C)=-k_{on}C_{(n=0)}(C_{s0}-C_s)+k_{off}C_s \tag{11}$$

The numerical solution of this set of equations shows that the time to achieve full surface coverage of the analyte on the microsphere surface (equilibrium) in non-mixed solution is infinity. Therefore, an important outcome from this numerical solution for non-mixed solutions is the approximation for the time needed for the reaction to achieve a certain deviation from the equilibrium coverage (h) on the spherical microsphere:

$$\lim_{k_{on}\to\infty} RS \approx -(Rk_{off}C_{s0})/(k_{off}D(1+k_{on}/k_{off}\cdot C_0)^2)\ln h \tag{12}$$

where h is the deviation from the equilibrium coverage:

$$h=(C_{s0}-C_s)/C_{s0} \tag{13}$$

The solution of these equations implies that in microsphere-based immunosorbent assay, in the non-mixed solutions, the binding reaction rates for reagents with low binding equilibrium constant depend on diffusion, and further increase of the reaction surface or the decrease of reaction volumes will not decrease the reaction time (Kusnezow et al. 2006).

The LOC methods and devices described herein were used for measuring Tumor Necrosis Factor (TNF)-α cytokine and TNF-α inhibitor, anti-TNF-α antibody in a sample.

Example 2: Flow Dynamics in a Microfluidic Device

FIGS. 1A-1C schematically illustrates the developed flow-through LOC device. The device consisted of three inlets and two mixing regions. The inlets were connected with syringe pumps that were operated individually to obtain desired flow rates for the detection of microspheres downstream. First, a solution containing the analyte molecules was introduced into inlet 1 (110) and mixed with a suspension of functionalized microspheres that were introduced via inlet 2 (120) to capture the target analyte in the first mixing channel (140) (FIGS. 1A-1C). The specific interaction that occurs between the conjugated microspheres and the target analyte in the first mixing channel leads to the analyte recognition and capture. A detection (reporter) antibody against the analyte, conjugated with a specific fluorophore, was then introduced to the flow stream via inlet 3 (150) just before the second mixing channel (170). The sandwich complex formation, composed of microsphere sensor-analyte-reporter antibody, resulted in high levels of intensity fluorescent signal on the microsphere that was easily distinguishable from the background intensity. The fluorescence from the reporter antibodies was detected downstream to the second mixing channel (180).

Figure 11A:
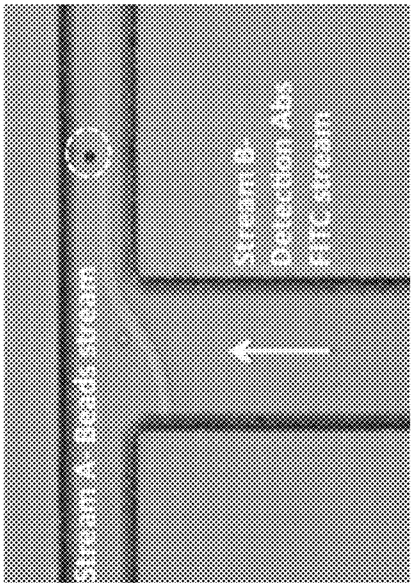
FIG. 11A is a phase contrast image of the second laminar flow channel adjacent to inlet three in an embodiment of a device of the invention.
Figure 11B:
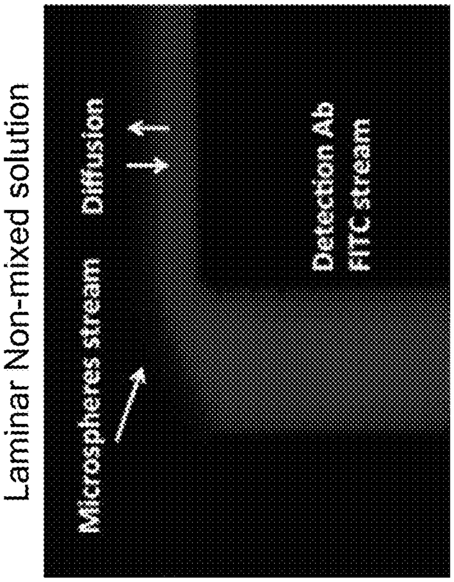
FIG. 11B is a fluorescence image of the second laminar flow channel adjacent to inlet three in an embodiment of a device of the invention.
Figure 11C:
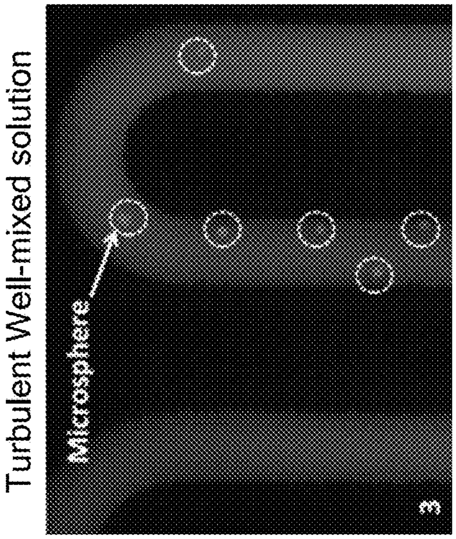
FIG. 11C is a fluorescence image of the second mixing channel in an embodiment of the device of the invention. Labeled microspheres are circled.

The flow profile in the developed microfluidic device consisted of laminar flow and non-laminar flow profiles in distinct regions of the device. Laminar flow in the developed LOC occurs when a fluid streams A and B flow in parallel layers, with no disruption between the layers (FIGS. 11A and 11B). As observed in FIG. 11A, the microsphere in stream A moved in straight lines parallel to the channel wall. In fluid dynamics, laminar flow is characterized by high momentum diffusion and low momentum convection (Batchelor, 2000; Bayraktar and Pidugu, 2006; Beebe et al. 2002). Thus, in this region the microsphere adsorption kinetics are controlled by diffusion rates between upper stream A to the lower stream B and vice versa and thus will follow a non-mixed immunoassay reaction such as describe in ELISA (Kankare, J.; Vinokurov, 1999). The fluid flow is altered markedly when it travels over an abrupt serpentine feature just as wind going over a mountain ridgeline (FIG. 11C) (Sharp and Adrian 2004). The narrowing U shape serpentine geometry causes a change in the flow profile from diffusion-controlled laminar profile to well-mixed solution in the incubation channels. FIG. 11C shows the instantaneous position of the microspheres in the carrier fluid in the well-mixed incubation channel. It was apparent that the particles were distributed in a highly nonhomogeneous manner in the incubation channel, forming clusters and voids as well as spontaneously segregating different regions of the flow in the channel. Thus, individual microspheres followed paths that were independent and largely random in this non-laminar fluid stream. Next, the detection antibody, FITC-labeled anti-mouse IgG, was introduced into inlet 3. The fluorescent signal on the microsphere sensor, generated by the conjugation of the captured anti-TNF-α antibody with the fluorescently labeled detection antibody, is demonstrated in FIG. 11C. The high surface-to-volume ratio of the microsphere (Lim et al., 2007), as well as the mixing (Sharp and Adrian 2004)) generated within the serpentine structure of the microfluidic device, reduced the incubation time for the detection to seconds, thereby enabling continuous flow-through detection.

Example 3: Anti-TNF-α Antibody Immunoassay

Figure 12A:
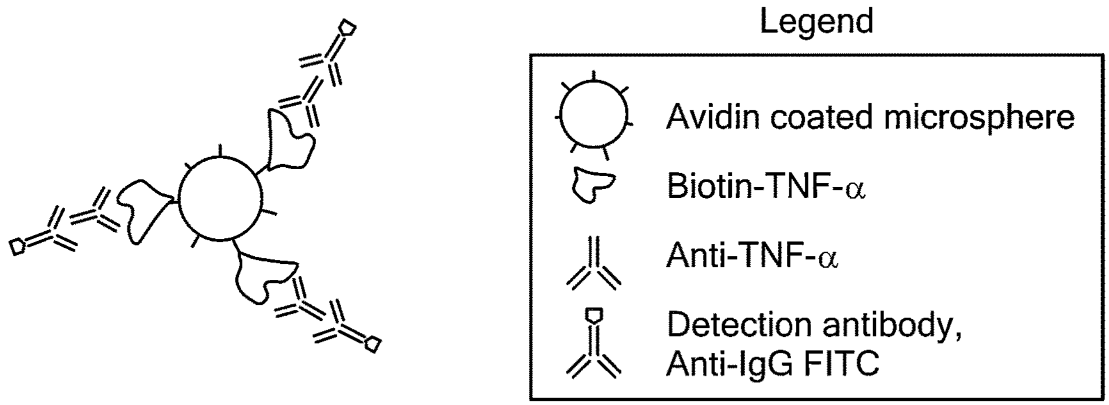
FIG. 12A is a schematic representation of a microsphere-based sensor formed during detection of an anti-TNF-$\alpha$ antibody as an analyte in a method of the invention.
Figure 13A:
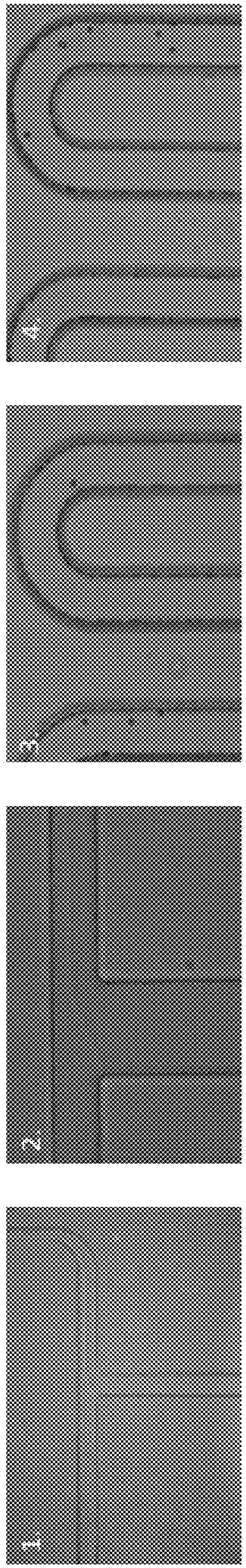
FIG. 13A is a series of phase contrast images of embodiments of methods of the invention. Panel 1 shows the intersection of liquid streams from inlets 1 and 2 in the first laminar flow channel, panel 2 shows the intersection of liquid streams from the first mixing channel and inlet 3 in the second laminar flow channel, panel 3 shows the liquid stream in the second mixing channel during detection of an anti-TNF-$\alpha$ antibody as an analyte, and panel 4 shows the liquid stream in the second mixing channel during detection of TNF-$\alpha$ as an analyte.
Figure 13B:
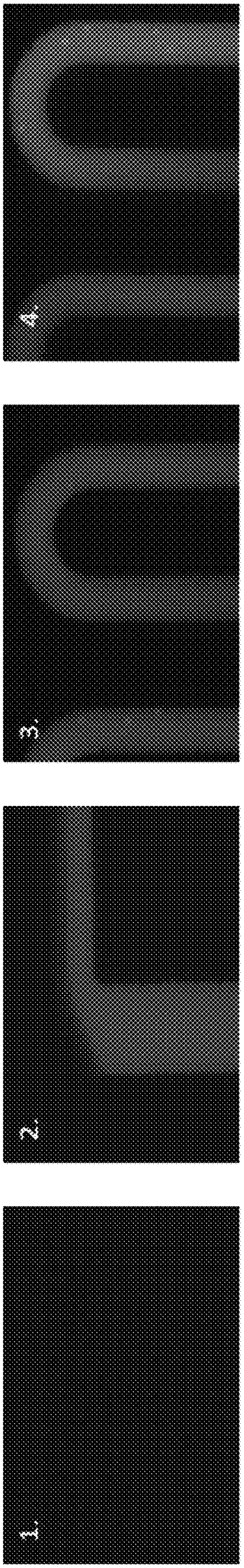
FIG. 13B is a series of fluorescence images corresponding to the phase contrast images in FIG. 13A.

To demonstrate the real-time detection capabilities of the LOC device, efforts were focused on detecting anti-TNF-α antibody. FIG. 12A describes the microsphere-based assay that was introduced into microfluidic format for anti-TNF-α detection. Avidinilated microspheres were conjugated off-chip to biotinylated human TNF-α protein via avidin-biotin bridge (Konry et al., 2009; Diamdandis et al. 1991) as described in Example 1. Next, the generated anti-TNF-α microsphere-based sensors were introduced into the microfluidic device via inlet 2 while the analyte, mouse monoclonal anti-human TNF-α antibody, was introduced via inlet 1. The interaction of the two components resulted in the capture of anti-TNF-α antibodies by microsphere-based sensors in the first mixing channel of the device. Next, the detection antibody, FITC-labeled anti-mouse IgG, was introduced into inlet 3. The fluorescent signal on the microsphere sensor, generated by the conjugation of the captured anti-TNF-α antibody with the fluorescently labeled detection antibody, is demonstrated in FIG. 13B, panel 3.

Figure 14A:
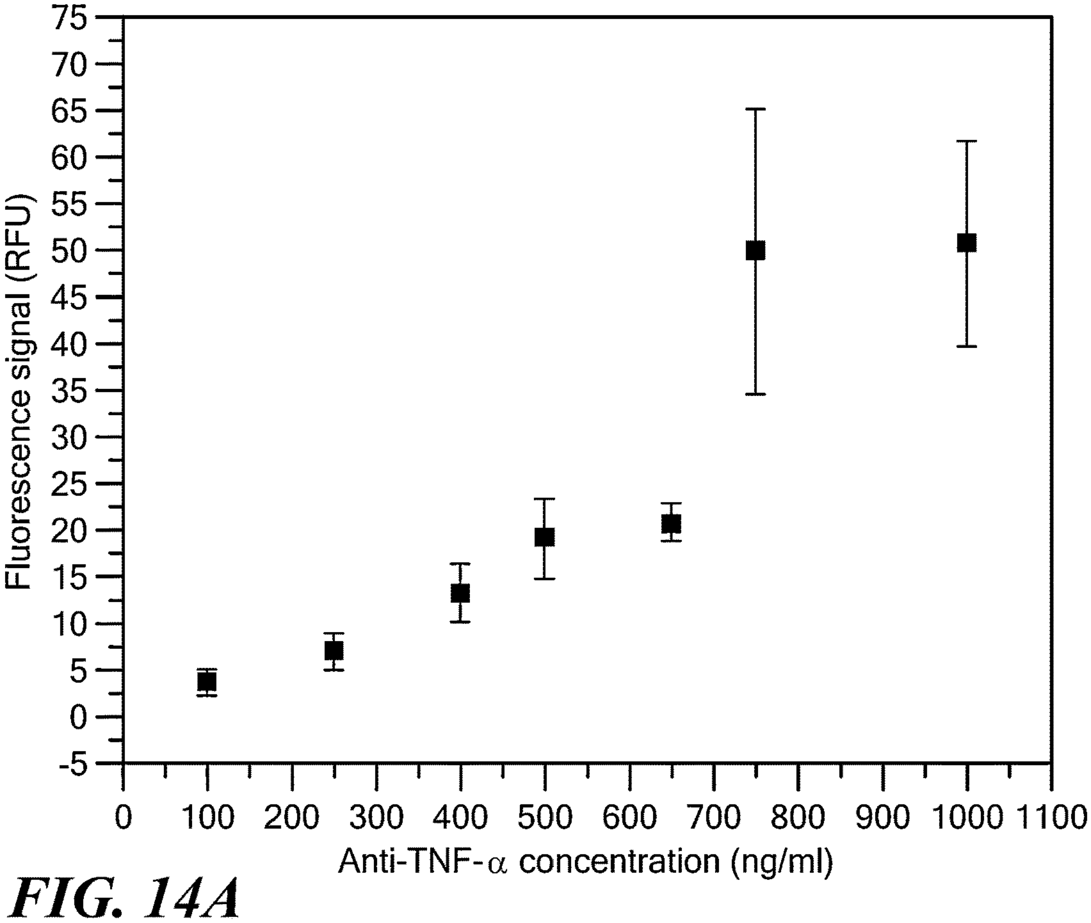
FIG. 14A is a graph of the microsphere-bound fluorescence signal at different concentrations of anti-TNF-α antibody according to a method of the invention.
Figure 14B:
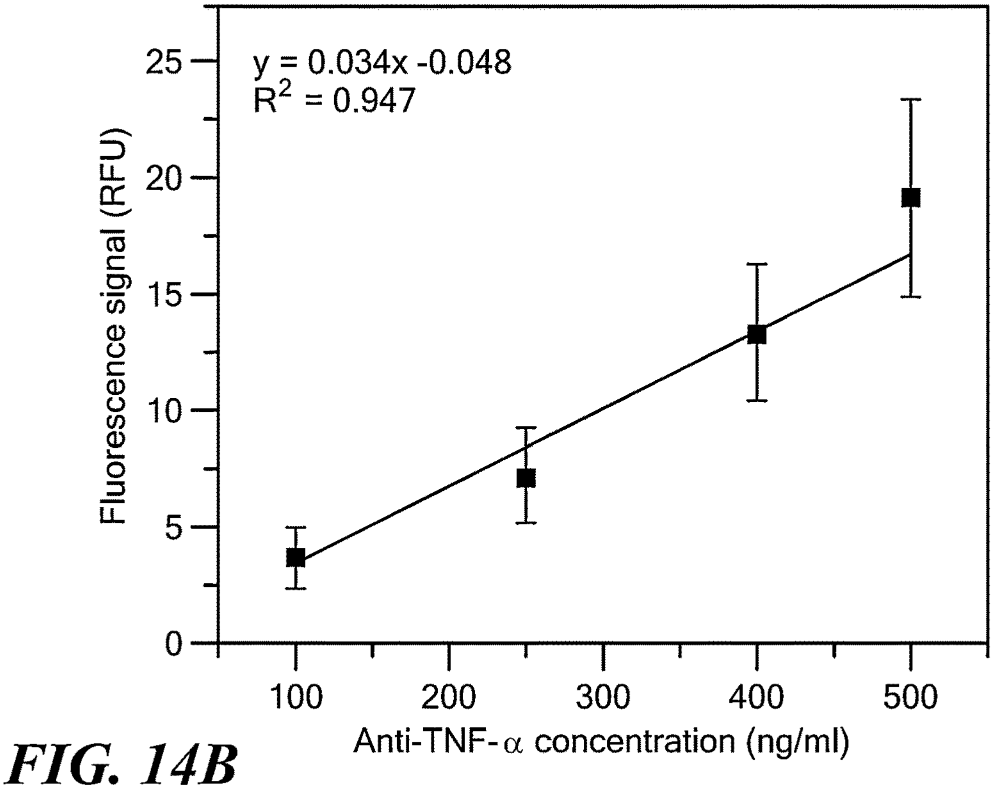
FIG. 14B shows a subset of the data points from FIG. 14A in the linear portion of the plot.

The standard curve for the anti-TNF-α antibody immunoassay was obtained by collecting data from thirty microspheres for each concentration point ranging from 100 to 1000 ng/ml in the device. FIG. 14A shows a typical behavior for the standard calibration curve with an exponential growth, as seen from the curve fit, which results in a linear range shown in FIG. 14B. The curve fit in FIG. 14B was carried out using an equation of the form y=A+B(x), where x is the anti-TNF-α antibody concentration and y is the corresponding fluorescent response signal obtained. The standard curve was most useful for quantification of concentrations from 100 ng/ml and higher, showing in this range an acceptable square correlation coefficient, $R^2$, of 0.94 and a satisfactory sensitivity of 3.67 relative fluorescence units (RFU) (determined within the linear concentration range of the biosensor as the slope, B, of the calibration curve). At higher concentrations, the curve levels off with a response saturation observed from concentration 750 ng/ml and above. The detection limit of the immunosensor was defined as the amount (or concentration) of the analyte that gives a response that is significantly different (three standard deviations) from the background analysis, that is itself obtained from negative control (a sample without analyte). The background signal recorded for the blank (in absence of the analyte, Table 1, experiment 3) and its calculated standard deviation revealed a limit of quantification for a concentration of anti-TNF-α as low as 100 ng/ml that was recorded in the incubation channel after 22.7 s in flow. Thus the developed microsphere based LOC device demonstrated higher detection sensitivity for anti-TNF-α antibodies than that recorded previously in well-established immunoassays such as ELISA, where the detection limit was reported to be 0.5-1 mg/mL (Sino Biological Inc., Cat. no. 10602-MM01). To validate the specificity of the developed LOC assay the set of experiments described in Table 1 was conducted. The results in Table 1 show that the responses from experiments 2 and 3 (in absence of capture molecule and analyte) are all relatively negligible.

TABLE 1

| Exp. | Avidin micro-sphere | Biotinylated Human TNF-α | Mouse Anti-Human TNF-α | FITC Anti-Mouse IgG | Normalized response |
|---|---|---|---|---|---|
| 1 | + | + | + | + | 1 |
| 2 | + | − | + | + | 0.03 |
| 3 | + | + | − | + | 0.16 |

Example 4: TNF-α Cytokine Immunoassay

Figure 12B:
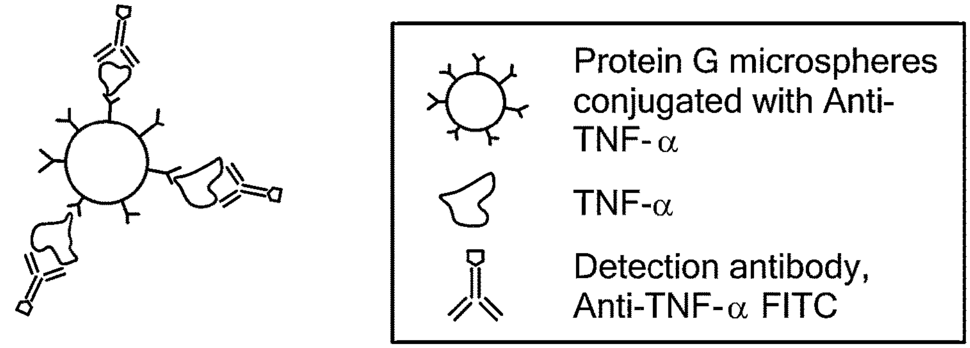
FIG. 12B is a representation of a microsphere-based sensor formed during detection of TNF-$\alpha$ as an analyte in a method of the invention.

Next, the LOC device was adapted for TNF-α cytokine detection in real-time. FIG. 12B describes the microsphere-based assay using TNF-α as a model cytokine. In this system, protein-G microspheres were conjugated off-chip to anti-TNF-α antibodies as described in Example 1. Next, the generated microsphere-based sensors were introduced into the microfluidic device via inlet 2 while the analyte, TNF-α, was introduced via inlet 1. The interaction of the two components resulted in the capture of TNF-α by microsphere-based sensors in the first mixing channel of the device. Next, the detection antibody, FITC-labeled anti-rat TNF-α antibody, was introduced into inlet 3. The fluorescent signal on the microsphere sensor, generated by the conjugation of the captured TNF-α with the fluorescently labeled detection antibody is demonstrated in FIG. 13B, panel 4.

Figure 14C:
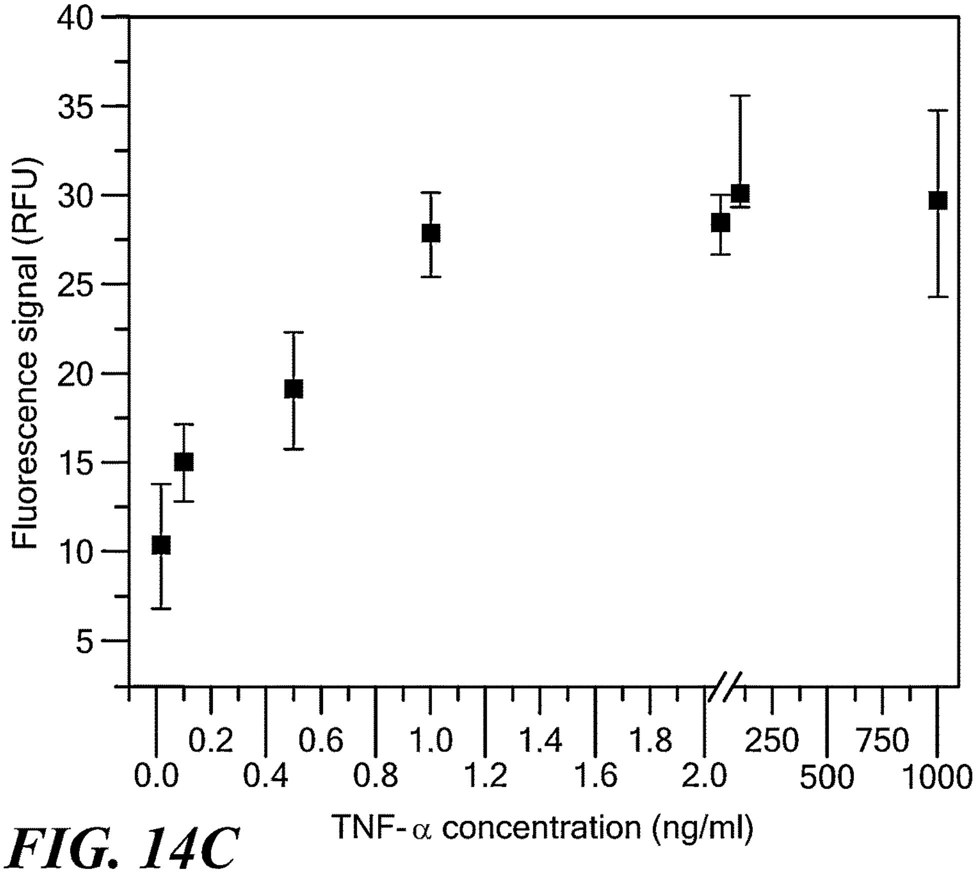
FIG. 14C is a graph of the microsphere-bound fluorescence signal at different concentrations of TNF-α according to a method of the invention.
Figure 14D:
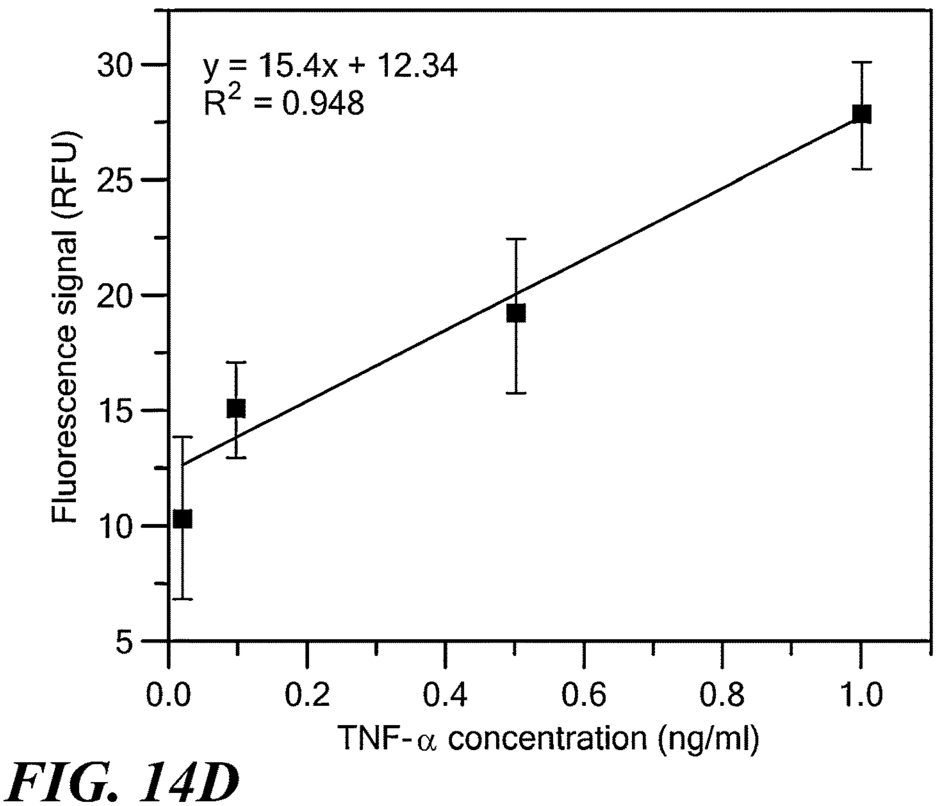
FIG. 14D shows a subset of the data points from FIG. 14C in the linear portion of the plot.

The standard curve for the TNF-α immunoassay was obtained by collecting data from thirty microspheres for each concentration point ranging from 0.02 to 1000 ng/ml in the device. FIG. 14C shows a typical behavior for the standard calibration curve with an exponential growth, as seen from the curve fit, which results in a linear range shown in FIG. 14D. The curve fit in FIG. 14D was carried out using an equation of the form y=A+B(x), where x is the TNF-α antibody concentration and y is the corresponding fluorescent response signal obtained. The standard curve was most useful for quantification of concentrations from 0.02 ng/ml and higher, showing in this range an acceptable square correlation coefficient, $R^2$, of 0.95 and a satisfactory sensitivity of 10.36 RFU (determined within the linear concentration range of the biosensor as the slope, B, of the calibration curve). At higher concentrations, the curve levels off with a response saturation observed from concentration 100 ng/ml and above. The detection limit of the immunosensor was defined as the amount (or concentration) of the analyte that gives a response that is significantly different (three standard deviations) from the background analysis that is itself obtained from negative control (a sample without analyte). The background signal recorded for the blank (in absence of the analyte, Table 2, experiment 3) and its calculated standard deviation revealed a limit of quantification for a concentration of TNF-α as low as 0.02 ng/ml that was recorded in the incubation channel after 22.4 s in flow. This is similar to sensitivity previously reported by standard ELISA method (R&D systems, Cat. no. 510-RT-010, sensitivity 0.05 of ng/mL) and commercially available luminex assay (Human TNF-α Singleplex Bead Kit, Invitrogen, Cat. no. LHC3011, sensitivity 0.01 ng/ml). To validate the specificity of the developed LOC assay the set of experiments described in Table 2 was conducted. The results in Table 2 show that the responses from experiments 2 and 3 (in absence of capture molecule and analyte) are all relatively negligible.

TABLE 2

| Exp. | Protein G microsphere | Anti-Human TNF-α | TNF-α | FITC Anti-TNF-α | Normalized response |
|---|---|---|---|---|---|
| 1 | + | + | + | + | 1 |
| 2 | + | − | + | + | 0.14 |
| 3 | + | + | − | + | 0.18 |

Example 5: Mathematical Model for a Well-Mixed Lab-On-a-Chip Device

In non-mixed solutions in microsphere-based immunosorbent assay and ELISA, the binding reaction rates for reagents with low binding equilibrium constant, such as high affinity antibody-antigen interaction, depend on diffusion (Porstmann et al., 1992). Further increase of reaction surface or decrease of reaction volumes will not decrease the reaction time. Therefore most, if not all, non-mixing immunoassay systems are incubated for 1-2 hours (Kusnezow et al., 2006; Ruslinga et al., 2010). Integrating microsphere-based immunoassays with microfluidic LOC has one major advantage over flat surface assays such as ELISA (Crowther, 2001; Mannerstedt et al., 2010); microspheres have larger surface area, so the interaction between microspheres and target molecules in flow based format is practically comparable with solution-phase kinetics. This integrated format allowed changes in levels of analytes to be observed in near real time since all reagents are continuously replenished in the device.

To support the finding of real-time detection, a mathematical model for in-flow well-mixed immunoassay reaction on a microsphere surface was developed. In the experimental setup, the microspheres move within the well-mixed solution in incubation channels (FIG. 11C). The fast mixing profile of the reaction reagents in the mixing channels implies that the adsorption reaction on the detecting microspheres is different from classical non-mixed bulk immunosorbent assays like ELISA. The equations describing detection reaction inside the mixing LOC channel are as follows:

$$A + B \underset{k_{off}}{\overset{k_{on}}{\rightleftarrows}} AB \quad K_D = \frac{k_{off}}{k_{on}} = \frac{[A]\cdot[B]}{[AB]} \tag{14}$$

$$\partial C_s/\partial t = k_{on}C_d(C_{s0} - C_s) - k_{off}C_s \tag{15}$$

with the initial condition:

$$C_s(t=0)=0 \tag{16}$$

where A, is the analyte, B is the detection antibody, AB is the analyte-detection antibody complex, $C_s$ is the surface concentration of an analyte on the microsphere, $C_d$ is the analyte concentration in the bulk volume $C_{s0}$ is the maximum concentration of the analyte on the microsphere, predefined by the total number of the biding sites, $k_{on}$ is the association rate constant and $k_{off}$ is the dissociation rate constant of the binding reaction, $K_D$ dissociation constant and t is the reaction time.

The complete solution for concentration of the molecule of interest on the microsphere appears in Eq. 17:

$$C_s=-k_{on}C_dC_{s0}/(k_{on}C_d+k_{off})\exp(-(k_{on}C_d+k_{off})t)+k_{on}C_dC_{s0}/(k_{on}C_d+k_{off}) \tag{17}$$

Thus the time $t_h$ for reaction in the well-mixed channels for a deviation h from the equilibrium coverage (Eq. 13) is:

$$t_h=-(k_{on}C_d+k_{off})^{-1}\ln\big(h\big(1+k_{off}/k_{on}C_d\big)-k_{off}/k_{on}C_d\big) \tag{18}$$

and specifically, for analyte/antigen-antibody reactions with small dissociation constant thus with large $k_{on}$ (Song et al. 2008):

$$\lim_{k_{on}\to\infty} t_h \approx 0 \tag{19}$$

Thus, in well-mixed reactors, the conjugation/coverage (h) on the moving microsphere surface can be achieved almost instantly in the ideal systems with very low dissociation constants. These fundamental differences in the reaction kinetics limiting step make the developed mixing channel technology an ideal system for miniaturized immunosorbent reactions as it overcomes the major constrain of the rapid detection-diffusion.

Example 6: Dynamic Monitoring and Imaged Device Implementing a Bead Assay

Figure 10A:
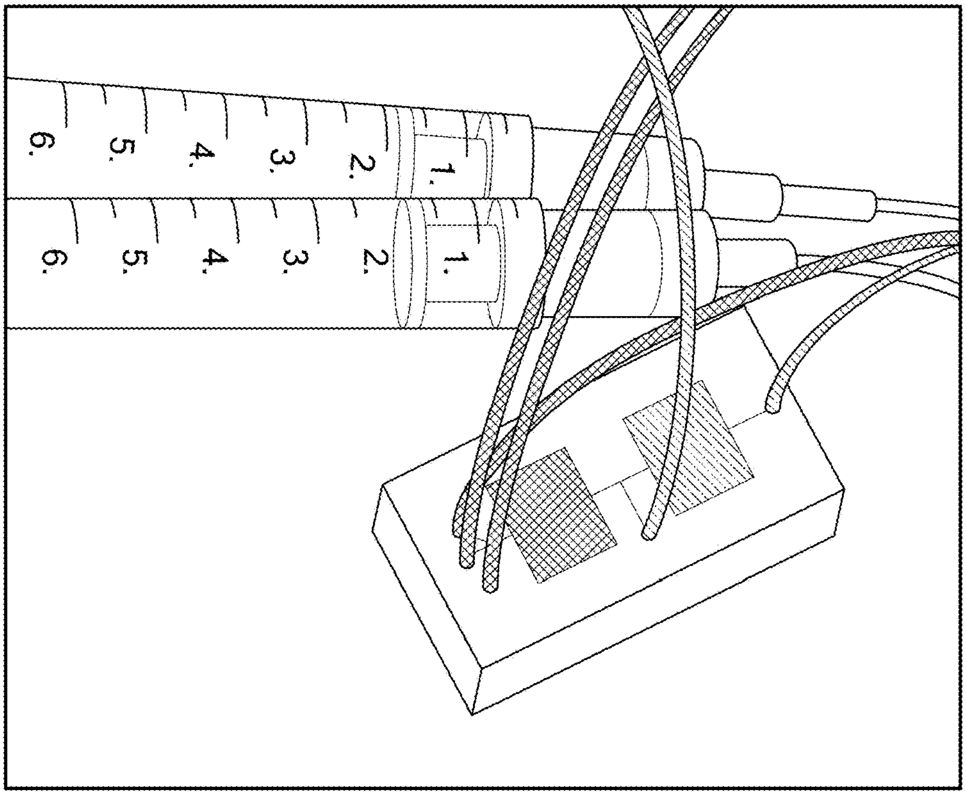
FIG. 10A is an image of an embodiment of a microfluidic device of the invention, including input tubing, output tubing, and syringes for adding fluid and reagents to the system.
Figure 10B:
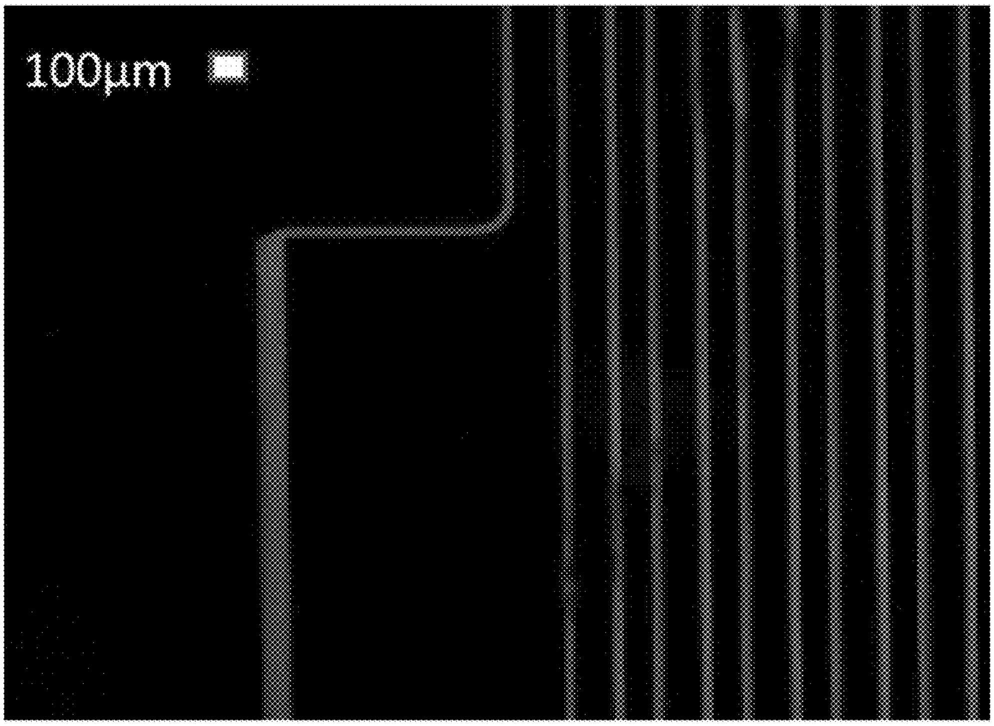
FIG. 10B is a schematic of an embodiment of a microfluidic device of the invention and the binding reactions that occur in a method of using the device to detect an antigen in a sample.
Figure 10C:
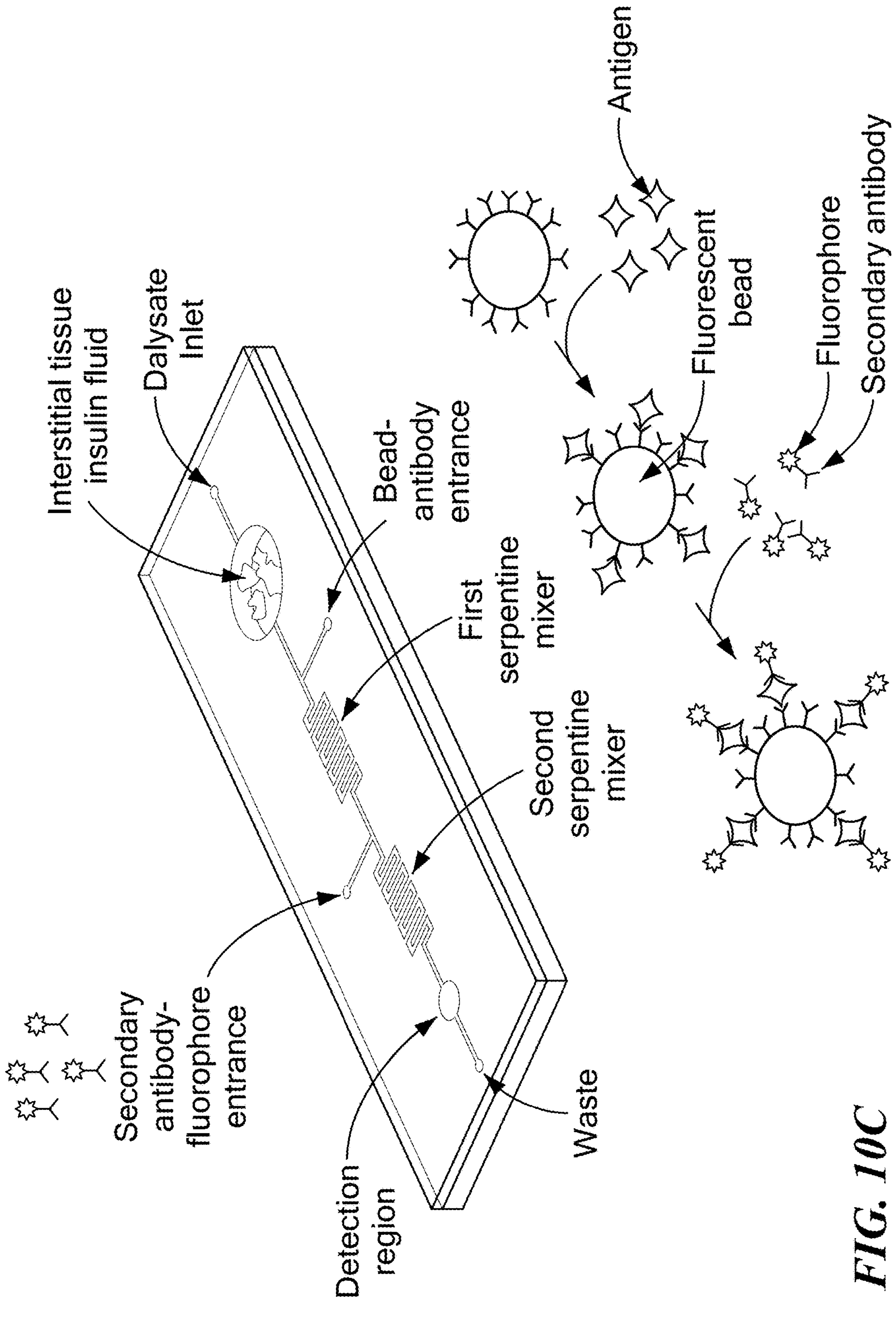
FIG. 10C is a fluorescence image of a solution containing a fluorescently-labeled antibody passing through a portion of a channel of a microfluidic device of the invention.
Figure 10D:
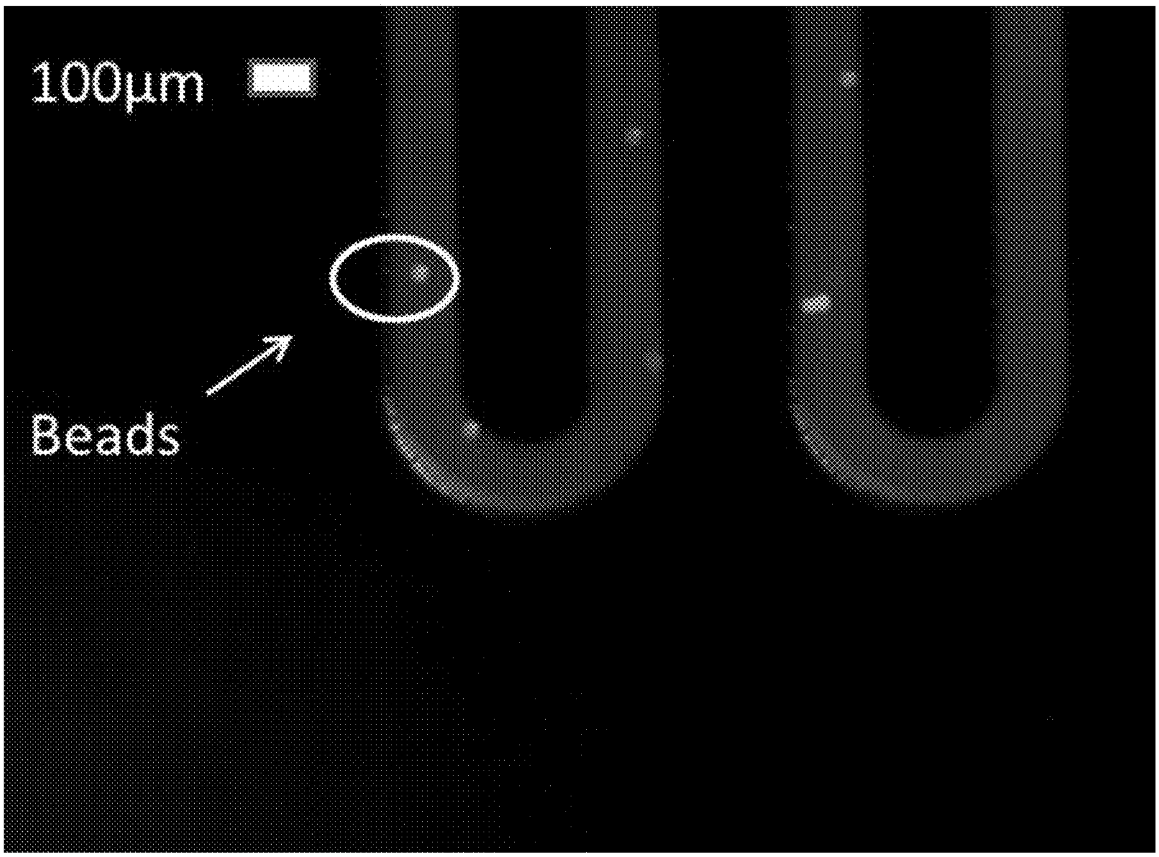
FIG. 10D is a fluorescence image of a suspension containing fluorescently-labeled microspheres, or "beads," passing through a portion of a channel of a microfluidic device of the invention. One fluorescently-labeled bead is circled.

Motivated by the necessity to improve the performance of insulin monitoring in type 1 diabetes patients, a flow through device that continuously samples analytes has been developed (Konry et al., 2012). Feasibility studies have been applied by adapting and integrating the simple bead based assay to a microfluidic experimental platform. This will allow the assay to be dynamic and miniaturized for faster clinical analysis. The microfluidic device was developed and designed for a flow-through device. FIG. 10B schematically illustrates the device design. The polydimethylsiloxane (PDMS) microfluidic system integrated the microsphere-based immunoassay detection scheme. Syringe A was used to introduce the microspheres at 0.5 mg/ml conjugated to biotinylated HTB-125 anti-insulin together with human insulin sampled solution. As the microsphere antibody and insulin solution flowed through the serpentine channel, the insulin was captured by the antibody coated microspheres. The microsphere insulin complex consequently met the secondary antibodies. These antibodies were conjugated with a specific fluorophore. Following incubation with the microsphere antibody-insulin antibody complex, a localized fluorescent signal was attained (see FIGS. 10C and 10D). The high surface area-to-volume ratio of the microsphere as well as the diffusive mixing in the serpentine channel of the microfluidic device reduces the incubation time, enabling continuous flow-through detection. This form of assay was continuously replenished, and therefore it was possible to observe the changes in levels of insulin over a period of time. It took a few minutes for a fluorescence signal to appear on the beads. This enabled detection of different levels of insulin, and measurement of $t_{max}$, and performance of pharmacokinetic experiments.

Example 7: Microsphere-Based Regular Human Insulin Immunoassay

Figure 15A:
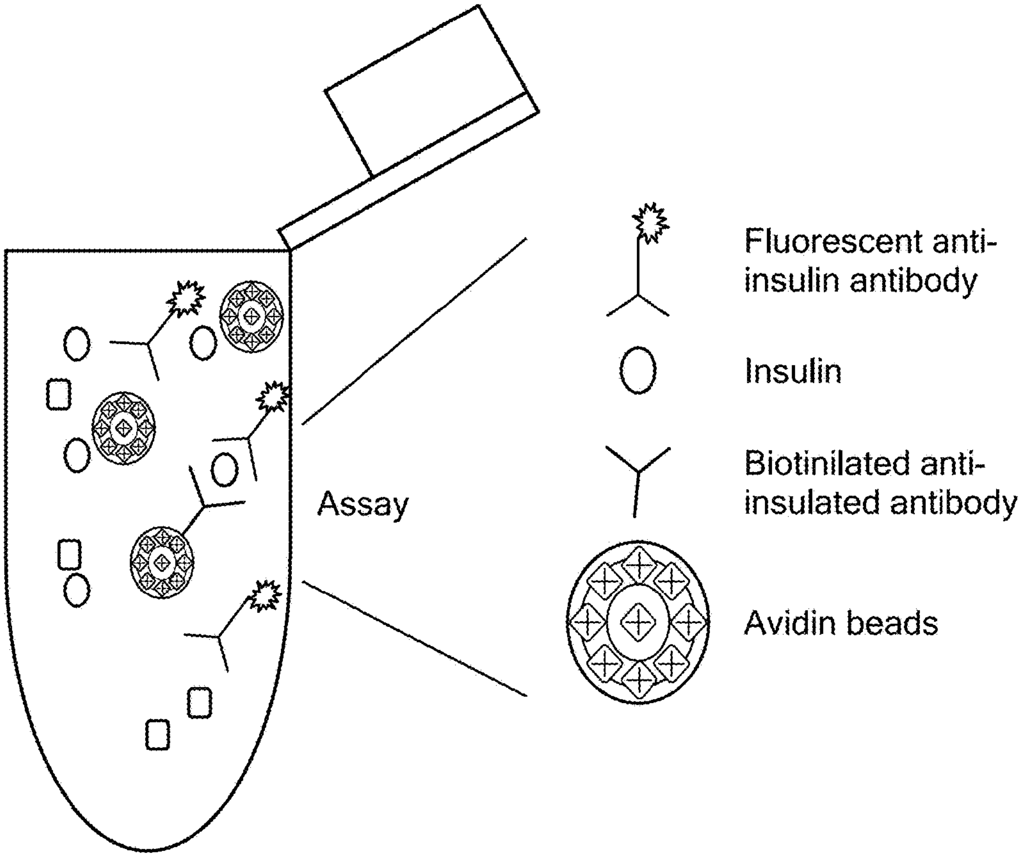
FIG. 15A is a schematic of the complexes formed in the microsphere-based insulin immunoassay performed in a tube format.
Figures 1, 15B:
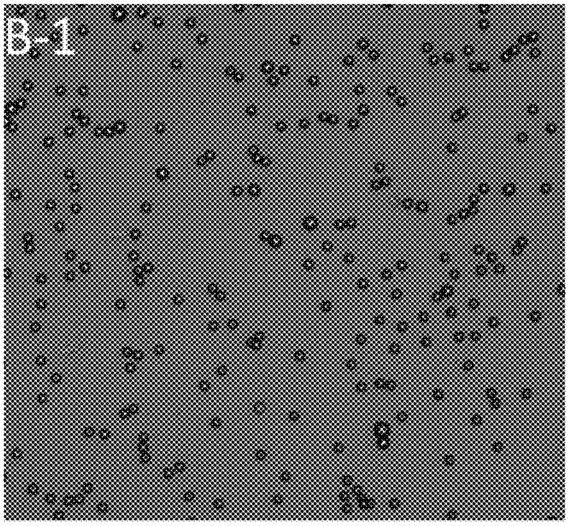
Figures 2, 15B:
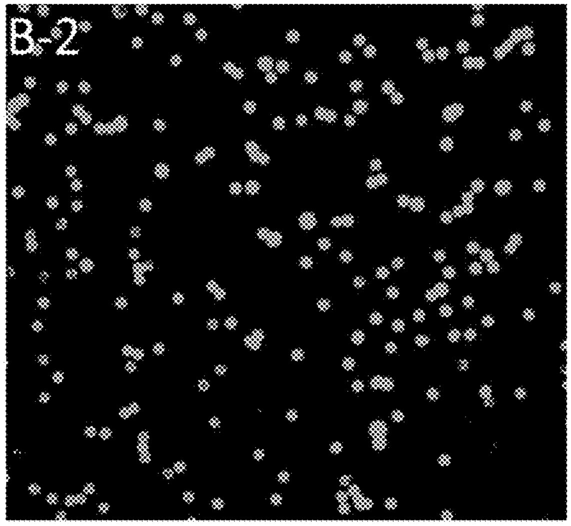

The microsphere-based insulin detection system is depicted as a conceptual scheme in FIG. 15A. Streptavidin coated microspheres were conjugated with a biotin-labeled anti-insulin monoclonal antibody HTB-125 (capture antibody) and non-specific binding reduced by blocking the microsphere surface. The microsphere sensor formulation, conjugated with anti-insulin capture antibodies, was then gently mixed with various test samples for 30 minutes, and allowed to react with the putative target analyte. Thereafter, fluorescently labeled anti-insulin monoclonal antibody HTB-124 (detection 'marker' antibody) was added, and allowed to react through gentle mixing for 30 minutes and the beads were washed with PBS, terminating the process. The beads were then spread on a slide and the fluorescence signal imaged by a fluorescent microscope (FIG. 15B-2 shows an example).

Figure 16A:
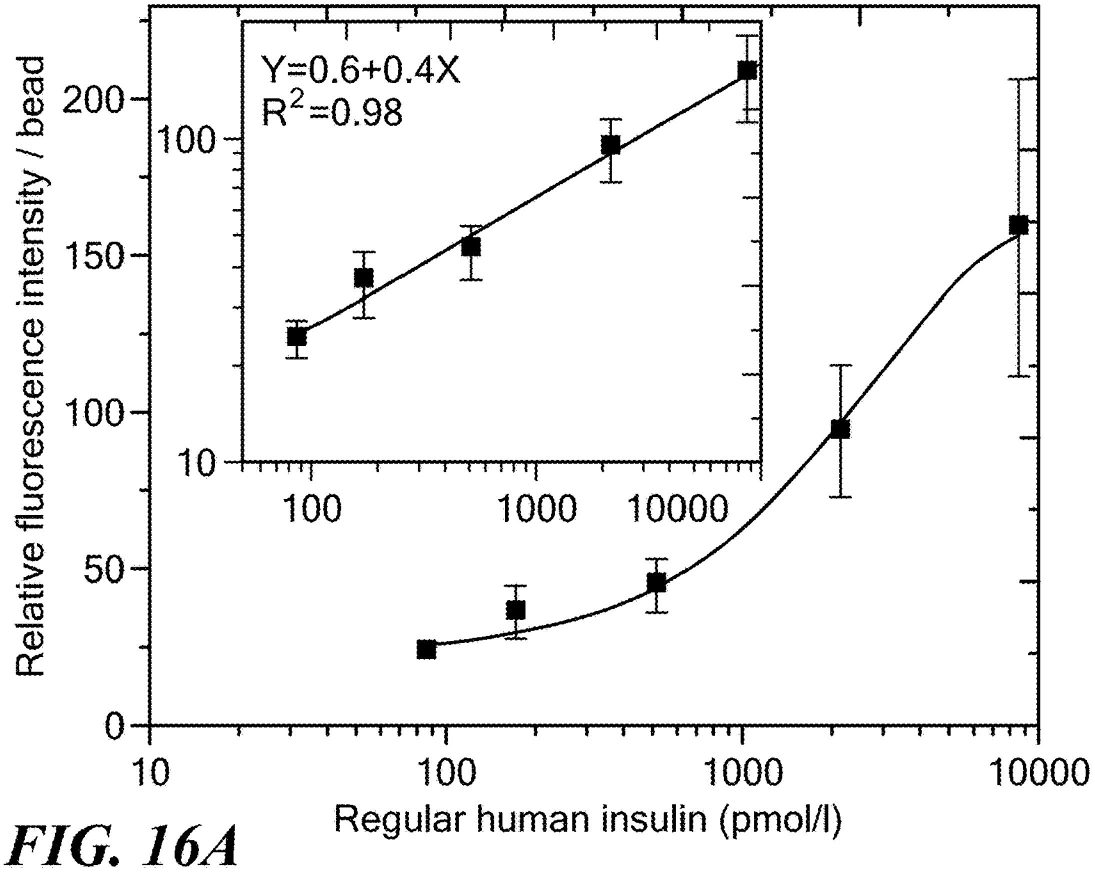
FIG. 16A shows graphs of the microsphere-bound fluorescence signal at different concentrations of insulin according to a method of the invention. Large graph has linear-log scale, and inset graph has log-log scale and a linear regression of the plot.

Using this assay, a calibration curve was derived for RHI (FIG. 16A and Table 3). A log-log transformation of the data was linear from the limit of detection of 100 PM to 8000 pM ($r^2$=0.98). patients with type 1 diabetes range between 50-180 pM (7-25 μIU/ml) and peak post-prandial insulin concentrations are usually less than 1800 pM (250 μIU/ml) (El-Khatib et al., 2007). The microsphere-based assay was therefore linear across most of the clinical range of insulin concentrations.

TABLE 3

Mathematical parameters and performance

| | Characteristics | | |
|---|---|---|---|
| | Regular human insulin | Insulin lispro | Insulin aspart |
| Linear parameters | | | |
| a (slope) | 0.4 | 0.3 | 0.2 |
| B | 0.6 | 0.79 | 1.05 |
| $r^2$ | 0.98 | 0.96 | 0.99 |
| Performance criteria | | | |
| Dynamic range (pM) | 98-8,000 | 123-7,000 | 229-6,000 |
| Limit of detection | 98 | 123 | 229 |

Example 8: Microsphere-Based Assay for Insulin Analogs

Figure 16B:
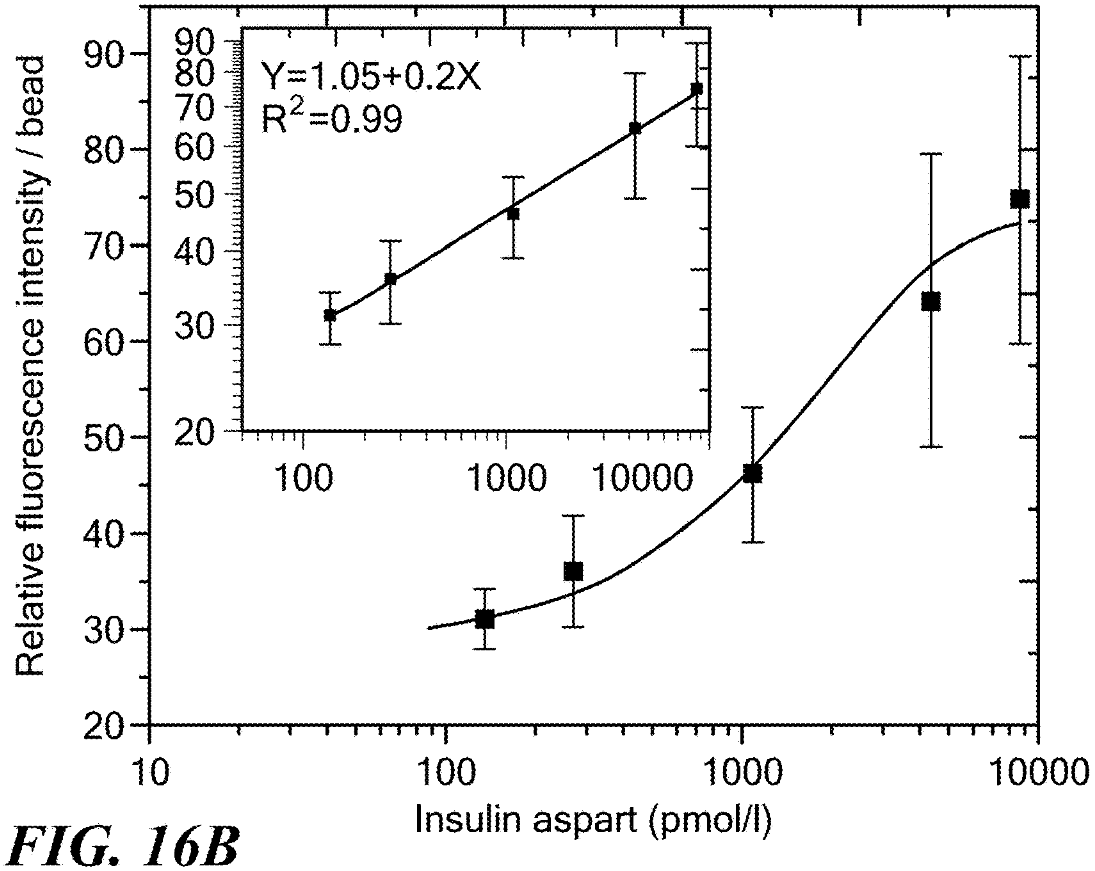
FIG. 16B shows graphs of the microsphere-bound fluorescence signal at different concentrations of insulin aspart according to a method of the invention. Large graph has linear-log scale, and inset graph has log-log scale and a linear regression of the plot.
Figure 16C:
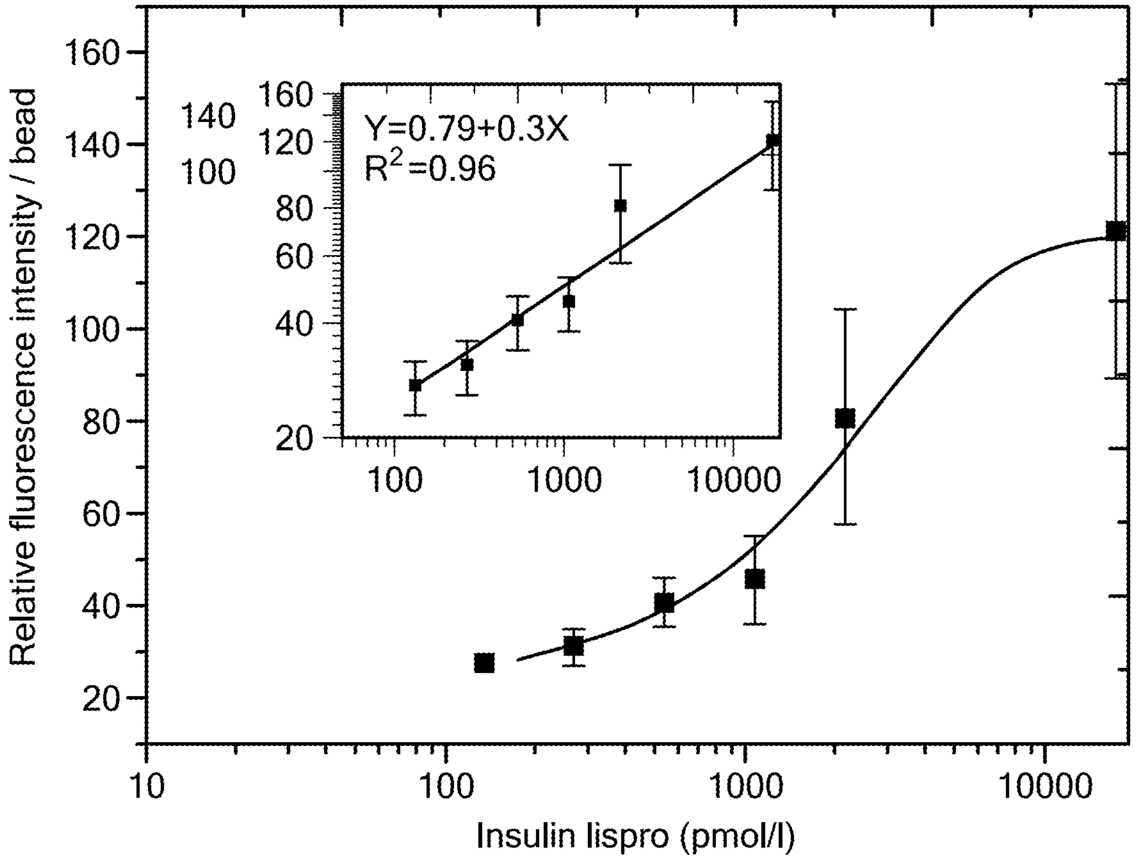
FIG. 16C shows graphs of the microsphere-bound fluorescence signal at different concentrations of insulin lispro according to a method of the invention. Large graph has linear-log scale, and inset graph has log-log scale and a linear regression of the plots.

After evaluating the performance of the system with regular human insulin, its performance was evaluated with the rapid acting insulin analogues most commonly used by patients with diabetes mellitus, insulin aspart (NovoLog, Novo Nordisk, Bagsværd, Denmark) and insulin lispro (Humalog, Eli Lilly and Company, Indianapolis, IN). The standard curves for the insulin analogs are shown in FIGS. 16B and 16C and mathematical parameters are reported in Table 3.

Example 9: Quantification of Endogenous Regular Human Insulin in Plasma

Figure 17A:
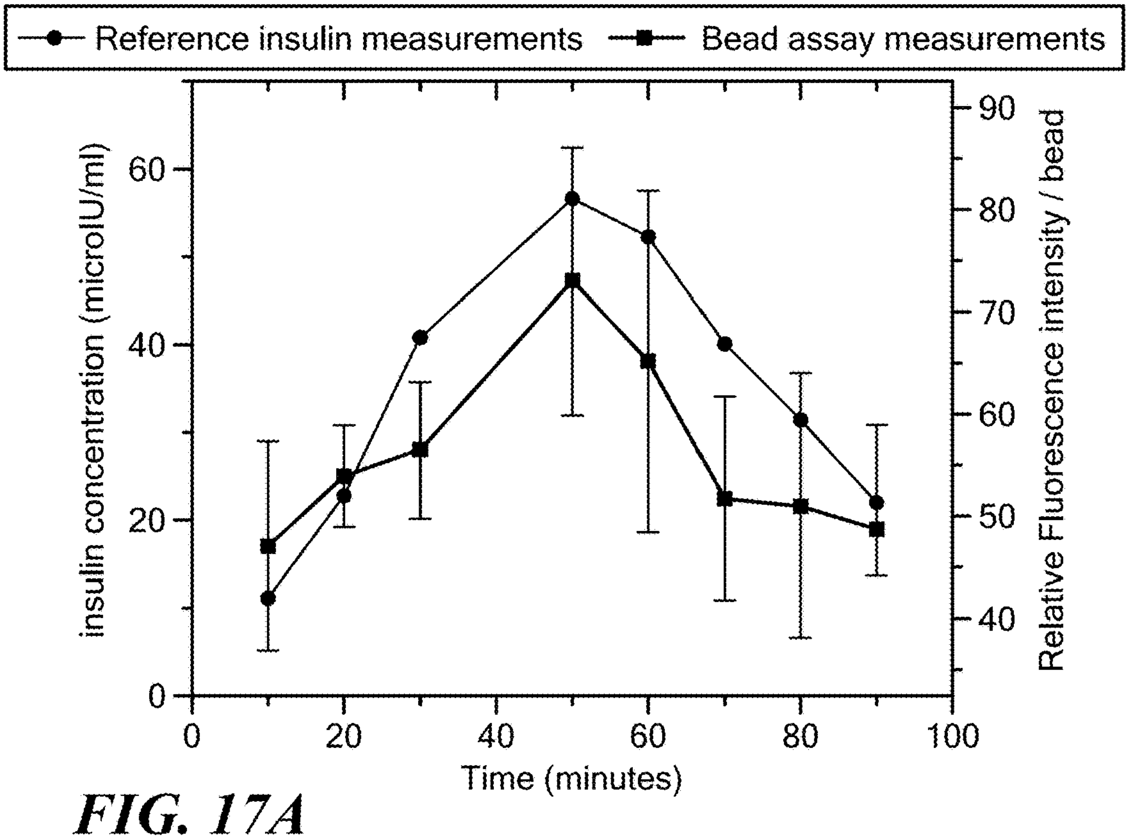
FIG. 17A is graph of concentration of regular human insulin as measured by the Abbot Architect insulin assay (solid circles, units on left axis) and microsphere-bound fluorescence signal according to a method of the invention (solid squares, units on right axis) from plasma samples at various intervals after a subject with normal glucose metabolism ingested a high-carbohydrate meal.

To evaluate the assay in the more complex matrix of human plasma, samples were obtained at intervals from a volunteer with normal glucose metabolism after ingestion of a meal. As shown is FIG. 17A, The results of the microsphere assay followed the same pattern as the reference measurements obtained with the Abbott Architect assay, showing insulin levels rising from basal levels to peak and then clearing. The proportionality between basal and peak insulin levels, as measured by the bead fluorescence assay, was similar to that measured with the reference method.

Example 10: Quantification of Insulin Aspart in Plasma

Figure 17B:
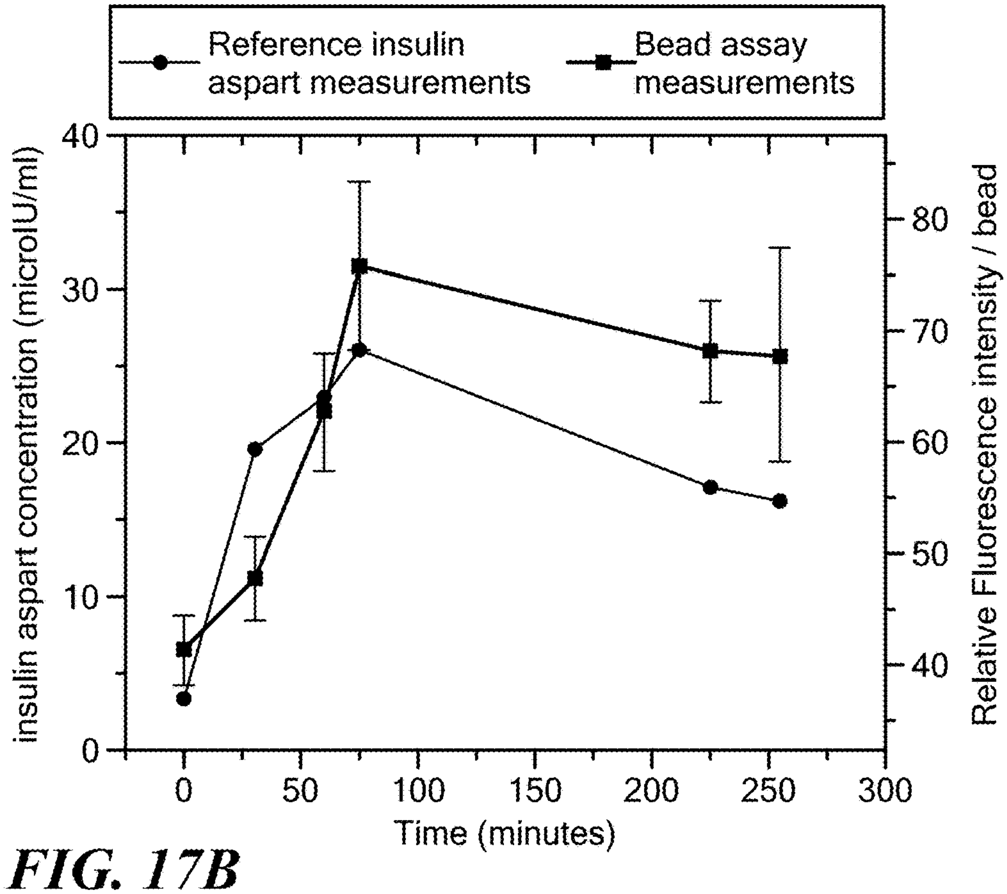
FIG. 17B is graph of concentration of insulin aspart as measured by the Abbot Architect insulin assay (solid circles, units on left axis) and microsphere-bound fluorescence signal according to a method of the invention (solid squares, units on right axis) from plasma samples taken at various intervals after a subject with type 1 diabetes and no endogenous insulin production was given 5 units of insulin aspart.

Most patients with type 1 diabetes use a rapid-acting insulin analog such as insulin aspart. The assay was further tested on plasma samples obtained after injecting a volunteer suffering from type 1 diabetes (C-peptide negative in a mixed-meal tolerance test) with 5 units of insulin aspart. FIG. 17B represents a time series of results of the microsphere assay validated with results obtained with the commercially available Abbott Architect, which is reported to have approximately 75% cross-reactivity with insulin aspart (Moriyama et al., 2006; Heurtault et al., 2014).

Figure 18A:
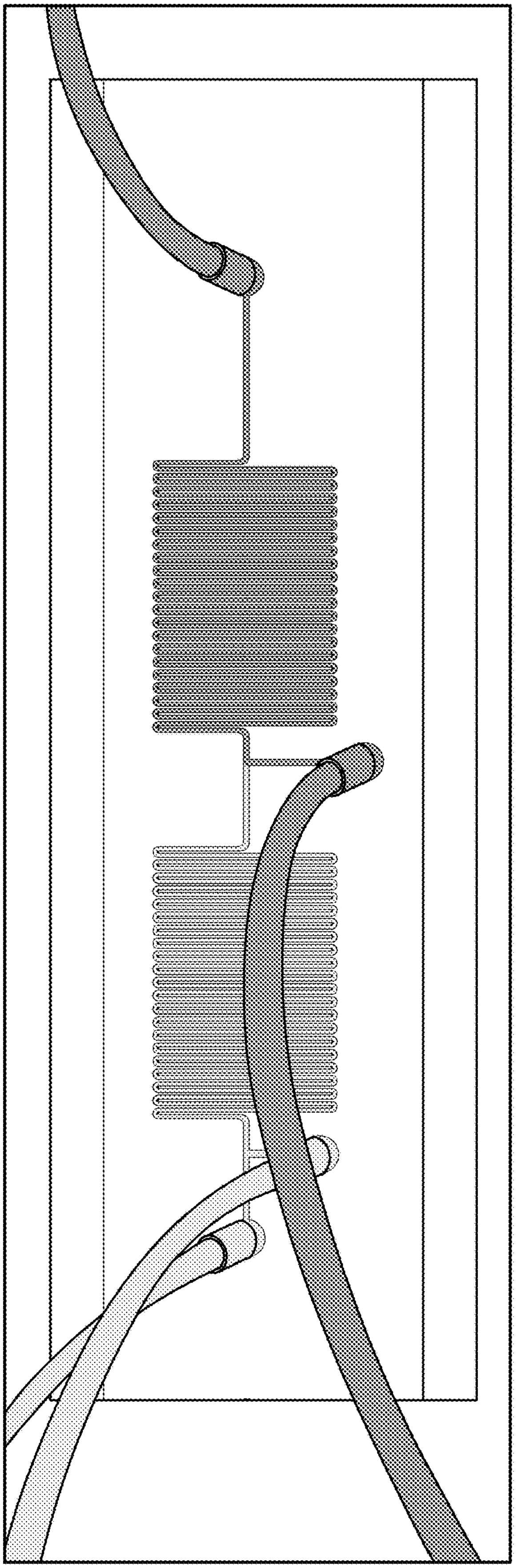
FIG. 18A shows mixing of samples in a microfluidic device of the invention. Solutions with yellow dye (light grey) were pumped into inputs 1 and 2 on the left, and a solution with blue dye (dark grey) was pumped into input 3 in middle. Mixing in the second mixing channel produced a green (medium grey) solution.
Figure 18B:
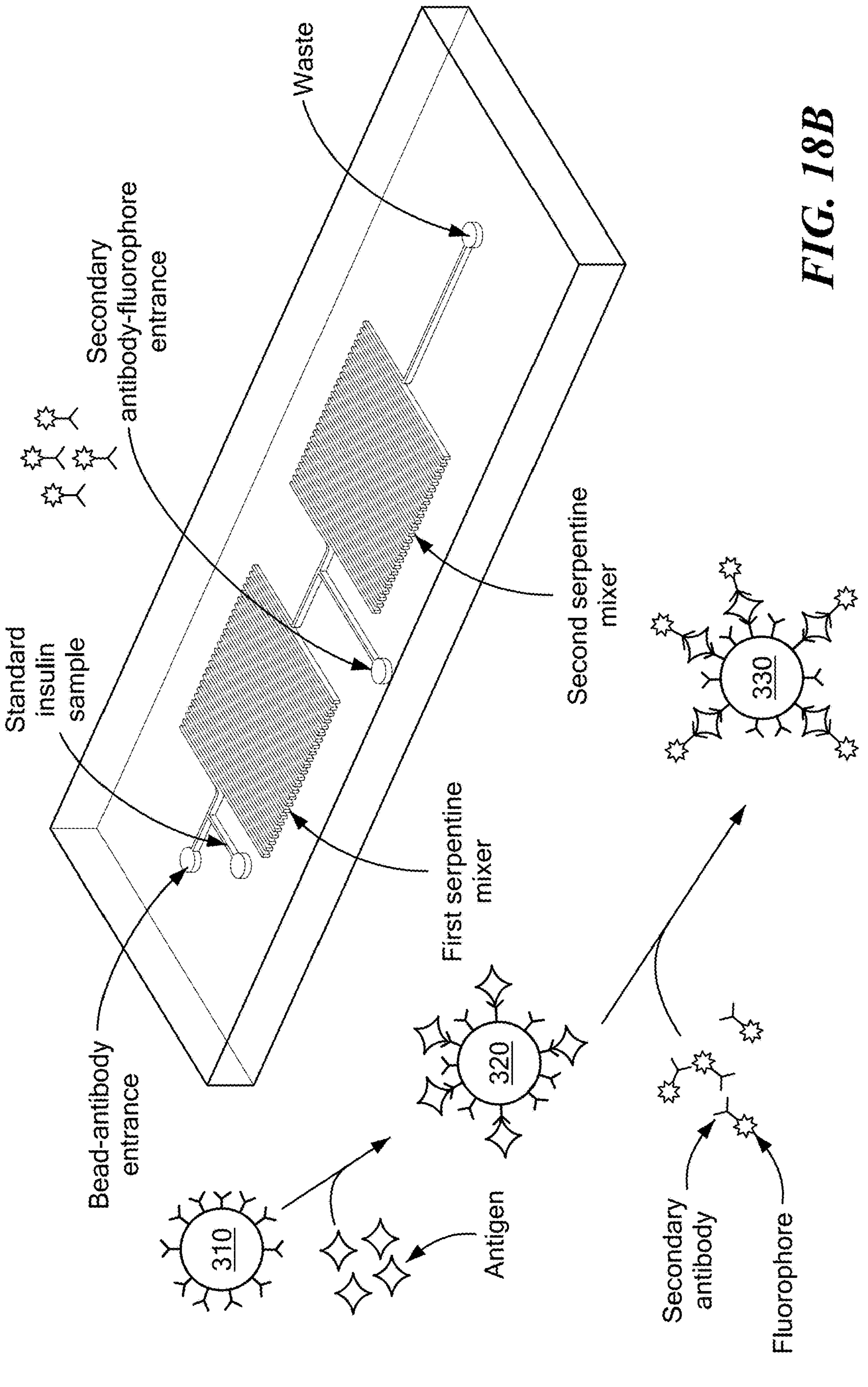
FIG. 18B is a schematic of a microfluidic device of the invention and the binding reactions that occur in a method of using the device to detect an antigen in a sample.
Figure 18C:
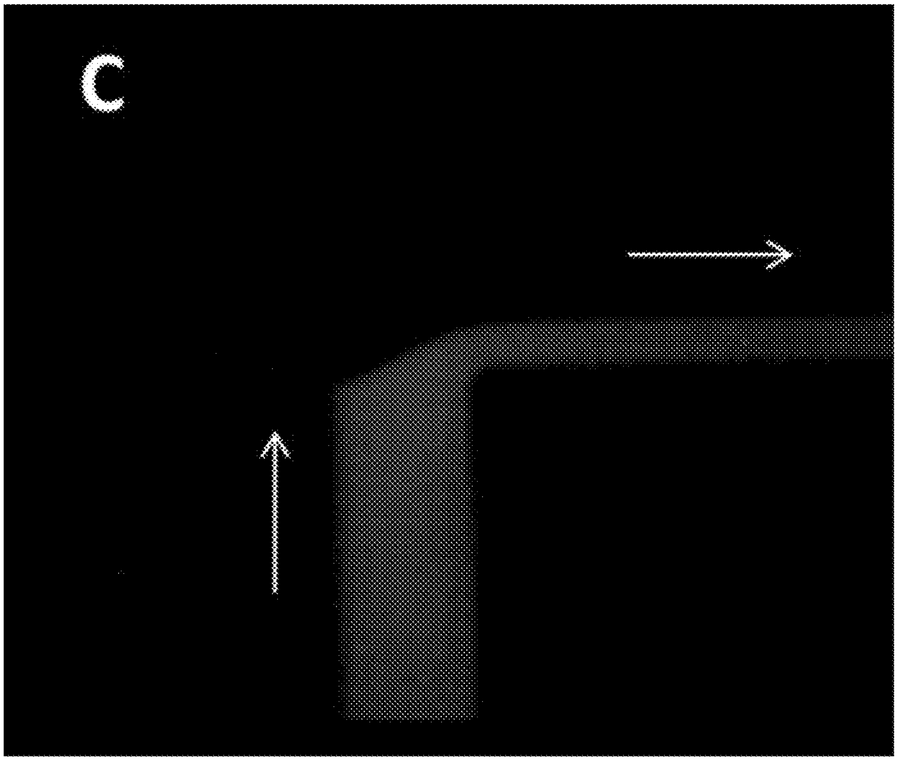
FIG. 18C is an image showing incomplete mixing between a fluorescently labeled antibody solution (from the bottom of the image) and the stream of bead-containing fluid (from the left of the image) in the second laminar flow channel of a microfluidic device of the invention. Arrows indicate direction of fluid flow.
Figure 18D:
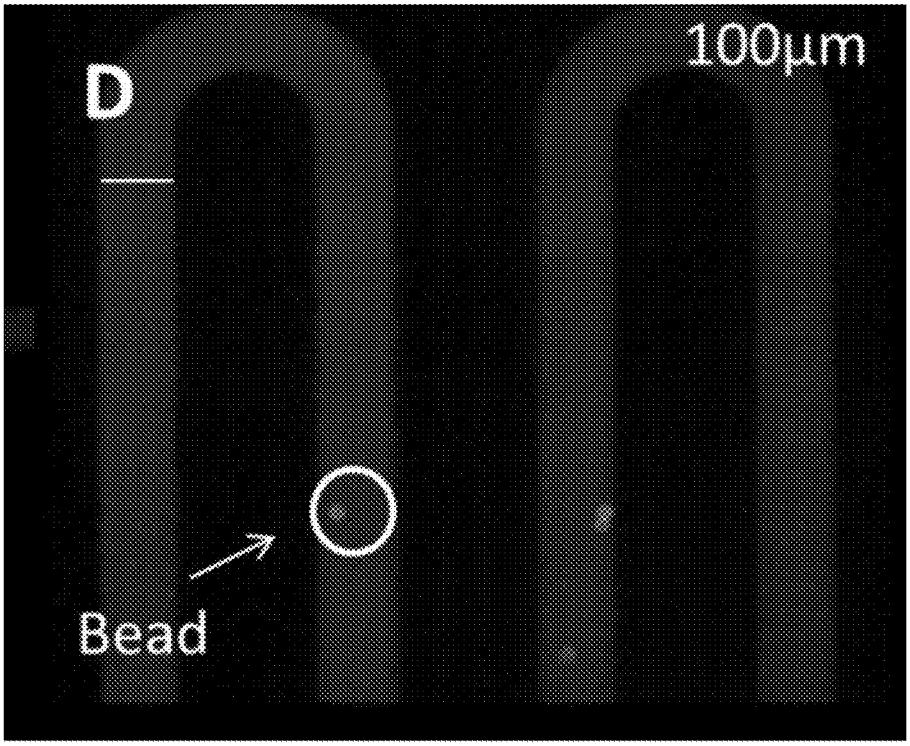
FIG. 18D is an image showing fluorescence at the surface of the insulin antibody-conjugated microspheres in portions of the second mixing channel. One fluorescently-labeled microsphere is circled.

Example 11: Dynamic Monitoring of Insulin Levels in a Flow-Through Microfluidic Platform In order to obtain real-time information about insulin levels, a first generation device with the potential to continuously report insulin levels in a continuous stream of analyte was developed. As a first step, a prototype polydimethylsiloxane (PDMS) microfluidic device was designed as a flow-through device. FIG. 18A shows the device injected with yellow and blue dyes to illustrate the mixing process, while FIG. 18B schematically illustrates the flow-through assay. A solution containing insulin was introduced into the microfluidic device through one inlet port and a suspension of microspheres conjugated to biotinilated HTB-125 anti-insulin monoclonal antibody (310) was introduced into another. The insulin-containing solution and the microsphere suspension then mixed and interacted as they flowed through a serpentine channel, and the putatively present target insulin was captured by the antibody-coated microspheres to form insulin-coated microspheres (320). Thereafter, a solution containing 'marker,' fluorescently labeled HTB-124 (FIG. 18C) anti-insulin monoclonal antibody, was then introduced into a third inlet port, followed by a second serpentine channel enabling a thorough mixing and labeling of any previously occurring biorecognition event. As shown in FIG. 18B, binding of the insulin captured by the solid phase immobilized anti-insulin antibodies on the coated beads enabled the localization of the fluorophore at the surface of the microspheres, thus producing microspheres coated with fluorescent antibodies (330). These microspheres provided a localized fluorescent signal when illuminated by an excitation radiation (FIG. 18D).

Example 12: Enzyme-Based Detection in Microfluidic Platform

Figure 19:
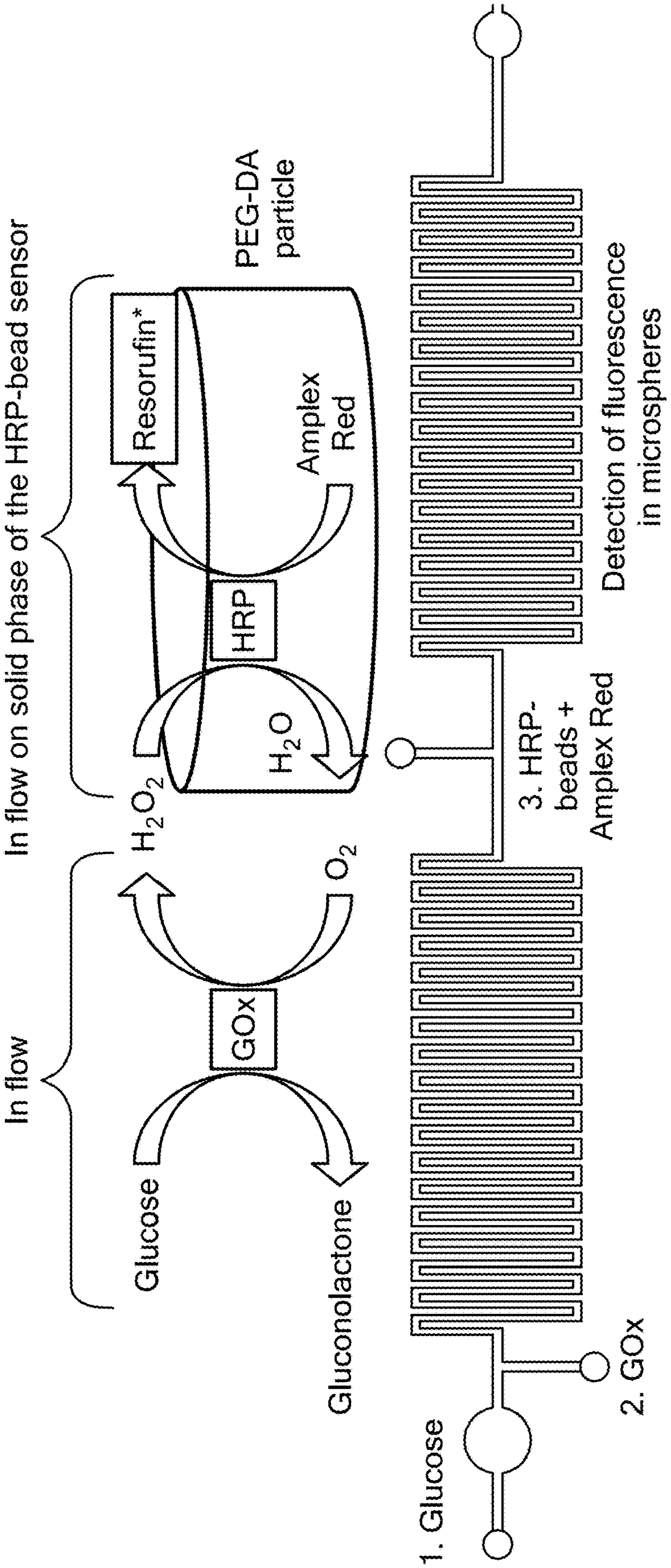
FIG. 19 is a schematic of an embodiment of a device of the invention and its use in an enzyme-based method of detection of a glucose in a liquid sample. GOx, glucose oxidase; HRP, horseradish peroxidase; PEG-DA, polyethylene glycol diacrylate.

FIG. 19 shows an enzyme-based method of detecting glucose using a microfluidic device. In this method, glucose is the analyte, horseradish peroxidase (HRP) is the first enzyme, glucose oxidse (GOx) is the second enzyme, $H_2O_2$ is the diffusible agent, Amplex Red is the indicator precursor, and Resorufin* is the indicator. A liquid sample containing glucose is flowed into the first inlet, and a solution containing glucose oxidase is flowed into the second inlet. As these liquid mix in the first mixing channel, glucose oxidase converts glucose to gluconolactone, resulting in the production of $H_2O_2$. A suspension of hydrogel-based microspheres loaded with HRP and Amplex Red is flowed into the third inlet. The $H_2O_2$-containing efflux from the first mixing channel mixes with the loaded microspheres in the second mixing channel, causing HRP to convert Amplex Red to Resorufin*. The bead-associated fluorescence is measured as the microspheres pass through the detector region. Because Amplex Red is present in excess amounts and reacts stoichiometrically with $H_2O_2$, the Resorufin fluorescence can be used to determine the amount of glucose in the starting sample.

REFERENCES

American Diabetes Associations. Standards of Medical Care in Diabetes. Diabetes Care. 2009; 32(1):S13-S61.

Andersen L, Jørgensen P N, Jensen L B, Walsh D. A new insulin immunoassay specific for the rapid acting insulin analog, insulin aspart, suitable for bioavailability, bioequivalence, and pharmacokinetic studies. Clin Biochem. 2000; 33(8):627-33.

Balkwill, F., 2006. Cancer Metastasis Rev. 25, 409-416.

Batchelor, G., 2000. Introduction to Fluid Mechanics, Cambridge University Press, UK reprinted, Cambridge.

Bayraktar, T., Pidugu, S. B., 2006. Int. J. Heat Mass Transfer 49, 815-824.

Becker, R. H. A., et al., Clinical Endocrinology Diabetes 113, 292-297 (2005).

Beebe, D. J., Mensing, G. A., Walker, G. M., 2002. Annu. Rev. Biomed. Eng. 4, 261-286.

Binder, C., et al., Diabetes Care 7, 2 188-199 (1984).

Bradley, J. R., 2008 J. Pathol. 214, 149-160.

Brustolim, D., Ribeiro-dos-Santos, R., Kast, R. E., Altschuler, E. L., Soares, M. B., 2006. Int. Immunopharmacol. 6, 903-907.

Chen, C. H., Sarkar, A.; Song, Y. A., Miller, M. A., Kim, S. J., Griffith, L. G., Lauffenburger, D. A., Han, J., 2011. J. Am. Chem. Soc. 133, 10368-10371.

Cheng L, Pacey G E, Cox J A. Carbon electrodes modified with ruthenium metallodendrimer multilayers for the mediated oxidation of methionine and insulin at physiological pH. Anal Chem. 2001; 73(22):5607-10.

Chevenne D, Trivin F, Porquet D. Insulin assays and reference values. Diabetes Metab. 1999; 25(6):459-76.

Chou J, Wong J, Christodoulides N, Floriano P N, Shanchez X, McDevitt J. Porous bead based Diagnostic platforms: Bridging the Gaps in healthcare. Sensors. 2012; 12(11): 15467-499.

Crowther, J. R., 2001. The ELISA Guidebook, Humana Press Inc., New Jersey.

David, M., Essayan, 2001. J. Allergy Clin. Immunol. 108, 671-680.

Deng B, Liu Z, Luo G, Ma H, Duan M. Rapid quantitative determination and assessment of insulin in oil formulation by micellar electrokinetic capillary chromatography. J Pharm Biomed Anal. 2002; 27(1-2):73-80.

Derveaux S, Stubbe B G, Braeckmans K, Roelant C, Sato K, Demeester J, De Smedt S C. Synergism between particle-based multiplexing and microfluidics technologies may bring diagnostics closer to the patient. Anal Bioanal Chem. 2008; 391:2453-67.

Diamdandis, E. P., Christopoulos, T. K., 1991. Clin. Chem. 37, 625-636.

El-Khatib F H, Jiang J, Damiano E R. Adaptive closed-loop control provides blood-glucose regulation using dual subcutaneous insulin and glucagon infusion in diabetic swine. J Diabetes Sci Technol. 2007; 1(2):181-92.

El-Khatib F H, Russell, S J, Nathan D M, Sutherlin R G, Damiano E R. A bihormonal closed-loop artificial pancreas for type one diabetes. Sci Transl Med. 2010; 2(27):1-12.

Feldman, M., Maini, R. N., 2003. Nat. Med. 9, 1245-1250.

Feuerstein, G. Z., Liu, T., Barone, F. C., 1994. Cerebrovasc Brain Metab. Rev. 6, 341-360.

Gervais, T., Jensen, K. F., 2006. Chem. Eng. Sci. 61, 1102-1121.

Henry, C. Anal Chem. 1; 70(17):594A-598A (1998) September

Heurtault B, Reix N, Meyer N, Gasser F, Wendling M J, Ratomponirina C, Jeandidier N, Sapin R, Agin A. Extensive study of human insulin immunoassays: promises and pitflls for insulin analogues detection and quantification. Clinical Chem Lab Med. 2014:52(3): 355-362.

Hirsch I B, Armstrong D, Bergenstal R M, Buckinham B, Childs B P, Clarke W L, Peters A, Wolpert H. Clinical application of emerging sensor technologies in diabetes management: Consensus guidelines for continuous glucose monitoring (CGM). Diabetes Technol Ther. 2008; 10(4):232-44.

Hirsch, I. B. N. Engl. J. Med. 352, 174-183 (2005).

Hou, C., Herr, A. E., 2010. Anal. Chem. 82, 3343-3351.

Hu, G., Gao, Y., Li, D., 2007. Biosen. Bioelectron. 22, 1403-1409.

Huang, L. R., Cox, E. C., Austin, R. H., Sturm, J. C., 2004, Science 304, 987-990

Jungheim K., et al Diabetes Care. 2001 September; 24(9): 1696-7.

Junhai Kai, Aniruddha Puntambekar, Nelson Santiago, Se Hwan Lec, David W. Schy, Victor Moore, Jungyoup Han and Chong H. Ahn, 2012. Lab Chip 12, 4257-4262.

Juvenile Diabetes Research Foundation Continues Glucose Monitoring Study Group, Tamborlane W V, Beck R W, Bode B W, Buckinham B, Chase H P, Clemons R, Fiallo-Scharer R, Fox L A, Gillian L K, Hirsch I B, Huang E S, Kollman C, Kowalski A J, Laffel, L, Lawrence J M, Lee J, Mauras N, O'grady M, Ruedy K J, Tansey M, Tsalikian E, Weinzimer S, Wilson D M, Wolpert H, Wysocki T, Xing D. Continuous glucose-monitoring and intensive treatment of type 1 diabetes. N Engl J Med. 2008; 359(14): 1464-1476.

Kai, J., Puntambekar, A., Santiago, N., Lec, S. H., Schy, D. W., Moore, V.; Hana, J., Ahnab, Kankare, J., Vinokurov, I. A., 1999. Langmuir 15, 5591-5599.

Konry T, Bale S S, Bushman A, Shen K, Seker E, Polyak B, Yarmush, M. Particles and microfluidics merged: perspectives of highly sensitive diagnostic detection. Microchimia Acta. 2012; 176(3-4):251-69.

Konry T, Hayman R B, Walt D R. Microsphere-based rolling circle amplification microarray for the detection of DNA and proteins in a single assay. Anal Chem. 2009; 81(14):5777-82.

Konry, T., Hayman, R. B., Walt, D. R., 2009. Anal. Chem. 81, 5777-5782.

Kusnezow, W., Syagailo, Y. V., Ruffer, S.; Baudenstiel, N., Gauer, C., Hoheisel, J. D., Wild, D., Goychuk, I. 2006, Mol. Cell Proteomics 5, 1681.

Lee, J. H., Cosgrove, B. D., Lauffenburger, D. A., Han, J. J., 2009. Am. Chem. Soc. 131, 10340-10341.

Leese G P, Wang J, Broomhall J, Kelly P, Marsden A, Morrison W, Frier B M, Morris A D, DARTS/MEMO Collaboration. Frequency of severe hypoglycemia requiring emergency treatment in type 1 and type 2 diabetes: A population-based study of health service resource use. Diabetes Care. 2003; 26(4):1176-80.

Lim, C. T., Zhang, Y., 2007. Biosens. Bioelectron. 22, 1197-1204.

Locksley, R. M., Killeen, N., Lenardo, M. J., 2001. Cell 104, 487-501.

Mannerstedt, K., Jansson, A. M., Weadge, J., Hindsgaul, O., 2010. Angew. Chem. Int. Ed. 49, 8173.

Mao, C., Liu, A., Cao, B., 2009. Angew. Chem. Int. Ed. 48, 6790.

Marques, L. J., Zheng, L., Poulakis, N., Guzman, J., Costabel, U., 1999. Am. J. Respir. Crit. Care Med. 159, 508-511.

Martinez, A. W., Phillips, S. T., Carrilho, E., Thomas, III, S. W., Sindi, H., Whitesides, G. M. 2008. Anal. Chem. 80, 3699-3707.

Moriyama M, Hayashi N, Ohyabu C, Mukai M, Kawano S, Kumagai S. Performance Evaluation and Cross Reactivity from Insulin Analogs with the ARCHITECT Insulin assay. Clinical Chemistry. 2006; 52(7):1423-25.

Mudaliar, S. R., et al., Diabetes Care 22, 9 1501-6 (1999).

Nathan D M, Cleary P A, Backlund J Y, Genuth S M, Lachin J M, Orchard T J, Raskin P, Zinman B, The Diabetes Control and Complications Trial/Epidemiology of Diabetes Interventions and Complications (DCCT/EDIC) Study Research Group. Intensive diabetes treatment and cardiovascular disease in patients with type 1 diabetes. N Engl J Med. 2005; 353(25): 2643-53.

Ng, A. H. C., Uddayasankar, U., Wheeler, A. R., 2010. Anal. Bioanal. Chem. 397, 991-1007.

Ng, A. H., Choi, K., Luoma, R. P., Robinson, J. M., Wheeler, A. R., 2012. Anal. Chem. 84, 8805-8812.

Nie, S., Henley, W. H., Miller, S. E., Zhang, H., Mayer, K. M., Dennis, P. J., Oblath, E. A., Alarie, J. P., Wu, Y., Oppenheim, F. G., Little, F. F., Uluer, A. Z., Wang, P., Ramsey, J. M., Walt, D. R., 2014. Lab Chip 14, 1087-1098.

Oita, I, Anal Bioanal Chem (2010) 398:239-264

Parsa, H., Chin, C. D., Mongkolwisetwara, P., Lee, B. W., Wang, J. J., Sia, S. K., 2008. Lab Chip 8, 2062-2070.

Patel, P. P., Chang, L., Rivnak, A. J., Ferrell, E. P., Randall, J. D., Provuncher, G. K., Walt, D. R, Duffy, D. C., 2010. Nat. Biotechnol. 28, 595-599.

Petitti D B, Klingensmith G J, Bell, R A, Andrews J S, Dabelea D, Imperatore G, Marcovina S, Pihoker C, Standiford D, Waitzfelder B, Mayer-Davis E. SEARCH for Diabetes in Youth Study Group, Glycemic control in youth with diabetes: The SEARCH for diabetes in Youth Study. J Pediatr. 2009; 155(5):668-72.

Porstmann, T., Kiessig, S. T., 1992. J. Immunol. Methods 150, 5-21.

Reach, G., and Wilson, G. S. Anal Chem. 15; 64(6):381A-386A. March (1992) Reichert, J. M., 2001. Nat. Biotechnol. 19, 819.

Rissin D. M., Kan, C. W., Campbell, T. G., Howes, S. C., Fournier, D. R., Song, L., Piech, T., Rolla, A., The American Journal of Medicine, Vol 121, No 6A, S9-S19 (2008)

Roper M G, Shackman J G, Dahlgren G M, Kennedy R T. Microfluidic Chip for Continuous Monitoring of Hormone Secretion from Live Cells Using an Electrophoresis-Based Immunoassay. Anal Chem. 2003; 75(18):4711-17.

Ruslinga, J. F., Kumara, C. V., Gutkinde, J. S., Patel, V., 2010. Analyst. 135, 2496-2511.

Russell S J, El-Khatib F H, Nathan D M, Damiano E R. Efficacy determinants of subcutaneous microdose glucagon during closed-loop control. Journal of Diabetes Science and Technology. 2010; 4(6): 1288-96.

Russell, S. J., et al Diabetes Care 35: 2148-2155, 2012

Scallon, B., Cai, A., Solowski, N., Rosenberg, A., Song, X. Y., Shealy, D., Wagner, C. J., 2002. Pharmacol. Exp. Ther. 301, 418-426.

Sharp, K. V., Adrian, R. J., 2004. Exp. Fluids 36, 741-747.

Singhal, A., Haynes, C., Hansen, C. L., 2010. Anal. Chem. 82, 8671-8679.

Sloan J H, Clin Biochem. 2012 December; 45(18): 1640-4.

Song, M. Y., Park, S. K., Kim, C. S., Yoo, T. H., Kim, B., Kim, M. S., Kim, Y. S., Kwag, W. J., Lee, B. K., Back, K., 2008. Exp. Mol. Med. 40, 35-42.

Steil G M, Rebrin K, Darwin C, Hariri F, Saad M F. Feasibility of automating insulin delivery for the treatment of type 1 diabetes. Diabetes. 2006; 55(12):3344-50.

Thaitrong, N., Charlermroj, R., Himananto, O., Seepiban, C., Karoonuthaisiri, N., 2013. Plos One 8, c83231.

The Diabetes Control and Complications Trial Research Group. Hypoglycemia in the diabetes control and complications trial. Diabetes. 1997; 46(2):271-86.

The Diabetes Control and Complications Trial Research Group. The effect of intensive treatment of diabetes on the development and progression of long-term complications in insulin dependent diabetes mellitus. N Engl J Med. 1993; 329(14):977-86.

Verpoorte, E. Beads and chips: new recipes for analysis. Lab on chip. 2003; 3(4):60-68.

Wang J, Zhang X. Anal Chem. Needle type dual microsensor for the simultaneous monitoring of glucose and insulin. 2001; 73(4)844-847.

Weinzimer S A, Steil G M, Swan K L, Dziura J, Kurtz N, Tamborlane W V. Fully automated closed-loop insulin delivery versus semiautomated hybrid control in pediatric patients with type 1 diabetes using an artificial pancreas. Diabetes Care. 2008; 31(5):934-9.

Wild, D., 2001. The Immunoassay Handbook, Nature Press, London.

Wolf, M., Juncker, D., Michel, B., Hunziker, P., Delamarche, E., 2004. Biosen. Bioelectron. 19, 1193-1202.

Writing team for the Diabetes Control and Complications Trial/Epidemiology of Diabetes Interventions and Complications Research Group. Effect of intensive therapy on the micro-vascular complications of type 1 diabetes mellitus. JAMMA. 2002; 287(19):2563-69.

Xu M, Luo X, Davis J J. The label free picomolar detection of insulin in blood serum. Biosens Bioelectron. 2013; 39(1):21-5.

Yeh, F. L., Lin, W., Shen, H. D., Fang, R. H., 1997. Burns 23, 6-10.

Zinman, B., et al., N. Engl. J. Med. 321, 363-370 (1989).

What is claimed is:

1. A method of determining a concentration of an analyte in a liquid sample, the method comprising:

(a) providing:

(1) a microfluidic device for continuous flow optical detection of an analyte in a sample, the device comprising:

(i) first and second inlets;

(ii) a first microscale laminar flow channel fluidically connected to the first and second inlets such that liquids entering from the first and second inlets flow in a laminar manner through said first laminar flow channel;

(iii) a first microscale mixing channel fluidically connected to the first laminar flow channel such that liquid entering the first mixing channel from the first laminar flow channel is converted from laminar flow to non-laminar flow in said first mixing channel;

(iv) a second microscale laminar flow channel fluidically connected to the first mixing channel;

(v) a third inlet fluidically connected to the second laminar flow channel such that liquids entering the second laminar flow channel from the third inlet and the first mixing channel flow in a laminar manner in said second laminar flow channel; and (vi) a second microscale mixing channel fluidically connected to the second laminar flow channel such that liquid entering the second mixing channel from the second laminar flow channel is converted from laminar flow to non-laminar flow in said second mixing channel;

(2) a liquid suspension of microspheres, wherein the microspheres are conjugated to a first analyte-binding agent;

(3) a liquid comprising a labeled second analyte-binding agent; and (4) a liquid sample suspected of comprising said analyte; and (b) flowing the liquid comprising the labeled second analyte-binding agent into the first inlet at a first flow rate;

(c) flowing the liquid sample into the second inlet at a second flow rate, whereby mixing of the labeled second analyte-binding agent and the liquid sample in the first mixing channel enables binding of analyte in the liquid sample to the labeled second analyte-binding agent, resulting in formation of labeled complexes of analyte and second analyte-binding agent within the first mixing channel;

(d) flowing the liquid suspension of microspheres conjugated with the first analyte-binding agent into the third inlet at a third flow rate, whereby the conjugated microspheres are coated with the labeled complexes within the second mixing channel;

(e) detecting an amount of microsphere-bound label on individual microspheres as they flow through the second microscale mixing channel or after they exit the second microscale mixing channel and enter a translucent detector region; and (f) determining a concentration of the analyte in the liquid sample based on a previously determined correlation between the amount of microsphere-bound label and concentration of the analyte.

2. The method of claim 1, further comprising detection of a second analyte in the liquid sample wherein in step (b) the labeled second binding agent comprises a second labeled second analyte-binding agent that binds to the second analyte, resulting in formation of a first population of microspheres coated with first labeled second analyte-binding agent that binds first analyte and a second population of microspheres coated with second labeled second binding agent that binds second analyte;

wherein in step (d) the liquid suspension of conjugated microspheres further comprises second microspheres conjugated to a first binding agent that binds the second analyte;

wherein step (e) further comprises detecting an amount of second microsphere-bound second label on individual second microspheres as they flow through the second microscale mixing channel or after they exit the second microscale mixing channel and enter the translucent detector region; and wherein step (f) further comprises determining a concentration of the second analyte in the liquid sample based on a previously determined correlation between the amount of second microsphere-bound second label and concentration of the second analyte.

3. The method of claim 1, wherein binding of the labeled complexes of analyte and second analyte-binding agent to the conjugated microspheres occurs under diffusion-independent binding conditions.

4. The method of claim 1, wherein binding of the analyte to the labeled second analyte-binding agent occurs under diffusion-independent binding conditions.

5. The method of claim 1, further comprising determining a dissociation constant for binding of the analyte to the first analyte binding agent.

6. The method of claim 5, wherein the first analyte binding agent is an antibody.

7. The method of claim 1, wherein the analyte is selected from the group consisting of cytokines, proteins, antibodies, drugs, peptides, amino acids, hormones, growth factors, cellular metabolites, nucleic acids, oligosaccharides, TNF-α, anti-TNF-α antibody, glucose, insulin, glucagon, IL-1, and IL-21.

8. The method of claim 1, wherein the labeled second analyte binding agent is a protein, an antibody, or an antigen-binding fragment thereof.

9. The method of claim 1, wherein the labeled second analyte binding agent is labeled with a fluorescent, luminescent, colorimetric, or phosphorescent moiety.

* * * * *